(12) United States Patent
Rosati et al.

(10) Patent No.: US 8,122,760 B2
(45) Date of Patent: Feb. 28, 2012

(54) METHOD OF ANALYZING PHOSPHOROUS ACID, FOSETYL-AL, OR BOTH SIMULTANEOUSLY

(75) Inventors: Dominique Rosati, Neyron (FR); Catherine Venet, Saint Germain sur l'Arbrisle (FR)

(73) Assignee: Bayer SAS (FR)

( * ) Notice: Subject to any disclaimer, the term of this patent is extended or adjusted under 35 U.S.C. 154(b) by 301 days.

(21) Appl. No.: 11/883,036

(22) PCT Filed: Jan. 23, 2006

(86) PCT No.: PCT/EP2006/001433
§ 371 (c)(1),
(2), (4) Date: Sep. 17, 2007

(87) PCT Pub. No.: WO2006/079566
PCT Pub. Date: Aug. 3, 2006

(65) Prior Publication Data
US 2008/0257019 A1  Oct. 23, 2008

(30) Foreign Application Priority Data

Jan. 25, 2005  (EP) .................................. 05356015
Feb. 11, 2005  (EP) .................................. 05356031
Dec. 16, 2005  (EP) .................................. 05356216

(51) Int. Cl.
  *G01N 1/40* (2006.01)
  *G01N 1/38* (2006.01)
  *G01N 30/06* (2006.01)
(52) U.S. Cl. ...................... 73/61.52; 73/61.55; 73/64.56

(58) Field of Classification Search ................. 73/61.52, 73/61.55, 64.56
See application file for complete search history.

(56) References Cited

U.S. PATENT DOCUMENTS

| | | | | |
|---|---|---|---|---|
| 4,904,595 | A | * | 2/1990 | Gierthy .......................... 435/354 |
| 6,058,940 | A | * | 5/2000 | Lane ............................. 131/298 |
| 6,225,132 | B1 | * | 5/2001 | Drukier et al. ................. 436/541 |
| 6,541,272 | B1 | * | 4/2003 | Mitra ............................ 436/178 |
| 6,749,811 | B2 | * | 6/2004 | Murray ........................... 422/91 |
| 6,786,221 | B2 | * | 9/2004 | Lane ............................. 131/309 |
| 7,238,507 | B2 | * | 7/2007 | Bolten et al. ................... 435/189 |
| 2005/0118650 | A1 | * | 6/2005 | Dasseux et al. ................ 435/7.2 |
| 2006/0138052 | A1 | * | 6/2006 | Leistner et al. ............... 210/692 |
| 2007/0105112 | A1 | * | 5/2007 | Hitchman et al. ................ 435/6 |

OTHER PUBLICATIONS

Hernandez, F. et al.: "Rapid direct determination of pesticides and metabolites in environmental water samples at sub-mug/1 level by on-line solid-phase extraction-liquid chromatography-electrospray tandem mass spectrometry", Journal of Chromatography A, vol. 939, No. 1-2, Dec. 21, 2001, pp. 1-11, XP004312657, ISSN: 0021-9673, abstract.

(Continued)

*Primary Examiner* — David Rogers
(74) *Attorney, Agent, or Firm* — Ostrolenk Faber LLP

(57) ABSTRACT

Method for analyzing one or more pesticidal compounds present in amounts of less than or equal to 0.00005 mg/kg of a sample, comprising the following steps:
  a) preparation of the sample;
  b) optional dilution of the sample prepared;
  c) direct analysis of the optionally diluted sample by high performance liquid chromatography (HPLC)/tandem mass spectrometry (MS/MS).

10 Claims, 82 Drawing Sheets

Table 16: Standard concentrations prepared for the determination of detector linearity. The concentration corresponding to the LOQ is printed in the third column of the table.

| HPLC-MS/MS | Standard Concentrations [µg/L] | | | | | | | |
|---|---|---|---|---|---|---|---|---|
| fosetyl-Al | 0.2 | 0.4 | 0.5 | 0.75 | 1 | 2 | 5 | 10 | 20 |
| phosphorous acid | 0.2 | 0.4 | 0.5 | 0.75 | 1 | 2 | 5 | 10 | 20 |

OTHER PUBLICATIONS

Hernandez, F. et al.: "An estimation of the exposure to organophosphorus pesticides through the simultaneous determination of their main metabolites in urine by liquid chromatography-tandem mass spectrometry", Journal of Chromatography B: Biomedical Sciences & Applications, vol. 808, No. 2, Sep. 5, 2004, pp. 229-239, XP004521132, ISSN 1570-0232, abstract.

Huang, X. et al.: "New approach for the detection of organophosphorus pesticide in cabbage using SPME/SnO2 gas sensor: principle and preliminary experiment" Sensors and Actuators B., vol. 102, No. 2, Sep. 13, 2004, pp. 235-240, XP004534562, ISSN: 0925-4005.

Granby, K.; Vahl M.: Investigation of the herbicide glyphosate and the plant growth regulators chlormequat and mepiquat in cereals produced in Denmark, Food Additives and Contaminants, vol. 18, No. 10, 2001, pp. 898-905, XP0099061410, abstract.

Hernandez, et al.: "Rapid Determination of Fosetyl-Aluminum Residues in Lettuce by Liquid Chromatography/Electrospray Tandem Mass Spectrometry", Journal of AOAC International, vol. 86, No. 4, 2003, pp. 832-838, XP009061375, abstract.

* cited by examiner

Collision energy:

| Compound | Precursor ion Q1 mass (amu) | Product ion Q3 mass (amu) | Dwell time (msec) | Collision energy (CE) (eV) | Declustering potential (V) | Collision cell exit potential (CXP) (V) |
|---|---|---|---|---|---|---|
| fosetyl-Al | 109.0 | 80.9 | 200 | -16 | -45 | -1 |
|  | 109.0 | 63.0 | 200 | -38 | -45 | -5 |
| $H_3PO_3$ | 80.9 | 63.0 | 600 | -38 | -55 | -1 |
|  | 80.9 | 78.9 | 600 | -22 | -55 | -5 |

FIGURE 1

| Quantification level mg/kg | Recovery range [%] | | | | | Means [%] | CV [%] |
|---|---|---|---|---|---|---|---|
| 0.100 | 83 | 82 | 82 | 91 | 95 | 87 | 7.0 |
| 1.000 | 102 | 102 | 101 | 97 | 99 | 100 | 2.2 |
| | | | | | Total CV [%] | 93 | 8.9 |

Cucumber - phosphorous acid

FIGURE 2(a)

| Quantification level mg/kg | Recovery range [%] | | | | | Means [%] | CV [%] |
|---|---|---|---|---|---|---|---|
| 0.010 | 95 | 96 | 98 | 98 | 95 | 96 | 1.6 |
| 0.100 | 106 | 101 | 101 | 99 | 100 | 101 | 2.7 |
| | | | | | Total CV [%] | 99 | 3.4 |

Cucumber - fosetyl-Al

FIGURE 2(b)

| Quantification level mg/kg | Recovery range [%] | | | | | Means [%] | CV [%] |
|---|---|---|---|---|---|---|---|
| 0.100 | 65 | 99 | 70 | 78 | 67 | 76 | 18.3 |
| 1.000 | 97 | 99 | 101 | 95 | 99 | 98 | 2.3 |
| | | | | | Total CV [%] | 87 | 17.3 |

Orange - phosphorous acid

FIGURE 2(c)

| Quantification level mg/kg | Recovery range [%] | | | | | Means [%] | CV [%] |
|---|---|---|---|---|---|---|---|
| 0.010 | 102 | 100 | 98 | 87 | 97 | 97 | 6.0 |
| 0.100 | 96 | 95 | 94 | 90 | 86 | 92 | 4.5 |
| | | | | | Total CV [%] | 95 | 5.6 |

Orange - fosetyl-Al

FIGURE 2(d)

| Quantification level mg/kg | Recovery range [%] | | | | | Means [%] | CV [%] |
|---|---|---|---|---|---|---|---|
| 0.100 | 82 | 94 | 76 | 79 | 74 | 81 | 9.7 |
| 1.000 | 103 | 108 | 98 | 106 | 107 | 104 | 3.9 |
| | | | | | Total CV [%] | 93 | 14.7 |

Lettuce - phosphorous acid

FIGURE 2(e)

| Quantification level mg/kg | Recovery range [%] | | | | | Means [%] | CV [%] |
|---|---|---|---|---|---|---|---|
| 0.010 | 104 | 98 | 109 | 113 | 114 | 108 | 6.2 |
| 0.100 | 102 | 106 | 104 | 107 | 107 | 105 | 2.1 |
| | | | | | Total CV [%] | 106 | 4.5 |

Lettuce - fosetyl-Al

FIGURE 2(f)

| Quantification level mg/kg | Recovery range [%] | | | | | Means [%] | CV [%] |
|---|---|---|---|---|---|---|---|
| 0.100 | 96 | 94 | 113 | 100 | 92 | 99 | 8.5 |
| 1.000 | 100 | 105 | 104 | 101 | 101 | 102 | 2.1 |
| | | | | | Total CV [%] | 101 | 6.0 |

Grape - phosphorous acid

FIGURE 2(g)

| Quantification level mg/kg | Recovery range [%] | | | | | Means [%] | CV [%] |
|---|---|---|---|---|---|---|---|
| 0.010 | 102 | 102 | 95 | 101 | 100 | 100 | 2.9 |
| 0.100 | 101 | 102 | 102 | 102 | 100 | 101 | 0.9 |
| | | | | | Total CV [%] | 101 | 2.1 |

Grape - fosetyl-Al

FIGURE 2(h)

| Quantification level mg/kg | Recovery range [%] | | | | | Means [%] | CV [%] |
|---|---|---|---|---|---|---|---|
| 0.100 | 74 | 77 | 68 | 70 | 75 | 73 | 5.1 |
| 1.000 | 110 | 97 | 92 | 103 | 100 | 100 | 6.7 |
| | | | | | Total CV [%] | 87 | 17.8 |

Avocado - phosphorous acid

FIGURE 2(i)

| Quantification level mg/kg | Recovery range [%] | | | | | Means [%] | CV [%] |
|---|---|---|---|---|---|---|---|
| 0.010 | 104 | 95 | 92 | 94 | 93 | 96 | 5.0 |
| 0.100 | 88 | 88 | 85 | 89 | 86 | 87 | 1.9 |
| | Total CV [%] | | | | | 91 | 6.1 |

<u>Avocado - fosetyl-Al</u>

FIGURE 2(j)

| Quantification level mg/kgb | Recovery range [%] | | | | | Means [%] | CV [%] |
|---|---|---|---|---|---|---|---|
| 0.100 | 90 | 94 | 101 | 102 | 103 | 98 | 5.8 |
| 1.000 | 77 | 77 | 81 | 79 | 81 | 79 | 2.5 |
| | | | | | Total CV [%] | 89 | 12.2 |

Wheat - phosphorous acid

FIGURE 3(a)

| Quantification level mg/kg | Recovery range [%] | | | | | Means [%] | CV [%] |
|---|---|---|---|---|---|---|---|
| 0.010 | 86 | 92 | 93 | 85 | 82 | 88 | 5.4 |
| 0.100 | 75 | 79 | 69 | 71 | 71 | 73 | 5.5 |
| | | | | | Total CV [%] | 80 | 10.9 |

Wheat - fosetyl-Al

FIGURE 3(b)

Table 1: LOQ and principle of analytical determination

| Compound | | fosetyl-Al | Phosphorous acid |
|---|---|---|---|
| Determined as | | fosetyl-Al | Phosphorous acid |
| Calculated as | | fosetyl-Al | Phosphorous acid |
| Principle of Determination | | LC/MS/MS | LC/MS/MS |
| LOQ$^i$ [mg/kg] | Grape (whole fruit) | 0.01 | 0.1 |
| | Orange (whole fruit) | 0.01 | 0.1 |
| | Lettuce (head) | 0.01 | 0.1 |
| | Cucumber (whole fruit) | 0.01 | 0.1 |
| | Avocado (whole fruit) | 0.01 | 0.1 |
| | Wheat (Grain) | 0.01 | 0.1 | i : defined as the lowest validated fortification level

FIGURE 4

Table 2: Reference item data

| Name of Substance | Batch Number | Content [%] | Date of Expiry |
|---|---|---|---|
| fosetyl-Al | 12/1080 | 97.6 | February 20, 2006 |
| phosphorous acid | 04911DN | 96.2 | March 12, 2005 |

FIGURE 5

Collision Gas N$_2$ (CAD): 6Collision Energy:

| Compound | Precursor Ion Q1 Mass (amu) | Product Ion Q3 Mass (amu) | Dwell Time (msec) | Collision Energy (V) |
|---|---|---|---|---|
| fosetyl-Al | 109.0 | 80.9 | 200 | -38 |
| Phosphorous acid | 80.9 | 62.9 | 600 | -16 |

Table 3: Mass spectrometer scan parameters for the quantifier ions used. The detailed instrument settings used are given in chapters Error! Reference source not found. and Error! Reference source not found.. Varying instrument systems or instrument parameters may result in different ion transitions and different relative intensities.

Note: Some mass spectrometer conditions are instrument specific. The spectrometer conditions should be optimised by a competent operator prior to analysis.

FIGURE 6

Proposed fragmentation pathway for fosetyl-Al

Proposed fragmentation pathway for phosphorous acid

| Compound | Precursor Ion Q1 Mass (amu) | Product Ion Q3 Mass (amu) | Dwell Time (msec) | Collision Energy (V) |
|---|---|---|---|---|
| fosetyl-Al | 109 | 63 | 200 | -38 |
| phosphorous acid | 80.9 | 78.9 | 600 | -22 |

FIGURE 9

Proposed fragmentation pathway for fosetyl-Al m/z 109          m/z 63

Proposed fragmentation pathway for phosphorous acid m/z 81            m/z 79

Note : all recovery samples were also analysed using confirmatory transitions. The results are given in Appendix 3.

Table 4 : Standard concentrations prepared for the determination of detector linearity. The concentration corresponding to the LOQ is given in the second column of the table.

| HPLC-MS/MS | Standard Concentrations [µg/L] | | | | | |
|---|---|---|---|---|---|---|
| fosetyl-Al | 0.1 | 0.2 | 0.5 | 1 | 2 | 5 |
| phosphorous acid | 1 | 2 | 5 | 10 | 20 | 50 |

FIGURE 12

Table 5: Standard concentrations used for wheat samples and prepared for the determination of detector linearity. The concentration corresponding to the LOQ is given in the second column of the table.

| HPLC-MS/MS | Standard Concentrations [µg/L] | | | | | | |
|---|---|---|---|---|---|---|---|
| fosetyl-Al | 0.31 | 0.5 | 0.83 | 1 | 2.5 | 5 | 8.3 |
| phosphorous acid | 3.1 | 5 | 8.3 | 10 | 25 | 50 | 83 |

FIGURE 13

Table 6: Origin of untreated control samples

| Sample Material | Origin |
|---|---|
| Grape (whole fruit) | Mr Lusson – Angers - France |
| Orange (whole fruit) | Market specialised in organic food - France |
| Lettuce (head) | Market specialised in organic food - France |
| Cucumber (whole fruit) | Market specialised in organic food - France |
| Avocado (whole fruit) | Control sample from Bayer CropScience – Monheim - Germany |
| Wheat (Grain) | Control sample from Bayer CropScience – Monheim - Germany |

FIGURE 14

Table 7: Apparent residues in untreated control samples for fosetyl-Al and phosphorous acid

| Sample Material | Control Sample | LOQ [mg/kg] | | Apparent residues [mg/kg] | |
|---|---|---|---|---|---|
| | | fosetyl-Al | phosphorous acid | fosetyl-Al | Phosphorous acid |
| Grape (whole fruit) | Mr Lusson – Angers - FRANCE | 0.01 | 0.1 | < 0.003 | < 0.03 |
| Orange (whole fruit) | Market specialised in organic food - France | 0.01 | 0.1 | < 0.003 | < 0.03 |
| Lettuce (head) | Market specialised in organic food - France | 0.01 | 0.1 | < 0.003 | < 0.03 |
| Cucumber (whole fruit) | Market specialised in organic food - France | 0.01 | 0.1 | < 0.003 | < 0.03 |
| Avocado (whole fruit) | Control sample from Bayer CropScience – Monheim - Germany | 0.01 | 0.1 | < 0.003 | < 0.03 |
| Wheat (Grain) | Control sample from Bayer CropScience – Monheim - Germany | 0.01 | 0.1 | < 0.003 | < 0.03 |

FIGURE 15

Table 8 : Summary of the determination of detector linearity for LC/MS/MS.

| Detection | Parameter | fosetyl-Al | phosphorous acid |
|---|---|---|---|
| LC/MS/MS | Linear range [µg/L] | 0.1 – 5 (or 0.31 – 8.3 for wheat) | 1 – 50 (or 3.1 – 83 for wheat) |
| | No. of concentrations | 6 (or 7 for wheat) | 6 (or 7 for wheat) |
| | No. of injections | 1 | 1 |
| | Model | 1/x weighted linear regression | 1/x weighted linear regression |
| | Correlation coefficient (R) for standards prepared in solvent | > 0.9990 | > 0.9900 |
| | Correlation coefficient (R) for matrix matched standards | > 0.9990 | > 0.9985 |

FIGURE 16

Table 9: Matrix effect evaluation for fosetyl-Al
FL : Fortification Level

| Sample Material | FL [mg/kg] | Number of Values (n) | Measurement using | | | |
|---|---|---|---|---|---|---|
| | | | Standards in pure solvent | | Matrix matched standards | |
| | | | Mean [%] | RSD [%] | Mean [%] | RSD [%] |
| Grape (whole fruit) | 0.01 | 5 | 100 | 3.1 | 100 | 2.9 |
| | 0.10 | 5 | 102 | 0.9 | 101 | 0.9 |
| Orange (whole fruit) | 0.01 | 5 | 90 | 6.3 | 97 | 6.0 |
| | 0.10 | 5 | 90 | 4.6 | 92 | 4.5 |
| Lettuce (head) | 0.01 | 5 | 108 | 6.1 | 108 | 6.2 |
| | 0.10 | 5 | 105 | 1.7 | 105 | 2.1 |
| Cucumber (whole fruit) | 0.01 | 5 | 97 | 2.1 | 96 | 1.6 |
| | 0.10 | 5 | 98 | 2.3 | 101 | 2.7 |

FIGURE 17

Table 10: Matrix effect evaluation for phosphorous acid
FL : Fortification Level

| Sample Material | FL [mg/kg] | Number of Values (n) | Measurement using | | | |
|---|---|---|---|---|---|---|
| | | | Standards in pure solvent | | Matrix matched standards | |
| | | | Mean [%] | RSD [%] | Mean [%] | RSD [%] |
| Grape (whole fruit) | 0.1 | 5 | 156 | 6.7 | 99 | 8.5 |
| | 1 | 5 | 131 | 1.9 | 102 | 2.1 |
| Orange (whole fruit) | 0.1 | 5 | 189 | 10.6 | 76 | 18.3 |
| | 1 | 5 | 147 | 2.5 | 98 | 2.3 |
| Lettuce (head) | 0.1 | 5 | 193 | 6.4 | 81 | 9.7 |
| | 1 | 5 | 160 | 3.8 | 104 | 3.9 |
| Cucumber (whole fruit) | 0.1 | 5 | 185 | 4.7 | 87 | 7.0 |
| | 1 | 5 | 135 | 2.6 | 100 | 2.2 |
| Avocado (whole fruit) | 0.1 | 5 | 139 | 3.7 | 73 | 5.1 |
| | 1 | 5 | 132 | 6.8 | 100 | 6.7 |
| Wheat (Grain) | 0.1 | 5 | 152 | 8.3 | 98 | 5.8 |
| | 1 | 5 | 163 | 2.6 | 79 | 2.5 |

FIGURE 18

Table 11: Recovery rates obtained for fosetyl-Al, FL: fortification level, RSD: relative standard deviation

| Crop | Sample Material | FL [mg/kg] | Recovery of fosetyl-Al | | | | |
|---|---|---|---|---|---|---|---|
| | | | Single Values [%] | | | Mean [%] | RSD [%] |
| Grape | Whole fruit | 0.01 | 102 | 102 | 95 | 100 | 2.9 |
| | | | 101 | 100 | | | |
| | | 0.1 | 101 | 102 | 102 | 101 | 0.9 |
| | | | 102 | 100 | | | |
| | | | Overall Mean and RSD | | | 101 | 2.1 |
| Orange | Whole fruit | 0.01 | 102 | 100 | 98 | 97 | 6.0 |
| | | | 87 | 97 | | | |
| | | 0.1 | 96 | 95 | 94 | 92 | 4.5 |
| | | | 90 | 86 | | | |
| | | | Overall Mean and RSD | | | 95 | 5.6 |
| Lettuce | Head | 0.01 | 104 | 98 | 109 | 108 | 6.2 |
| | | | 113 | 114 | | | |
| | | 0.1 | 102 | 106 | 104 | 105 | 2.1 |
| | | | 107 | 107 | | | |
| | | | Overall Mean and RSD | | | 106 | 4.5 |
| Cucumber | Whole fruit | 0.01 | 95 | 96 | 98 | 96 | 1.6 |
| | | | 98 | 95 | | | |
| | | 0.1 | 106 | 101 | 101 | 101 | 2.7 |
| | | | 99 | 100 | | | |
| | | | Overall Mean and RSD | | | 99 | 3.4 |
| Avocado | Whole fruit | 0.01 | 104 | 95 | 92 | 96 | 5.0 |
| | | | 94 | 93 | | | |
| | | 0.1 | 88 | 88 | 85 | 87 | 1.9 |
| | | | 89 | 86 | | | |
| | | | Overall Mean and RSD | | | 91 | 6.1 |
| Wheat | Grain | 0.01 | 86 | 92 | 93 | 88 | 5.4 |
| | | | 85 | 82 | | | |
| | | 0.1 | 75 | 79 | 69 | 73 | 5.5 |
| | | | 71 | 71 | | | |
| | | | Overall Mean and RSD | | | 80 | 10.9 |

FIGURE 19

Table 12: Recovery rates obtained for Phosphorous acid, FL: fortification level, RSD: relative standard deviation

| Crop | Sample Material | FL [mg/kg] | Recovery of Phosphorous acid Single Values [%] | | | Mean [%] | RSD [%] |
|---|---|---|---|---|---|---|---|
| Grape | Whole fruit | 0.1 | 96 | 94 | 113 | 99 | 8.5 |
| | | | 100 | 92 | | | |
| | | 1 | 100 | 105 | 104 | 102 | 2.1 |
| | | | 101 | 101 | | | |
| | | | Overall Mean and RSD | | | 101 | 6.0 |
| Orange | Whole fruit | 0.1 | 65 | 99 | 70 | 76 | 18.3 |
| | | | 78 | 67 | | | |
| | | 1 | 97 | 99 | 101 | 98 | 2.3 |
| | | | 95 | 99 | | | |
| | | | Overall Mean and RSD | | | 87 | 17.3 |
| Lettuce | Head | 0.1 | 82 | 94 | 76 | 81 | 9.7 |
| | | | 79 | 74 | | | |
| | | 1 | 103 | 108 | 98 | 104 | 3.9 |
| | | | 106 | 107 | | | |
| | | | Overall Mean and RSD | | | 93 | 14.7 |
| Cucumber | Whole fruit | 0.1 | 83 | 82 | 82 | 87 | 7.0 |
| | | | 91 | 95 | | | |
| | | 1 | 102 | 102 | 101 | 100 | 2.2 |
| | | | 97 | 99 | | | |
| | | | Overall Mean and RSD | | | 93 | 8.9 |
| Avocado | Whole fruit | 0.1 | 74 | 77 | 68 | 73 | 5.1 |
| | | | 70 | 75 | | | |
| | | 1 | 110 | 97 | 92 | 100 | 6.7 |
| | | | 103 | 100 | | | |
| | | | Overall Mean and RSD | | | 87 | 17.8 |
| Wheat | Grain | 0.1 | 90 | 94 | 101 | 98 | 5.8 |
| | | | 102 | 103 | | | |
| | | 1 | 77 | 77 | 81 | 79 | 2.5 |
| | | | 79 | 81 | | | |
| | | | Overall Mean and RSD | | | 89 | 12.2 |

FIGURE 20

Table 13: Summary of the recovery data for the determination of accuracy and repeatability; RSD: relative standard deviation

|  | Parameter | fosetyl-Al | Phosphorous acid |
|---|---|---|---|
| Accuracy | Single recoveries [%] | 69 - 114 | 65 - 113 |
|  | Mean recoveries per fortification level [%] | 93 - 97 | 86 - 97 |
|  | Mean recoveries per sample material [%] | 80 - 106 | 87 - 101 |
|  | Overall mean [%] | 95 | 91 |
|  | Number of values n | 60 | 60 |
| Repeatability | RSD per fortification level [%] | 7.6 – 12.3 | 9.5 – 14.9 |
|  | RSD per sample material [%] | 2.1 – 10.9 | 6.0 – 17.8 |
|  | Overall RSD [%] | 10.2 | 13.7 |

FIGURE 21

Table 14: Stability period of final extracts in the auto sampler rack at about 10°C

| Sample Material | Stability period (days) |
|---|---|
| Grape (whole fruit) | 7 days |
| Orange (whole fruit) | 4 days |
| Lettuce (head) | 8 days |
| Cucumber (whole fruit) | 8 days |
| Avocado (whole fruit) | 4 days |
| Wheat (Grain) | 3 days |

FIGURE 22

Appendix 1
Flow Diagram of Residue Method 00861/M001

| Extraction |
|---|

1. Weigh 20.0 g of homogeneous sample material into a 125 mL polypropylene bottle.
2. Add 80 mL of acetonitrile / water (50/50, v/v).
3. Blend the sample using a high-speed blender (IKA or equivalent) for approx. 5 minutes.
4. Centrifuge the extract (3600 rpm – 5°C) for approx. 5 minutes.
5. Pour the supernatant into a 200 mL volumetric flask.
6. Add 80 mL of acetonitrile / water (50/50, v/v) on the bottom.
7. Blend the sample using a high-speed blender (IKA or equivalent) for approx. 5 minutes.
8. Centrifuge the extract (3600 rpm – 5°C) for approx. 5 minutes.
9. Pour the supernatant into the volumetric flask.
10. Make-up to 200 mL with methanol. This is the Extract A.
11. Centrifuge an aliquot of about 10 mL of Extract A (6000 rpm – ambient) for approx. 10 minutes.
12. Filter the extract through an Acrodisc CR 25 mm PTFE filter (0.45 μm).
13. Dilute five times the extract using acidified methanol with formic acid 0.5 %. This is the Final Extract.

Remark : for wheat samples, from stage 10, follow the preparation as described below :

10. Add 1 mL of concentrated formic acid and make-up to 200 mL with methanol. This is the Extract A.
11. Centrifuge an aliquot of about 10 mL of Extract A (6000 rpm – ambient) for approx. 10 minutes.
12. With dilutor, dilute twice the supernatant using acidified methanol with formic acid 0.5 %.
13. Filter the extract through an Acrodisc CR 25 mm PTFE filter (0.45 μm). This is the Final Extract.

FIGURE 23(a)

| HPLC Measurement with Electrospray MS/MS detection |

<u>Appendix 2</u>
Details on LC-MS/MS conditions

Comment:
Synchronization Mode: LC Sync
Auto-Equilibration: Off
Acquisition Duration: 11min59sec
Number Of Scans: 888
Periods In File: 1
Acquisition Module: Acquisition Method
Software version Analyst 1.4

MS Method Properties:

Period 1:
----------------

Scans in Period: 888
Relative Start Time: 0.00 msec
Experiments in Period: 1

Period 1 Experiment 1:
---------------------------
Scan Type: MRM (MRM)
Polarity: Negative
Scan Mode: N/A
Ion Source: Turbo Spray
Resolution Q1: Unit
Resolution Q3: Unit
Intensity Thres.: 0.00 cps
Settling Time: 0.0000 msec
MR Pause: 5.0070 msec
MCA: No
Step Size: 0.00 amu <u>Quantifier transitions:</u>

| Q1 Mass (amu) | Q3 Mass (amu) | Dwell(msec) | Param | Start | Stop |
|---|---|---|---|---|---|
| 80.90 | 62.90 | 600.00 | DP | -55.00 | -55.00 |
| (phosphorous acid) | | | CE | -38.00 | -38.00 |

| Q1 Mass (amu) | Q3 Mass (amu) | Dwell(msec) | Param | Start | Stop |
|---|---|---|---|---|---|
| 109.00 | 80.90 | 200.00 | DP | -45.00 | -45.00 |
| (fosetyl-Al) | | | CE | -16.00 | -16.00 |

FIGURE 23(b)

Parameter Table (Period 1 Experiment 1):
CUR:   20.00
GS1:   40.00
GS2:   60.00
IS:    -4500.00
TEM:   600.00
ihe:   ON

CAD:   6.00
EP     -10.00
CXP    -1.00

Confirmatory transitions:

| Q1 Mass (amu) | Q3 Mass (amu) | Dwell(msec) | Param | Start | Stop |
|---|---|---|---|---|---|
| 80.90 | 78.90 | 600.00 | DP | -55.00 | -55.00 |
| (phosphorous acid) | | | CE | -22.00 | -22.00 |

| Q1 Mass (amu) | Q3 Mass (amu) | Dwell(msec) | Param | Start | Stop |
|---|---|---|---|---|---|
| 109.00 | 63.00 | 200.00 | DP | -45.00 | -45.00 |
| (fosetyl-Al) | | | CE | -38.00 | -38.00 |

Parameter Table (Period 1 Experiment 1):
CUR:   20.00
GS1:   40.00
GS2:   60.00
IS:    -4500.00
TEM:   600.00
ihe:   ON
CAD:   6.00
EP     -10.00
CXP    -5.00

Agilent 1100 LC Pump Method Properties :

Pump Model:   Agilent 1100 LC Binary Pump
Minimum Pressure (psi):     0.0
Maximum Pressure (psi):     5801.0
Dead Volume (μl):    40.0
Maximum Flow Ramp (ml/min²): 100.0
Maximum Pressure Ramp (psi/sec):   290.0
Step Table:

| Step | Total Time(min) | Flow Rate(μl/min) | A (%) | B (%) |
|---|---|---|---|---|
| 0 | 0.00 | 400 | 65.0 | 35.0 |
| 1 | 10.00 | 400 | 65.0 | 35.0 |

Left Compressibility:    50.0
Right Compressibility:   115.0
Left Dead Volume (μl):   40.0
Right Dead Volume (μl):  40.0
Left Stroke Volume (μl): -1.0
Right Stroke Volume (μl):    -1.0
Left Solvent:   A2 (water + 0.5% formic acid)
Right Solvent:  B2 (methanol)

FIGURE 23(b) (continued)

CTC PAL Auto sampler Method Properties :

| Field | Value |
|---|---|
| Loop Volume1 (μl): | 100 |
| Loop Volume2 (μl): | 20 |
| Injection Volume (μl): | 50.000 |

Method Description:
    Syringe: 250ul
    Analyst LC-Inj

| Parameter | Value |
|---|---|
| Air Volume (μl) | 0 |
| Pre Clean with Solvent 1 () | 2 |
| Pre Clean with Solvent 2 () | 1 |
| Pre Clean with Sample () | 0 |
| Filling Speed (μl/s) | 50 |
| Filling Strokes () | 0 |
| Inject to | LC Vlv2 |
| Injection Speed (μl/s) | 50 |
| Pre Inject Delay (ms) | 500 |
| Post Inject Delay (ms) | 500 |
| Post Clean with Solvent 1 () | 3 |
| Post Clean with Solvent 2 () | 2 |
| Valve Clean with Solvent 1 () | 2 |
| Valve Clean with Solvent 2 () | 1 |

Agilent 1100 LC Pump Method Properties :

Pump Model: Agilent 1100 LC Quaternary Pump
Minimum Pressure (psi): 0.0
Maximum Pressure (psi): 5801.0
Compressibility: 100.0
Dead Volume (μl): 40.0
Stroke Volume (μl): -1.0
Maximum Flow Ramp (ml/min$^2$): 100.0
Maximum Pressure Ramp (psi/sec): 290.0

Step Table:

| Step | Total Time (min) | Flow Rate (μl/min) | A (%) | B (%) | C (%) | D (%) | TE#1 (water) | TE#2 (methanol) | TE#3 | TE#4 |
|---|---|---|---|---|---|---|---|---|---|---|
| 0 | 0.00 | 200 | 50.0 | 50.0 | 0.0 | 0.0 | open | open | open | open |
| 1 | 10.00 | 200 | 50.0 | 50.0 | 0.0 | 0.0 | open | open | open | open |

Primary Flow Rate (ul/min): 200.0
Flow Sensor Calibration Table Index: 0

Valco Valve Method Properties
Valco Valve    Diverter
    Total Time (min)    Position

| | | | |
|---|---|---|---|
| 1 | 0.0 | B | waste |
| 2 | 3.0 | A | spectro |

FIGURE 23(b) (continued)

| Gas pressure | | Auto sampler CTC Analytics HTS Pal (n° 1303 ) | |
|---|---|---|---|
| N2 | 4 bar | Peltier rack | 10 °C |
| Air gas | 7.5 bar | Loop | 20 µL |
| Air Exhaust gas | 4 bar | Solvent 1 | $H_2O$ + 0.5 % HCOOH |
| | | Solvent 2 | MeOH |
| | | | |
| | | Oven Agilent G1316A (n°1294 ) | |
| | | Temperature | Not used |
| | | | |
| | | | |
| | | Valco valve | Column selector |
| | | C2-0000EP V1C1 (n°1289) | C5-0006EMTD (n° 1290) |
| | | Ten ports | 6 positions |
| | | 2 positions | Not used |
| | | A = MS  B = Waste | |
| Pumps | | Source n° 1291 | Probe TurboIonSpray |
| Binary pump Agilent 1100 G1312A (n° 1297) | 133 bar | | n° 1288 |
| Flow | 0.4 mL/min | Horizontal Position | 7 (x axis) |
| A2 = $H_2O$+ 0.5% Formic Acid | 65 % | Vertical Position | 7 (y axis) |
| B2 = MeOH | 35 % | Capillary exit | 1 mm |
| Isocratic | | | |
| | | Mass Spectrometer API 4000 | |
| | | Device GLP n° 1292 | |
| Quaternary pump Agilent 1100 G1354A (n° 1298) | | | |
| Flow | 0.2mL/min | Column | |
| A = $H_2O$ | 50 % | Precolumn | SMPREA1 |
| B = MeOH | 50 % | Column | SMAR 69-1 |
| C = | - | Thermo Hypercarb 100 x 3.0mm 5µm | |
| D = | - | (ambient temperature) | |
| Isocratic mode | | | |

FIGURE 23(c)

Appendix 3
Results obtained with confirmatory transitions

| Crop | Sample Material | FL [mg/kg] | Recovery of fosetyl-Al | | | Mean [%] | RSD [%] |
|------|-----------------|------------|---|---|---|----------|---------|
|      |                 |            | Single Values [%] | | | | |
| Grape | Whole fruit | 0.01 | 101 | 107 | 106 | 100 | 8.8 |
|       |             |      | 101 | 85  |     |     |     |
|       |             | 0.1  | 98  | 102 | 93  | 99  | 4.5 |
|       |             |      | 96  | 104 |     |     |     |
|       |             |      | Overall Mean and RSD | | | 99 | 6.7 |
| Orange | Whole fruit | 0.01 | 121 | 121 | 110 | 110 | 10.3 |
|        |             |      | 106 | 94  |     |     |     |
|        |             | 0.1  | 98  | 102 | 91  | 94  | 7.0 |
|        |             |      | 92  | 85  |     |     |     |
|        |             |      | Overall Mean and RSD | | | 102 | 12.2 |
| Lettuce | Head | 0.01 | 113 | 102 | 90 | 97 | 10.9 |
|         |      |      | 93  | 87  |    |    |     |
|         |      | 0.1  | 95  | 97  | 96 | 96 | 1.4 |
|         |      |      | 95  | 98  |    |    |     |
|         |      |      | Overall Mean and RSD | | | 97 | 7.4 |
| Cucumber | Whole fruit | 0.01 | 117 | 117 | 107 | 110 | 6.0 |
|          |             |      | 103 | 106 |     |     |     |
|          |             | 0.1  | 100 | 100 | 102 | 100 | 1.4 |
|          |             |      | 98  | 100 |     |     |     |
|          |             |      | Overall Mean and RSD | | | 105 | 6.6 |
| Avocado | Whole fruit | 0.01 | 93 | 94 | 91 | 92 | 4.9 |
|         |             |      | 97 | 85 |    |    |     |
|         |             | 0.1  | 85 | 87 | 85 | 85 | 1.4 |
|         |             |      | 84 | 84 |    |    |     |
|         |             |      | Overall Mean and RSD | | | 89 | 5.4 |
| Wheat | Grain | 0.01 | 83 | 88 | 98 | 89 | 7.3 |
|       |       |      | 86 |    |    |    |     |
|       |       | 0.1  | 72 | 81 | 73 | 75 | 5.2 |
|       |       |      | 72 | 77 |    |    |     |

FIGURE 23(d)

| | | | Overall Mean and RSD | | 81 | 10.8 |
|---|---|---|---|---|---|---|
| Grape | Whole fruit | 0.1 | 91 86 96 87 | 119 | 96 | 14.1 |
| | | 1 | 99 101 100 102 | 98 | 100 | 1.6 |
| | | | Overall Mean and RSD | | 98 | 9.6 |
| Orange | Whole fruit | 0.1 | 69 92 71 68 | 68 | 74 | 14.1 |
| | | 1 | 108 106 97 101 | 106 | 104 | 4.3 |
| | | | Overall Mean and RSD | | 89 | 19.8 |
| Lettuce | Head | 0.1 | 91 80 70 69 | 94 | 81 | 14.3 |
| | | 1 | 103 105 101 100 | 101 | 102 | 2.0 |
| | | | Overall Mean and RSD | | 91 | 14.9 |
| Cucumber | Whole fruit | 0.1 | 90 93 77 94 | 77 | 86 | 9.9 |
| | | 1 | 101 100 95 99 | 101 | 99 | 2.5 |
| | | | Overall Mean and RSD | | 93 | 9.8 |
| Avocado | Whole fruit | 0.1 | 71 81 70 76 | 84 | 76 | 8.0 |
| | | 1 | 113 107 100 99 | 103 | 104 | 5.5 |
| | | | Overall Mean and RSD | | 90 | 17.5 |
| Wheat | Grain | 0.1 | 74 74 74 71 | 77 | 74 | 2.9 |
| | | 1 | 75 82 83 80 | 78 | 80 | 4.0 |
| | | | Overall Mean and RSD | | 77 | 5.1 |

FL : Fortification Level

FIGURE 23(d) (continued)

Table 15: LOQ and principle of analytical determination

| Compound | | fosetyl-Al | Phosphorous acid |
|---|---|---|---|
| Determined as | | fosetyl-Al | Phosphorous acid |
| Calculated as | | fosetyl-Al | Phosphorous acid |
| Principle of Determination | | LC/MS/MS | LC/MS/MS |
| LOQ [mg/L] | Drinking water | 0.0001 | 0.0001 |
| | Surface water | 0.0001 | 0.0001 |

FIGURE 24

Table 16: Standard concentrations prepared for the determination of detector linearity. The concentration corresponding to the LOQ is printed in the third column of the table.

| HPLC-MS/MS | Standard Concentrations [µg/L] | | | | | | | | |
|---|---|---|---|---|---|---|---|---|---|
| fosetyl-Al | 0.2 | 0.4 | 0.5 | 0.75 | 1 | 2 | 5 | 10 | 20 |
| phosphorous acid | 0.2 | 0.4 | 0.5 | 0.75 | 1 | 2 | 5 | 10 | 20 |

FIGURE 25

Table 17: Origin of untreated control samples

| Test system | Origin |
|---|---|
| Drinking water | BCS - CRLD - Tap water from lab D221 – Lyon - France |
| Surface water | St Agnan en Vercors - France |

FIGURE 26

Table 18: Characteristics of surface water

| date of collect (yyyy/mm/dd) | pH at 16.5°C (NF T 90-008) | $Ca^{++}$ (mg/L) (potentiometric detection) | clay particles (mg/L) (NF EN 872) | total organic carbon (TOC) (mg/L) (NF EN 1484) | conductivity (µS/cm) (NF EN 27 888) |
|---|---|---|---|---|---|
| 2005/03/27 | 8.1 | 88 | < 2 | 1.00 | 400 |

These characteristics were determined by :
    Cemagref
    Division qualité des eaux et prévention des pollutions
    Groupement de Lyon
    3 bis quai Chauveau
    69336 Lyon cedex 09 - France

FIGURE 27

Table 19: Apparent residues in untreated control samples for fosetyl-Al and phosphorous acid

| Sample Material | Origin | LOQ [mg/L] | | Apparent residues [mg/L] | |
|---|---|---|---|---|---|
| | | fosetyl-Al | phosphorous acid | fosetyl-Al | phosphorous acid |
| Drinking water | BCS - CRLD - Tap water from lab D221 – Lyon - France | 0.0001 | 0.0001 | < 30% LOQ | < 30% LOQ |
| Surface water | St Agnan en Vercors - France | 0.0001 | 0.0001 | < 30% LOQ | < 30% LOQ |

FIGURE 28

Table 20: Recovery rate obtained for fosetyl-Al and phosphorous acid at 0.05 µg/L fortification level

| Sample Material | Fortification level [mg/L] | | Recovery [%] | |
|---|---|---|---|---|
| | fosetyl-Al | phosphorous acid | fosetyl-Al | phosphorous acid |
| Drinking water | 0.00005 | 0.00005 | 89 | 75 |
| Surface water | 0.00005 | 0.00005 | 106 | 95 |

FIGURE 29

Table 21: Summary of the determination of detector linearity for LC/MS/MS.

| Detection | Parameter | fosetyl-Al | phosphorous acid |
|---|---|---|---|
| LC/MS/MS | Linear range [µg/L] | 0.2 - 20 | 0.2 - 20 |
| | No. of concentrations | 9 | 9 |
| | No. of injections | 1 | 1 |
| | Model | 1/x weighted linear regression | 1/x weighted linear regression |
| | Correlation coefficient (R) for standards prepared in solvent | > 0.9993 | > 0.9991 |
| | Correlation coefficient (R) for matrix matched standards | > 0.9981 | > 0.9990 |

FIGURE 30

Table 22: Matrix effect evaluation for fosetyl-Al.

FL : Fortification Level

| Sample Material | FL [mg/L] | Number of Values (n) | Measurement using | | | |
|---|---|---|---|---|---|---|
| | | | Standards in pure solvent | | Matrix matched standards | |
| | | | Mean [%] | RSD [%] | Mean [%] | RSD [%] |
| Drinking water | 0.0001 | 5 | 25 | 17.0 | 86 | 12.2 |
| | 0.001 | 5 | 33 | 7.0 | 82 | 6.5 |
| Surface water | 0.0001 | 5 | 97 | 7.9 | 107 | 6.4 |
| | 0.001 | 5 | 103 | 3.4 | 96 | 3.3 |

FIGURE 31

Table 23: Matrix effect evaluation for phosphorous acid
FL : Fortification Level

| Sample Material | FL [mg/L] | Number of Values (n) | Measurement using | | | |
|---|---|---|---|---|---|---|
| | | | Standards in pure solvent | | Matrix matched standards | |
| | | | Mean [%] | RSD [%] | Mean [%] | RSD [%] |
| Drinking water | 0.0001 | 5 | 80 | 3.3 | 76 | 5.7 |
| | 0.001 | 5 | 64 | 11.3 | 88 | 11.9 |
| Surface water | 0.0001 | 5 | 123 | 4.2 | 109 | 4.1 |
| | 0.001 | 5 | 101 | 4.6 | 93 | 4.6 |

FIGURE 32

Table 24: Recovery rates obtained for fosetyl-Al, RSD: relative standard deviation

| Sample Material | Fortification Level [mg/L] | Recovery of fosetyl-Al | | | |
|---|---|---|---|---|---|
| | | Single Values [%] | | Mean [%] | RSD [%] |
| Drinking water | 0.0001 | 76  76  87 | | 86 | 12.2 |
| | | 90  101 | | | |
| | 0.001 | 78  75  87 | | 82 | 6.5 |
| | | 87  82 | | | |
| | | Overall Mean and RSD | | 84 | 9.7 |
| Surface water | 0.0001 | 100  103  107 | | 107 | 6.4 |
| | | 118  106 | | | |
| | 0.001 | 98  100  96 | | 96 | 3.3 |
| | | 92  94 | | | |
| | | Overall Mean and RSD | | 101 | 7.5 |

FIGURE 33

Table 25: Recovery rates obtained for Phosphorous acid, RSD: relative standard deviation

| Sample Material | Fortification Level [mg/L] | Recovery of Phosphorous acid | | | | |
|---|---|---|---|---|---|---|
| | | Single Values [%] | | | Mean [%] | RSD [%] |
| Drinking water | 0.0001 | 72 | 72 | 74 | 76 | 5.7 |
| | | 78 | 82 | | | |
| | 0.001 | 80 | 76 | 89 | 88 | 11.9 |
| | | 96 | 101 | | | |
| | | Overall Mean and RSD | | | 82 | 12.4 |
| Surface water | 0.0001 | 109 | 106 | 106 | 109 | 4.1 |
| | | 117 | 109 | | | |
| | 0.001 | 97 | 98 | 94 | 93 | 4.6 |
| | | 88 | 90 | | | |
| | | Overall Mean and RSD | | | 101 | 9.3 |

FIGURE 34

Table 26: Summary of the recovery data for the determination of accuracy and repeatability; RSD: relative standard deviation

|  | Parameter | fosetyl-Al | Phosphorous acid |
|---|---|---|---|
| Accuracy | Single recoveries [%] | 75 - 118 | 72 - 117 |
|  | Mean recoveries per fortification level [%] | 89 – 96 | 91 - 93 |
|  | Mean recoveries per sample material [%] | 84 - 101 | 82 - 101 |
|  | Overall mean [%] | 93 | 92 |
|  | Number of values n | 20 | 20 |
| Repeatability | RSD per fortification level [%] | 9.6 – 14.3 | 8.8 – 19.8 |
|  | RSD per sample material [%] | 7.5 – 9.7 | 9.3 – 12.4 |
|  | Overall RSD [%] | 12.7 | 15.0 |

FIGURE 35

Assessment of different LC conditions :

All recovery samples were also analysed using different LC conditions. The only modification was the mobile phase.

| LC conditions | Original | Substitute |
|---|---|---|
| Change in the mobile phase composition | Isocratic mode: 55 / 45 (v/v) methanol + 2% HCOOH / water + 2% HCOOH | Isocratic mode: 35 / 65 (v/v) methanol / water + 2% HCOOH |
| Retention times | from 3.1 to 4.1 min for phosphorous acid and 3.9 to 5.3 min for fosetyl-Al | about 3.2 min for phosphorous acid and 5.2 min for fosetyl-Al |

Complete original LC conditions are indicated in Error! Reference source not found..

FIGURE 36

Table 27: Summary of the results obtained with substitute LC conditions

| Test system | Compound | LC conditions | Calibration curve | |
|---|---|---|---|---|
| | | | Standards in pure solvent | Matrix matched standards |
| Drinking water | fosetyl-Al | original | (LOQ and 10LOQ) : No | (LOQ and 10LOQ) : OK |
| | | substitute | (LOQ and 10LOQ) : No | (LOQ and 10LOQ) : OK |
| | $H_3PO_3$ | original | LOQ : OK 10LOQ : No | (LOQ and 10LOQ) : OK |
| | | substitute | (LOQ and 10LOQ) : No | (LOQ and 10LOQ) : OK |
| Surface water | fosetyl-Al | original | (LOQ and 10LOQ) : OK | (LOQ and 10LOQ) : OK |
| | | substitute | (LOQ and 10LOQ) : No | (LOQ and 10LOQ) : No |
| | $H_3PO_3$ | original | LOQ : No 10LOQ : OK | (LOQ and 10LOQ) : OK |
| | | substitute | LOQ : No 10LOQ : OK | (LOQ and 10LOQ) : OK |

"OK" means that the results comply with European requirements.

"No" means that the results do not comply with European requirements.

The column "Standards in pure solvent" is given as information.

FIGURE 37

Table 28: Summary of the results obtained with variant method

| Test system | Compound | LC conditions | Calibration curve | |
|---|---|---|---|---|
| | | | Standards in pure solvent | Matrix matched standards |
| Drinking water | fosetyl-Al | original | (LOQ and 10LOQ) : OK | (LOQ and 10LOQ) : OK |
| | | substitute | (LOQ and 10LOQ) : No | (LOQ and 10LOQ) : OK |
| | $H_3PO_3$ | original | LOQ : No<br>10LOQ : OK | LOQ : No<br>10LOQ : OK |
| | | substitute | (LOQ and 10LOQ) : No | LOQ : No<br>10LOQ : OK |
| Surface water | fosetyl-Al | original | (LOQ and 10LOQ) : OK | (LOQ and 10LOQ) : OK |
| | | substitute | (LOQ and 10LOQ) : OK | (LOQ and 10LOQ) : OK |
| | $H_3PO_3$ | original | LOQ : No<br>10LOQ : OK | LOQ : No<br>10LOQ : OK |
| | | substitute | LOQ : No<br>10LOQ : OK | LOQ : No<br>10LOQ : OK |

"OK" means that the results comply with European requirements.

"No" means that the results do not comply with European requirements.

The column "Standards in pure solvent" is given as information.

FIGURE 38

Appendix 4
Flow Diagram of Residue Method 00931/M001

*Main point : for each set of samples, it is necessary to do a blank reagent where water sample is replaced by H2O milliQ to be sure that no H3PO3 contamination (< 30% LOQ) coming from sample preparation is found.*

*0.6 g of washed AG 50W-X8 resin*
*(in disposable Nalgene bottle PP)*
+
*20.0 g of water sample*
*(using disposable Pasteur Pipette)*
*(Add here using a dilutor 200 µL of the fortifying solution for LOQ recoveries or 200 µL of the fortifying solution for 10LOQ recoveries)*

*Mechanical agitation (10 minutes) at ambient temperature: corresponds to* Extract A

*Pour 5 mL of extract*
*(using a disposable glass pipette)*
*into a weighted disposable glass test tube*

*Evaporation at 60°C under a nitrogen flow to about 0.5 g*
CAUTION NOT TO GO TO DRYNESS

*Make-up to 1 g with water + formic acid 0.5%*
*(using disposable Pasteur Pipette)*

*Sonication :*
*correspond to* Final Extract

HPLC Measurement with Electrospray MS/MS detection

*If necessary to dilute the Final Extract due to concentration outside the calibration curve : use final extract of control sample*

(because matrix matched standards are used for calibration)

FIGURE 39

<u>Appendix 5</u>
Details on LC-MS/MS conditions

Comment:
Synchronization Mode: LC Sync
Auto-Equilibration: Off
Acquisition Duration: 10min1sec
Number Of Scans: 455
Periods In File: 1
Acquisition Module: Acquisition Method
Software version Analyst 1.4

MS Method Properties:

Period 1:
---------------

Scans in Period: 455
Relative Start Time: 0.00 msec
Experiments in Period: 1

Period 1 Experiment 1:
---------------------------

Scan Type: MRM (MRM)
Polarity: Negative
Scan Mode: N/A
Ion Source: Turbo Spray
Resolution Q1: Unit
Resolution Q3: Unit
Intensity Thres.: 0.00 cps
Settling Time: 0.0000 msec
MR Pause: 5.0070 msec
MCA: No
Step Size: 0.00 amu FIGURE 40(a)

Agilent 1100 LC Pump Method Properties :

Pump Model: Agilent 1100 LC Binary Pump
Minimum Pressure (psi): 0.0
Maximum Pressure (psi): 5801.0
Dead Volume (µl): 40.0
Maximum Flow Ramp (ml/min$^2$): 100.0
Maximum Pressure Ramp (psi/sec): 290.0
Step Table:

| Step | Total Time(min) | Flow Rate(µl/min) | A (%) | B (%) |
|---|---|---|---|---|
| 0 | 0.00 | 200 | 45.0 | 55.0 |
| 1 | 10.00 | 200 | 45.0 | 55.0 |

Left Compressibility: 50.0
Right Compressibility: 115.0
Left Dead Volume (µl): 40.0
Right Dead Volume (µl): 40.0
Left Stroke Volume (µl): -1.0
Right Stroke Volume (µl): -1.0
Left Solvent: A2 (water + 2% formic acid)
Right Solvent: B1 (methanol + 2% formic acid)

CTC PAL Auto sampler Method Properties :

Loop Volume1 (µl): 50
Loop Volume2 (µl): 50
Injection Volume (µl): 200.000
Method Description:
    Syringe: 250ul
    Analyst LC-Inj

| | |
|---|---|
| Air Volume (µl) | 0 |
| Pre Clean with Solvent 1 () | 2 |
| Pre Clean with Solvent 2 () | 1 |
| Pre Clean with Sample () | 0 |
| Filling Speed (µl/s) | 50 |
| Filling Strokes () | 0 |
| Inject to | LC Vlv1 |
| Injection Speed (µl/s) | 50 |
| Pre Inject Delay (ms) | 500 |
| Post Inject Delay (ms) | 500 |
| Post Clean with Solvent 1 () | 3 |
| Post Clean with Solvent 2 () | 2 |
| Valve Clean with Solvent 1 () | 2 |
| Valve Clean with Solvent 2 () | 1 |

FIGURE 40(a) (continued)

Quantifier transitions:

| Q1 Mass (amu) | Q3 Mass (amu) | Dwell(msec) | Param | Start | Stop |
|---|---|---|---|---|---|
| 80.90 (phosphorous acid) | 78.90 | 400.00 | DP | -55.00 | -55.00 |
| | | | CE | -22.00 | -22.00 |
| | | | CXP | -5.00 | -5.00 |

| Q1 Mass (amu) | Q3 Mass (amu) | Dwell(msec) | Param | Start | Stop |
|---|---|---|---|---|---|
| 108.90 (fosetyl-Al) | 80.90 | 200.00 | DP | -45.00 | -45.00 |
| | | | CE | -16.00 | -16.00 |
| | | | CXP | -1.00 | -1.00 |

Confirmatory transitions:

| Q1 Mass (amu) | Q3 Mass (amu) | Dwell(msec) | Param | Start | Stop |
|---|---|---|---|---|---|
| 80.90 (phosphorous acid) | 62.90 | 400.00 | DP | -55.00 | -55.00 |
| | | | CE | -38.00 | -38.00 |
| | | | CXP | -1.00 | -1.00 |

| Q1 Mass (amu) | Q3 Mass (amu) | Dwell(msec) | Param | Start | Stop |
|---|---|---|---|---|---|
| 108.90 (fosetyl-Al) | 62.90 | 300.00 | DP | -45.00 | -45.00 |
| | | | CE | -38.00 | -38.00 |
| | | | CXP | -5.00 | -5.00 |

Parameter Table (Period 1 Experiment 1):
CAD:   6.00
CUR:   20.00
GS1:   40.00
GS2:   60.00
TEM:   600.00
ihe:   ON
IS:    -4500.00
EP:    -10.00

FIGURE 40(a) (continued)

| Gas pressure | | Auto sampler CTC Analytics HTS Pal (n° 1303 ) | |
|---|---|---|---|
| N2 | 4 bar | Peltier rack | 10 °C |
| Air gas | 7.5 bar | Loop | 50 µL |
| Air Exhaust gas | 4 bar | Solvent 1 | $H_2O$ + 0.5% HCOOH |
| | | Solvent 2 | MeOH |
| | | Oven Agilent G1316A (n°1294 ) | |
| | | Temperature | Not used |
| | | Valco valve | Column selector |
| | | C2-0000EP V1C1 (n°1289) | C5-0006EMTD (n° 1290) |
| | | Ten ports | 6 positions |
| | | 2 positions | Not used |
| | | Not used | |
| Pumps | | Source N° 1291 | Probe TurbolonSpray |
| Binary pump Agilent 1100 G1312A (n° 1297) | 1400 psi | | n° 1288 |
| Flow | 0.2 mL/min | Horizontal Position | 7 (x axis) |
| A2= $H_2O$ + 2% Formic Acid | 45 % | Vertical Position | 7 (y axis) |
| B1= MeOH + 2% Formic Acid | 55 % | Capillary exit | 1 mm |
| Isocratic | | | |
| | | Mass Spectrometer API 4000 | |
| | | Device GLP n° 1292 | |
| Binary pump Agilent 1100 G1312A (n° 1296) | Not used | | |
| Flow | - | Column | |
| A = | - | Precolumn | None |
| B = | - | Column | SMAR 68-1 |
| Isocratic mode | | Thermo Hypercarb 100 x 2.0mm 5µm | |
| | | (ambient temperature) | |

FIGURE 40(b)

Appendix 6
Results obtained with confirmatory transitions

| Sample Material | Compound | Fortification Level [mg/L] | Recovery | | | | |
|---|---|---|---|---|---|---|---|
| | | | Single Values [%] | | | Mean [%] | RSD [%] |
| Drinking water | fosetyl-Al | 0.0001 | 77 | 75 | 81 | 85 | 12.8 |
| | | | 91 | 101 | | | |
| | | 0.001 | 78 | 73 | 86 | 80 | 6.7 |
| | | | 85 | 79 | | | |
| | | Overall Mean and RSD | | | | 83 | 10.2 |
| | phosphorous acid | 0.0001 | 62 | 67 | 86 | 79 | 16.6 |
| | | | 89 | 89 | | | |
| | | 0.001 | 78 | 77 | 84 | 86 | 11.0 |
| | | | 94 | 98 | | | |
| | | Overall Mean and RSD | | | | 82 | 13.9 |
| Surface water | fosetyl-Al | 0.0001 | 96 | 101 | 106 | 107 | 9.4 |
| | | | 122 | 112 | | | |
| | | 0.001 | 99 | 100 | 96 | 97 | 2.9 |
| | | | 94 | 94 | | | |
| | | Overall Mean and RSD | | | | 102 | 8.8 |
| | phosphorous acid | 0.0001 | 116 | 108 | 104 | 109 | 4.0 |
| | | | 109 | 108 | | | |
| | | 0.001 | 100 | 96 | 93 | 93 | 5.6 |
| | | | 88 | 88 | | | |
| | | Overall Mean and RSD | | | | 101 | 9.5 |

FIGURE 41

Appendix 7
Results obtained with substitute LC conditions

Dinking water

| Calibration curve | Compound | Fortification Level [mg/L] | Recoveries | | | Mean [%] | RSD [%] |
|---|---|---|---|---|---|---|---|
| | | | Single Values [%] | | | | |
| standards in pure solvent | fosetyl-Al | 0.0001 | 10 | 10 | 9 | 9 | 9.1 |
| | | | 9 | 8 | | | |
| | | 0.001 | 18 | 18 | 17 | 18 | 4.7 |
| | | | 17 | 19 | | | |
| | | | Overall Mean and RSD | | | 14 | 34.1 |
| | phosphorous acid | 0.0001 | 35 | 35 | 37 | 36 | 4.6 |
| | | | 38 | 34 | | | |
| | | 0.001 | 29 | 28 | 33 | 30 | 6.2 |
| | | | 30 | 30 | | | |
| | | | Overall Mean and RSD | | | 33 | 10.6 |
| matrix matched standards | fosetyl-Al | 0.0001 | 95 | 94 | 85 | 89 | 6.3 |
| | | | 88 | 82 | | | |
| | | 0.001 | 96 | 97 | 94 | 97 | 4.0 |
| | | | 93 | 103 | | | |
| | | | Overall Mean and RSD | | | 93 | 6.6 |
| | phosphorous acid | 0.0001 | 93 | 94 | 98 | 96 | 4.6 |
| | | | 102 | 91 | | | |
| | | 0.001 | 85 | 81 | 95 | 87 | 5.9 |
| | | | 86 | 86 | | | |
| | | | Overall Mean and RSD | | | 91 | 7.2 |

FIGURE 42(a)

Surface water

| Calibration curve | Compound | Fortification Level [mg/L] | Recoveries Single Values [%] | | | Mean [%] | RSD [%] |
|---|---|---|---|---|---|---|---|
| standards in pure solvent | fosetyl-Al | 0.0001 | 26 | 26 | 30 | 30 | 17.5 |
| | | | 31 | 39 | | | |
| | | 0.001 | 45 | 59 | 71 | 59 | 15.7 |
| | | | 60 | 59 | | | |
| | | | Overall Mean and RSD | | | 45 | 37.1 |
| | phosphorous acid | 0.0001 | 51 | 63 | 64 | 60 | 9.2 |
| | | | 59 | 64 | | | |
| | | 0.001 | 69 | 73 | 71 | 70 | 3.5 |
| | | | 67 | 68 | | | |
| | | | Overall Mean and RSD | | | 65 | 9.8 |
| matrix matched standards | fosetyl-Al | 0.0001 | 103 | 102 | 111 | 112 | 10.1 |
| | | | 113 | 130 | | | |
| | | 0.001 | 98 | 127 | 151 | 126 | 14.9 |
| | | | 128 | 126 | | | |
| | | | Overall Mean and RSD | | | 119 | 13.8 |
| | phosphorous acid | 0.0001 | 89 | 106 | 109 | 103 | 8.2 |
| | | | 101 | 109 | | | |
| | | 0.001 | 105 | 110 | 108 | 105 | 3.6 |
| | | | 101 | 102 | | | |
| | | | Overall Mean and RSD | | | 104 | 6.0 |

FIGURE 42(b)

Appendix 8
Flow chart of variant method

Main point : *for each set of samples, it is necessary to do a blank reagent where water sample is replaced by H2O milliQ to be sure that no H3PO3 contamination (< 30% LOQ) coming from sample preparation is found.*

0.6 g of washed AG 50W-X8 resin
(in disposable Nalgene bottle PP)
+
20.0 g of water sample
(using disposable Pasteur Pipette)
*(Add here using a dilutor 200 µL of the fortifying solution for LOQ recoveries or 200 µL of the fortifying solution for 10LOQ recoveries)*

Mechanical agitation (10 minutes) at ambient temperature :
Extract A corresponds to Final Extract

HPLC Measurement with Electrospray MS/MS detection

*If necessary to dilute the Final Extract due to concentration outside the calibration curve : use final extract of control sample*

(because matrix matched standards are used for calibration)

FIGURE 43

Appendix 9

Results obtained with variant method

Drinking water

| Calibration curve | Compound | Fortification Level [mg/L] | Recoveries | | | Mean [%] | RSD [%] |
|---|---|---|---|---|---|---|---|
| | | | Single Values [%] | | | | |
| standards in pure solvent | fosetyl-Al | 0.0001 | 99 | 97 | 99 | 97 | 2.1 |
| | | | 98 | 94 | | | |
| | | 0.001 | 101 | 98 | 91 | 96 | 3.9 |
| | | | 95 | 95 | | | |
| | | Overall Mean and RSD | | | | 97 | 3.0 |
| | phosphorous acid | 0.0001 | no result | | | | |
| | | 0.001 | 105 | 100 | 101 | 101 | 2.0 |
| | | | 101 | 100 | | | |
| | | Overall Mean and RSD | | | | 101 | 2.0 |
| matrix matched standards | fosetyl-Al | 0.0001 | 106 | 104 | 106 | 104 | 2.0 |
| | | | 105 | 101 | | | |
| | | 0.001 | 101 | 98 | 92 | 96 | 3.5 |
| | | | 95 | 96 | | | |
| | | Overall Mean and RSD | | | | 100 | 5.0 |
| | phosphorous acid | 0.0001 | no result | | | | |
| | | 0.001 | 98 | 92 | 93 | 94 | 2.7 |
| | | | 93 | 92 | | | |
| | | Overall Mean and RSD | | | | 94 | 2.7 |

FIGURE 44(a)

Surface water

| Calibration curve | Compound | Fortification Level [mg/L] | Recoveries | | | Mean [%] | RSD [%] |
|---|---|---|---|---|---|---|---|
| | | | Single Values [%] | | | | |
| standards in pure solvent | fosetyl-Al | 0.0001 | 103 | 87 | 101 | 97 | 7.9 |
| | | | 103 | 90 | | | |
| | | 0.001 | 101 | 102 | 98 | 101 | 1.7 |
| | | | 102 | 100 | | | |
| | | | Overall Mean and RSD | | | 99 | 5.7 |
| | phosphorous acid | 0.0001 | no result | | | | |
| | | 0.001 | 97 | 97 | 94 | 97 | 2.1 |
| | | | 99 | 99 | | | |
| | | | Overall Mean and RSD | | | 97 | 2.1 |
| matrix matched standards | fosetyl-Al | 0.0001 | 104 | 88 | 102 | 98 | 7.9 |
| | | | 104 | 91 | | | |
| | | 0.001 | 101 | 101 | 98 | 100 | 1.6 |
| | | | 102 | 99 | | | |
| | | | Overall Mean and RSD | | | 99 | 5.4 |
| | phosphorous acid | 0.0001 | no result | | | | |
| | | 0.001 | 93 | 93 | 90 | 93 | 2.2 |
| | | | 95 | 95 | | | |
| | | | Overall Mean and RSD | | | 93 | 2.2 |

FIGURE 44(b)

Table 29: LOQ and principle of analytical determination

| Compound | Fosetyl-Al | Phosphorous acid |
|---|---|---|
| Determined as | Fosetyl-Al | Phosphorous acid |
| Calculated as | Fosetyl-Al | Phosphorous acid |
| Principle of Determination | LC/MS/MS | LC/MS/MS |
| LOQ[1] [mg/kg]    Soil sample | 0.05 | 0.05 |

[1] defined as the lowest validated fortification level

FIGURE 45

Table 30: Reference item data

| Name of Substance | Batch Number | Content [%] | Date of Expiry |
|---|---|---|---|
| fosetyl-Al | 12/1080 | 97.6 | February 20, 2006 |
| phosphorous acid | 04911DN | 96.2 | March 02, 2008 |

FIGURE 46

Collision Energy:

| Compound | Precursor Ion Q1 Mass (amu) | Product Ion Q3 Mass (amu) | Dwell Time (msec) | Collision Energy (V) |
|---|---|---|---|---|
| Fosetyl-Al | 109 | 81 | 200 | -16 |
| Phosphorous acid | 81 | 79 | 400 | -22 |

FIGURE 47

Proposed fragmentation pathway for fosetyl-Al

Proposed fragmentation pathway for phosphorous acid

| Compound | Precursor Ion Q1 Mass (amu) | Product Ion Q3 Mass (amu) | Dwell Time (msec) | Collision Energy (V) |
|---|---|---|---|---|
| fosetyl-Al | 109 | 63 | 300 | -38 |
| phosphorous acid | 81 | 63 | 400 | -38 |

FIGURE 49

Proposed fragmentation pathway for fosetyl-Al m/z 109            m/z 63

Proposed fragmentation pathway for phosphorous acid m/z 81            m/z 63

Table 32: Standard concentrations prepared for the determination of detector linearity. The concentration corresponding to the LOQ is printed in bold figures.

| HPLC-MS/MS | Standard Concentrations [µg/L] | | | | | | | |
|---|---|---|---|---|---|---|---|---|
| fosetyl-Al | 0.25 | 0.4 | 0.5 | 1 | 2.5 | 5 | 10 | 25 |
| phosphorous acid | 0.25 | 0.4 | 0.5 | 1 | 2.5 | 5 | 10 | 25 |

FIGURE 51

Table 33: Soil Types

| Soil | Texture of Soil | Organic Matter [%] |
|---|---|---|
| Höfchen | silt loam (USDA) | 1.58 |
| Laacher Hof | sandy loam (USDA) | 2.06 |

FIGURE 52

Table 34: Apparent residues in untreated control samples for fosetyl-Al and phosphorous acid

| Sample Material | LOQ [mg/kg] | | Apparent residues [mg/kg] | |
| --- | --- | --- | --- | --- |
| | fosetyl-Al | phospho-rous acid | fosetyl-Al | phospho-rous acid |
| Höfchen | 0.05 | 0.05 | < 10% LOQ | < 20% LOQ |
| Laacher Hof | 0.05 | 0.05 | < 10% LOQ | < 10% LOQ |

FIGURE 53

Table 35: Summary of the determination of detector linearity for LC/MS/MS.

| Detection | Parameter | fosetyl-Al | phosphorous acid |
|---|---|---|---|
| LC/MS/MS | Linear range [µg/L] | 0.25 - 25 | 0.25 - 25 |
| | No. of concentrations | 7 or 8 | 7 or 8 |
| | No. of injections | 1 | 1 |
| | Model | 1/x weighted linear regression | 1/x weighted linear regression |
| | Correlation coefficient (R) for standards prepared in solvent | 0.9999 | ≥ 0.9996 |
| | Correlation coefficient (R) for matrix matched standards | ≥ 0.9997 | 0.9999 |

FIGURE 54

Table 36: Matrix effect evaluation for fosetyl-Al   FL : Fortification Level

| Sample Material | FL [mg/kg] | Number of Values (n) | Measurement using | | | |
|---|---|---|---|---|---|---|
| | | | Standards in pure solvent | | Matrix matched standards | |
| | | | Mean [%] | RSD [%] | Mean [%] | RSD [%] |
| Höfchen | 0.05 | 5 | 72 | 2.7 | 81 | 3.8 |
| | 0.5 | 5 | 78 | 1.1 | 78 | 3.2 |
| Laacher Hof | 0.05 | 5 | 71 | 2.3 | 67 | 5.7 |
| | 0.5 | 5 | 80 | 1.4 | 76 | 5.8 |

FIGURE 55

Table 37: Matrix effect evaluation for Phosphorous acid    FL : Fortification Level

| Sample Material | FL [mg/kg] | Number of Values (n) | Measurement using | | | |
| --- | --- | --- | --- | --- | --- | --- |
| | | | Standards in pure solvent | | Matrix matched standards | |
| | | | Mean [%] | RSD [%] | Mean [%] | RSD [%] |
| Höfchen | 0.05 | 5 | 91 | 3.2 | 76 | 10.0 |
| | 0.5 | 5 | 85 | 2.3 | 77 | 3.9 |
| Laacher Hof | 0.05 | 5 | 84 | 9.0 | 72 | 14.4 |
| | 0.5 | 5 | 84 | 2.0 | 78 | 3.1 |

FIGURE 56

Table 38: Recovery rates obtained for fosetyl-Al, RSD: relative standard deviation

| Fortification [mg/kg] | Soil | Single Values [%] | | | | | Mean [%] | RSD [%] |
|---|---|---|---|---|---|---|---|---|
| 0.05 | Höfchen | 75 | 71 | 70 | 72 | 73 | 72 | 2.7 |
| 0.05 | Laacher Hof | 70 | 72 | 71 | 74 | 70 | 71 | 2.3 |
| mean of all 0.05 mg/kg single values | | | | | | | 72 | 2.4 |
| 0.5 | Höfchen | 79 | 79 | 79 | 77 | 78 | 78 | 1.1 |
| 0.5 | Laacher Hof | 80 | 80 | 79 | 78 | 81 | 80 | 1.4 |
| mean of all 0.5 mg/kg single values | | | | | | | 79 | 1.5 |
| *mean of all Höfchen samples* | | | | | | | 75 | 4.7 |
| *mean of all Laacher Hof samples* | | | | | | | 76 | 6.0 |
| overall mean | | | | | | | 75 | 5.3 |

FIGURE 57

Table 39: Recovery rates obtained for Phosphorous acid, RSD: relative standard deviation

| Fortification [mg/kg] | Soil | Single Values [%] | | | | | Mean [%] | RSD [%] |
|---|---|---|---|---|---|---|---|---|
| 0.05 | Höfchen | 95 | 90 | 87 | 91 | 91 | 91 | 3.2 |
| 0.05 | Laacher Hof | 98 | 80 | 82 | 81 | 81 | 84 | 9.0 |
| mean of all 0.05 mg/kg single values | | | | | | | 88 | 7.3 |
| 0.5 | Höfchen | 87 | 84 | 86 | 82 | 84 | 85 | 2.3 |
| 0.5 | Laacher Hof | 84 | 83 | 84 | 83 | 87 | 84 | 2.0 |
| mean of all 0.5 mg/kg single values | | | | | | | 84 | 2.0 |
| *mean of all Höfchen samples* | | | | | | | *88* | *4.6* |
| *mean of all Laacher Hof samples* | | | | | | | *84* | *6.2* |
| overall mean | | | | | | | 86 | 5.6 |

FIGURE 58

Table 40: Summary of the recovery data for the determination of accuracy and repeatability; RSD: relative standard deviation

|  | Parameter | Fosetyl-Al | Phosphorous acid | Number of values n |
|---|---|---|---|---|
| Accuracy | Single recoveries [%] | 70 - 81 | 80 - 98 | 20 |
|  | Mean recoveries per fortification level [%] | 72 – 79 | 84 - 88 | 10 |
|  | Mean recoveries per kind of soils [%] | 75 - 76 | 84 - 88 | 10 |
|  | Overall mean [%] | 75 | 86 | 20 |
| Repeatability | RSD per fortification level [%] | 1.5 – 2.4 | 2.0 – 7.3 | 10 |
|  | RSD per kind of soils [%] | 4.7 – 6.0 | 4.6 – 6.2 | 10 |
|  | Overall RSD [%] | 5.3 | 5.6 | 20 |

FIGURE 59

Appendix 10
Flow Diagram of Residue Method 00974/M001

Soil sample preparation procedure

*Main point : for each set of samples, it is necessary to do a blank reagent without soil sample to be sure that no H3PO3 contamination (< 30% LOQ) coming from sample preparation is found (that is why disposable consumables are used)*

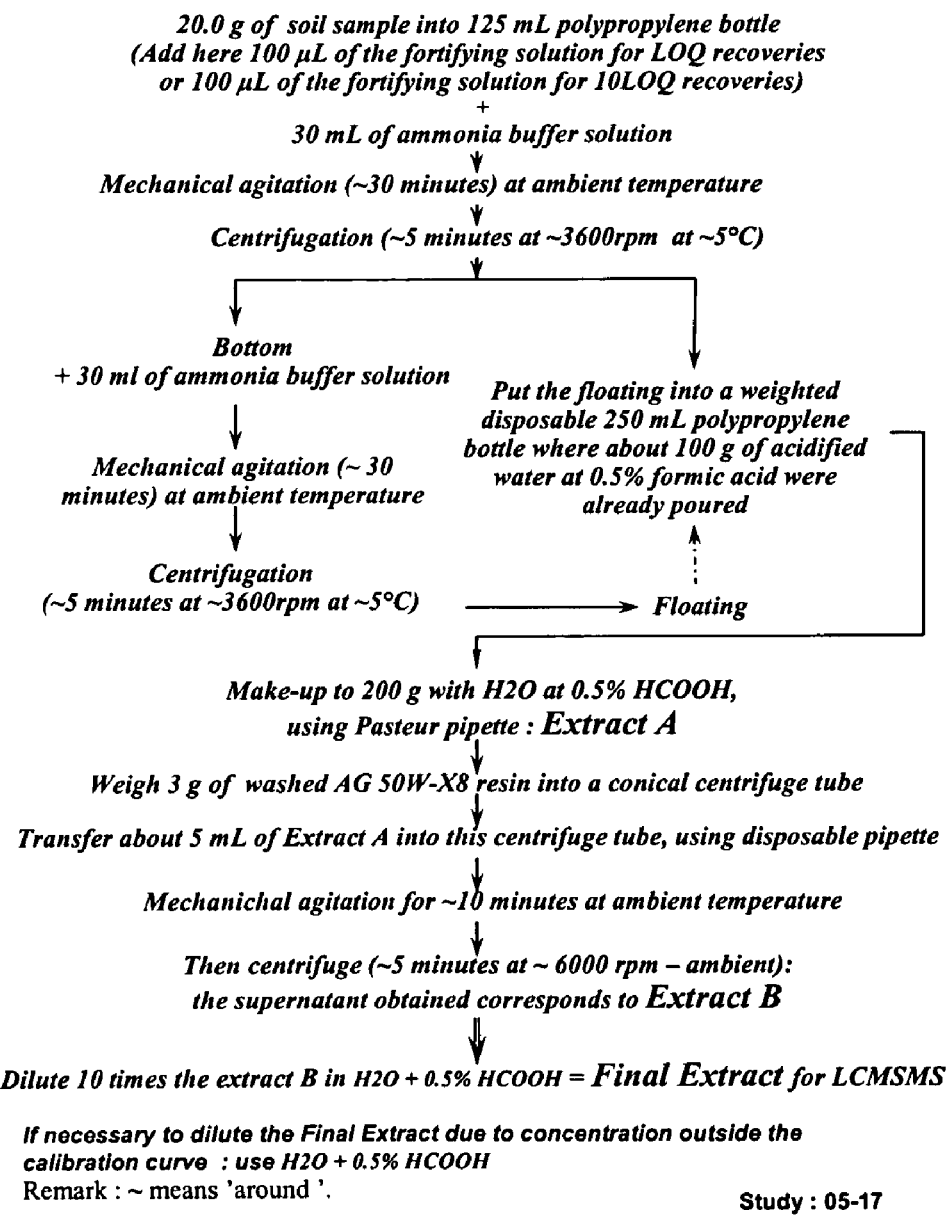

20.0 g of soil sample into 125 mL polypropylene bottle
(Add here 100 µL of the fortifying solution for LOQ recoveries
or 100 µL of the fortifying solution for 10LOQ recoveries)
+
30 mL of ammonia buffer solution
↓
Mechanical agitation (~30 minutes) at ambient temperature
↓
Centrifugation (~5 minutes at ~3600rpm at ~5°C)
↓

Bottom
+ 30 ml of ammonia buffer solution
↓
Mechanical agitation (~ 30 minutes) at ambient temperature
↓
Centrifugation
(~5 minutes at ~3600rpm at ~5°C) ⟶ Floating Put the floating into a weighted disposable 250 mL polypropylene bottle where about 100 g of acidified water at 0.5% formic acid were already poured Make-up to 200 g with H2O at 0.5% HCOOH,
using Pasteur pipette : *Extract A*
↓
Weigh 3 g of washed AG 50W-X8 resin into a conical centrifuge tube
↓
Transfer about 5 mL of Extract A into this centrifuge tube, using disposable pipette
↓
Mechanichal agitation for ~10 minutes at ambient temperature
↓
Then centrifuge (~5 minutes at ~ 6000 rpm – ambient):
the supernatant obtained corresponds to *Extract B*
⇓
Dilute 10 times the extract B in H2O + 0.5% HCOOH = *Final Extract for LCMSMS*

If necessary to dilute the Final Extract due to concentration outside the calibration curve  : use H2O + 0.5% HCOOH
Remark : ~ means 'around '.

Study : 05-17

FIGURE 60

Appendix 11
Details on LC-MS/MS conditions

Comment:
Synchronization Mode: LC Sync
Auto-Equilibration: Off
Acquisition Duration: 10min1sec
Number Of Scans: 455
Periods In File: 1
Acquisition Module: Acquisition Method
Software version Analyst 1.4

MS Method Properties:

Period 1:
--------------

Scans in Period: 455
Relative Start Time: 0.00 msec
Experiments in Period: 1

Period 1 Experiment 1:
---------------------------

Scan Type: MRM (MRM)
Polarity: Negative
Scan Mode: N/A
Ion Source: Turbo Spray
Resolution Q1: Unit
Resolution Q3: Unit
Intensity Thres.: 0.00 cps
Settling Time: 0.0000 msec
MR Pause: 5.0070 msec
MCA: No
Step Size: 0.00 amu Quantifier transitions:

| Q1 Mass (amu) | Q3 Mass (amu) | Dwell(msec) | Param | Start | Stop |
|---|---|---|---|---|---|
| 80.90 | 78.90 | 400.00 | DP | -55.00 | -55.00 |
| (phosphorous acid) | | | CE | -22.00 | -22.00 |
| | | | CXP | -5.00 | -5.00 |

| Q1 Mass (amu) | Q3 Mass (amu) | Dwell(msec) | Param | Start | Stop |
|---|---|---|---|---|---|
| 108.90 | 80.90 | 200.00 | DP | -45.00 | -45.00 |
| (fosetyl-Al) | | | CE | -16.00 | -16.00 |
| | | | CXP | -1.00 | -1.00 |

FIGURE 61(a)

Confirmatory transitions:

| Q1 Mass (amu) | Q3 Mass (amu) | Dwell(msec) | Param | Start | Stop |
|---|---|---|---|---|---|
| 80.90 | 62.90 | 400.00 | DP | -55.00 | -55.00 |
| (phosphorous acid) | | | CE | -38.00 | -38.00 |
| | | | CXP | -1.00 | -1.00 |

| Q1 Mass (amu) | Q3 Mass (amu) | Dwell(msec) | Param | Start | Stop |
|---|---|---|---|---|---|
| 108.90 | 62.90 | 300.00 | DP | -45.00 | -45.00 |
| (fosetyl-Al) | | | CE | -38.00 | -38.00 |
| | | | CXP | -5.00 | -5.00 |

Parameter Table (Period 1 Experiment 1):
CAD: 6.00
CUR: 15.00
GS1: 40.00
GS2: 60.00
TEM: 650.00
ihe: ON
IS: -4500.00
EP: -10.00

Agilent 1100 LC Pump Method Properties :

Pump Model: Agilent 1100 LC Binary Pump
Minimum Pressure (psi): 0.0
Maximum Pressure (psi): 5801.0
Dead Volume (µl): 40.0
Maximum Flow Ramp (ml/min$^2$): 100.0
Maximum Pressure Ramp (psi/sec): 290.0
Step Table:

| Step | Total Time(min) | Flow Rate(µl/min) | A (%) | B (%) |
|---|---|---|---|---|
| 0 | 0.00 | 200 | 55.0 | 45.0 |
| 1 | 10.00 | 200 | 55.0 | 45.0 |

Left Compressibility: 50.0
Right Compressibility: 115.0
Left Dead Volume (µl): 40.0
Right Dead Volume (µl): 40.0
Left Stroke Volume (µl): -1.0
Right Stroke Volume (µl): -1.0
Left Solvent: A1 (methanol + 2% formic acid)
Right Solvent: B2 (water + 2% formic acid)

FIGURE 61(a) (continued)

CTC PAL Autosampler Method Properties:

| | |
|---|---|
| Loop Volume1 (µl): | 50 |
| Loop Volume2 (µl): | 100 |
| Injection Volume (µl): | 100.000 |

Method Description:
    Syringe: 250ul
    Analyst LC-Inj

| | |
|---|---|
| Air Volume (µl) | 0 |
| Pre Clean with Solvent 1 () | 2 |
| Pre Clean with Solvent 2 () | 1 |
| Pre Clean with Sample () | 0 |
| Filling Speed (µl/s) | 50 |
| Filling Strokes () | 0 |
| Inject to | LC Vlv1 |
| Injection Speed (µl/s) | 50 |
| Pre Inject Delay (ms) | 500 |
| Post Inject Delay (ms) | 500 |
| Post Clean with Solvent 1 () | 3 |
| Post Clean with Solvent 2 () | 2 |
| Valve Clean with Solvent 1 () | 2 |
| Valve Clean with Solvent 2 () | 1 |

FIGURE 61(a) (continued)

| Gas pressure | | Autosampler CTC Analytics HTS Pal (GLP n° 1303) | |
|---|---|---|---|
| N2 | 4 bar | Peltier rack | 10 °C |
| Air GS1/GS2 gas | 7 bar | Wash solvent 1 : H2O + 0.5%HCOOH | |
| Air Exhaust gas | 4 bar | Wash solvent 2 : MeOH | |
| | | | |
| Pumps | | | |
| Analytical LC pump : | | | |
| Binary 1 pump Agilent 1100 (GLP n° 1296): | | | |
| A1 = Methanol + 2% Formic Acid | | Valco valve used | Column selector used |
| B2 = H$_2$O + 2% Formic Acid | | GLP n° 1289 | GLP n° 1356 |
| | | | |
| | | Source GLP n° 1291 | |
| | | | Probe TurboIonSpray |
| Pump for making-up solvent : | | | GLP n° 1288 |
| | | Horizontal Position | 7 (x axis) |
| | | Vertical Position | 7 (y axis) |
| | | Capillary exit | 1 mm |
| | | | |
| | | Mass Spectrometer API 4000 | |
| | | Device GLP n° | 1292 |
| Binary 2 pump Agilent 1100 (GLP n° 1297): | | | |
| A2 = H$_2$O + 2% Formic Acid | | Column : | at room temperature |
| B2 = Acetonitrile | | Precolumn : none | |
| | | Column : SMAR 68-1 Thermo Hypercarb 100 x 2.0mm 5µm | |
| | | | |
| | | | |

FIGURE 61(b)

Appendix 12
Results obtained with confirmatory transitions

All results in Tables 41 and 42 have been obtained by using standards prepared in solvents.

Table 41: Recovery rates obtained for Fosetyl-Al, RSD: relative standard deviation

| Fortification [mg/kg] | Soil | Single Values [%] | | | | | Mean [%] | RSD [%] |
|---|---|---|---|---|---|---|---|---|
| 0.05 | Höfchen | 77 | 73 | 72 | 76 | 74 | 74 | 2.8 |
| 0.05 | Laacher Hof | 72 | 72 | 76 | 76 | 74 | 74 | 2.7 |
| mean of all 0.05 mg/kg single values | | | | | | | 74 | 2.6 |
| 0.5 | Höfchen | 79 | 79 | 80 | 76 | 78 | 78 | 1.9 |
| 0.5 | Laacher Hof | 80 | 80 | 79 | 79 | 81 | 80 | 1.0 |
| mean of all 0.5 mg/kg single values | | | | | | | 79 | 1.7 |
| *mean of all Höfchen samples* | | | | | | | *76* | *3.6* |
| *mean of all Laacher Hof samples* | | | | | | | *77* | *4.4* |
| overall mean | | | | | | | 77 | 3.9 |

FIGURE 62(a)

Table 42: Recovery rates obtained for Phosphorous acid, RSD: relative standard deviation

| Fortification [mg/kg] | Soil | Single Values [%] | | | | | Mean [%] | RSD [%] |
|---|---|---|---|---|---|---|---|---|
| 0.05 | Höfchen | 92 | 87 | 85 | 87 | 85 | 87 | 3.3 |
| 0.05 | Laacher Hof | 87 | 75 | 78 | 73 | 79 | 78 | 6.8 |
| mean of all 0.05 mg/kg single values | | | | | | | 83 | 7.4 |
| 0.5 | Höfchen | 86 | 85 | 85 | 81 | 84 | 84 | 2.3 |
| 0.5 | Laacher Hof | 83 | 83 | 83 | 82 | 86 | 83 | 1.8 |
| mean of all 0.5 mg/kg single values | | | | | | | 84 | 2.0 |
| mean of all Höfchen samples | | | | | | | 86 | 3.3 |
| mean of all Laacher Hof samples | | | | | | | 81 | 5.6 |
| overall mean | | | | | | | 83 | 5.3 |

All results obtained above with confirmatory transition comply with European requirements.

FIGURE 62(b)

Appendix 13
Soil characterisation

Soil Höfchen

| Soil Höfchen, plot 4011: | 0 – 30 cm soil layer |
|---|---|
| pH (in CaCl$_2$ solution) | 6.7 |
| pH (in H$_2$O) | 7.4 |
| Organic Carbon [%] | 0.92 |
| Organic Matter [%] * | 1.58 |
| Cation Exchange Capacity [meq / 100 g dry soil] | 12.4 |
| max. Water Holding Capacity [g / 100 g dry soil] | 39.4 |

| Textural Description according to USDA | |
|---|---|
| Fraction [%] | |
| Clay (<0.002 mm) | 19.4 |
| Silt (0.002-0.050 mm) | 76.3 |
| Sand (0.050-2.000 mm) | 4.3 |
| Soil type: silt loam | |

* Organic matter = Organic carbon x 1.72

FIGURE 63(a)

Soil Laacher Hof

| Soil Laacher Hof, plot 712/718: | 0 – 30 cm soil layer |
|---|---|
| pH (in CaCl$_2$ solution) | 6.8 |
| pH (in H$_2$O) | 7.4 |
| Organic Carbon [%] | 1.20 |
| Organic Matter [%] * | 2.06 |
| Cation Exchange Capacity [meq / 100 g dry soil] | 9.8 |
| max. Water Holding Capacity [g / 100 g dry soil] | 37.9 |

| Textural Description according to USDA | |
|---|---|
| Fraction [%] | |
| Clay (<0.002 mm) | 12.0 |
| Silt (0.002-0.050 mm) | 18.3 |
| Sand (0.050-2.000 mm) | 69.7 |
| Soil type: sandy loam | |

* Organic matter = Organic carbon x 1.72

FIGURE 63(b)

METHOD OF ANALYZING PHOSPHOROUS ACID, FOSETYL-AL, OR BOTH SIMULTANEOUSLY

BACKGROUND OF THE INVENTION (1) Field of the Invention

The present invention relates to the field of pesticidal compound analysis. Such methods are useful for monitoring the behaviour of such pesticidal compounds once they have been applied, and such methods are also useful during marketing authority procedures for such pesticidal compounds.

(2) Description of Related Art

The compounds that can be analyzed by means of the method of analysis according to the invention are compounds that are useful for the protection of plants and also some of the compounds that are metabolites of these biologically active compounds. Some of these metabolites can also exhibit biological activities.

Methods for analyzing pesticidal compounds are known. In particular, an analytical method for determining the fosetyl-Al residue and its main metabolite, phosphorous acid, in drinking water or in surface water is known.

Such a known method uses (trimethylsilyl)diazomethane (TMSD) as a derivatizing agent.

Generally, such a method comprises the following steps:
concentration of the water samples;
derivatization with (trimethylsilyl)diazomethane of an aliquot of the concentrated sample (substitution of a hydrogen atom with a methyl group);
purification of the derivatized sample by liquid-liquid partition with dichloromethane.

The analysis is carried out by gas chromatography on a semi-capillary column by means of a flame photometric detector (or FPD) in the phosphorous mode and the quantification takes external standards as reference. The use of a thermionic detector is also possible.

This known method is carried out according to Scheme 1 below:

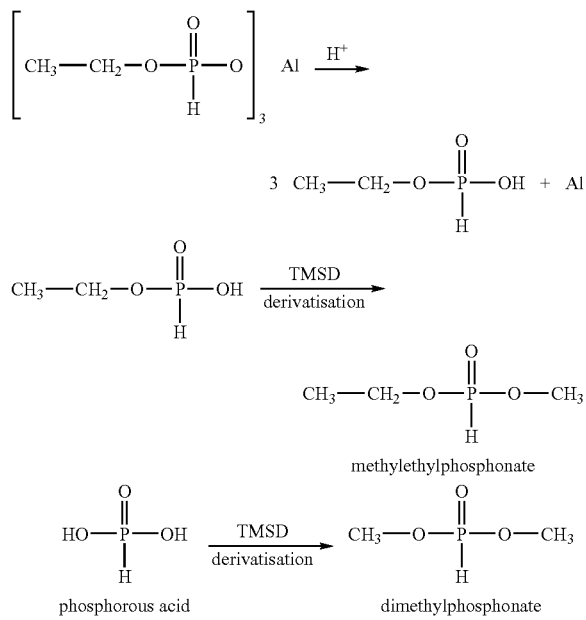

With this method, the limits of detection (LODs) are as follows:
for fosetyl-Al:
0.05 µg/l for drinking water (mineral or mains water);
0.05 µg/l for surface water (river water);
for phosphorous acid:
0.7 µg/l for drinking water (mineral or mains water);
2.5 µg/l for surface water (river water).

With this method, the limits of quantification (LOQs) are as follows:
for fosetyl-Al:
0.7 µg/l for drinking water (mineral or mains water);
1 µg/l for surface water (river water);
for phosphorous acid:
2.0 µg/l for drinking water (mineral or mains water);
4.0 µg/l for surface water (river water).

This known method of analysis has been used for the following substrates: mineral water, mains water and water from the Rhone river. The method of analysis has been validated for various types of water, by analysis of non treated control samples enriched in fosetyl-Al and in phosphorous acid to the limits of quantification and to 10 times these limits.

The analysis of these enriched samples gives recovery rate values for fosetyl-Al or for phosphorous acid, which are compared with the expected theoretical values.

As another known method of analysis, mention may be made of a method for analyzing fosetyl-Al or phosphorous acid residues present in soils taken in Chazay d'Azergues (France), in Goch (Germany) and in Seville (Spain).

This method itself also uses (trimethylsilyl)diazomethane. It is also carried out according to Scheme 1.

In this course of this method, the fosetyl-Al and phosphorous acid residues are extracted from the soil samples by agitation in the presence of an ammonia buffer solution, and then the cations that are present are removed from the extracts by means of an ion exchange resin and the water is evaporated from the samples. Finally, the extracts obtained are derivatized by the action of (trimethylsilyl)diazomethane.

Subsequently, the quantification is carried out by gas chromatography on a semi-capillary column using a flame photometric detector (in the phosphorous mode) with an external standard.

The limit of quantification (LOQ) of this method is 0.100 mg/kg for each of the compounds.

The control samples were enriched in fosetyl-Al or in phosphorous acid up to the limit of quantification and also up to 100 times this limit.

Another known method for analyzing residues concerns the analysis of fosetyl-Al and phosphorous acid residues in plant samples, derived both from fruits and from vegetables.

This method itself also uses (trimethylsilyl)diazomethane. It is also carried out according to Scheme 1.

In the course of this method, the fosetyl-Al and phosphorous acid residues are extracted from the plant samples by milling in a mixture of water and acetonitrile. The extracts are subsequently purified using a C18 cartridge and are then derivatized by the action of (trimethylsilyl)diazomethane.

Subsequently, the quantification is carried out by gas chromatography on a semi-capillary column using a flame photometric detector (in the phosphorous mode) with an external standard.

The limit of quantification of this known method is 0.50 mg/kg for each of the products, with the exception of hop, for which this limit is 2.0 mg/kg for fosetyl-Al and 20.0 mg/kg for phosphorous acid.

This method has been used on samples of bunches of grapes, of oranges, of bananas, of strawberries, of lettuce and of cucumbers. The control samples were enriched, in particular up to the limit of quantification.

Yet another known method for analyzing residues concerns the analysis of fosetyl-Al or phosphorous acid residues in animal tissues or products of animal origin, such as milk, bovine meat, bovine kidneys, bovine liver or eggs.

According to this study, the residues of compounds to be analyzed are extracted from the samples by double milling in a water/acetonitrile mixture (50/50, 20/80 for milk).

An aliquot of the extract is subsequently purified by means of a C18 cartridge (except for milk). The purified extract is subsequently derivatized with a solution of TMSD.

This method of analysis also follows Scheme 1.

The quantification is carried out by gas chromatography on a DB Wax column using a flame photometric detector in the phosphorous mode.

The limits of quantification are as follows:
0.50 mg/kg for fosetyl-Al and phosphorous acid in bovine meat, bovine kidney, bovine liver and eggs;
0.10 mg/kg for fosetyl-Al and phosphorous acid in milk.

For this method, non treated control samples were prepared and analyzed, along with samples enriched to the limit of quantification and also to several times this limit.

The known methods of analysis that have just been mentioned are in accordance with the provisions of European directive No. 46 from 1996 (96/46/EC of 16 Jul. 1996), in particular with respect to the following characteristics:
for each of the substrates and each level:
the mean of the recovery rates should be between 70 and 110%;
the repeatability, expressed as variation coefficient (ratio of the standard deviation to the mean for the sample concerned, expressed as a percentage) should be at most 20%;
for each of the substrates, the total variation coefficient (all levels included) should be at most 20%.

Another known method for analyzing fosetyl-Al is described in an article entitled Rapid determination of fosetyl-Al residues in lettuce by liquid chromatography/electrospray tandem mass spectrometry (Hernandez et al., Journal of AOAC International, Vol. 86, No. 4, 2003).

The method described concerns the quantification of fosetyl-Al residues in plant samples that are derived from lettuce. The method requires a step consisting of extraction with water by means of a high-speed mixer, followed by the injection of a 5-fold diluted extract into a liquid-phase chromatograph.

The fosetyl-Al is therefore quantified by liquid chromatography coupled to electrospray tandem mass spectrometry after addition of tetrabutylammonium acetate as an ionic pairing agent.

The analysis of samples of lettuce enriched at 2 and 0.2 mg/kg is reported. The limit of quantification is 0.2 mg/kg, whereas the limit of detection of fosetyl-Al is 0.05 mg/kg.

However, many of these known methods of analysis require a chemical derivatization step. Such an additional step complicates the analysis and very substantially prolongs the duration thereof. Furthermore, the implementation of this step requires specific expertise and increases the financial cost of these methods.

In addition, during such a derivatization step, the derivatizing agents used, which may be TMSD, diazomethane or other alternative derivatizing agents, are reactants which, in addition to their high cost, present considerable risks when they are used. Among the risks encountered when using such derivatizing agents, mention may be made of their toxicity and also their explosiveness. The use of such agents also results in a high cost.

Moreover, these known methods comprise many handling steps (evaporations, re-dissolutions, sample transfers) increasing, accordingly, the loss and dissemination of the compounds to be analyzed. Such a dissemination of compounds can also pose the problem of its environmental impact, in particular when the effluents derived from these methods of analysis are retreated.

Furthermore, these known methods have the major drawback of not being specific for particular compounds. This lack of specificity can result in compounds for which the protection and quantification characteristics are similar, not being differentiated. Other known methods have the disadvantage of only allowing the analysis of fosetyl-Al alone, without being able to carry out the simultaneous analysis of phosphorous acid, for example.

Some of the known methods are described only for particular matrices; for example, one already known method concerns only particular plant tissues derived from lettuce.

Finally, these known methods do not make it possible to achieve certain stricter limits of quantification, in particular the limits of quantification ensuing from recent regulations, for example directive 96/46/EC of 16 Jul. 1996.

BRIEF SUMMARY OF THE INVENTION

A method of analysis has now been found which makes it possible to provide a solution to these problems or to prevent these drawbacks related to the known methods.

Thus, the present invention relates to a method for analyzing residues of pesticidal compounds.

The method according to the invention may be suitable for the analysis of pesticidal compounds, whether they are fungicides, herbicides, insecticides or growth regulators.

Advantageously, the method of analysis according to the invention is used for analyzing residues of fungicidal compounds.

Particularly advantageously, the method of analysis according to the invention is used for analyzing fosetyl-Al residues and phosphorous acid residues.

fosetyl-Al is a fungicidal compound of phosphonic acid type, the chemical name of which is ethyl hydrogen phosphonic acid aluminium salt, having the formula $$\left[ Et-O-\underset{H}{\overset{O}{\underset{\|}{P}}}-O \right]_3 Al$$

Phosphorous acid has the formula $H_3PO_3$.

Thus, among other advantages, the method of analysis according to the present invention is of great simplicity. Furthermore, this method is direct and it makes it possible to achieve levels of quantification of the pesticidal compounds analyzed that have never before been achieved.

The method according to the invention is also particularly advantageous from an environmental point of view, and also economically.

In general, the present invention relates to a method for analyzing one or more pesticidal compounds present in amounts of less than or equal to 0.00005 mg/kg, preferably less than or equal to 0.000005 mg/kg, more preferably less than or equal to 0.0000005 mg/kg of a sample, comprising the following steps:

preparation of the sample;
optional dilution of the sample prepared;
direct analysis of the optionally diluted sample by high performance liquid chromatography (HPLC)/tandem mass spectrometry (MS/MS).

For the liquid samples analyzed according to the present invention, the limits of quantification can be expressed in mg/l. Those skilled in the art will be able to make the necessary conversions.

BRIEF DESCRIPTION OF THE DRAWINGS

FIG. 1 illustrates collision energies.
FIG. 2 illustrates recovery ranges.
FIG. 3 illustrates recovery ranges.
FIG. 4 illustrates the LOQ and principle of analytical determination.
FIG. 5 illustrates reference item data.
FIG. 6 illustrates collision gas $N_s$ (CAD).
FIG. 9 illustrates collision energies.
FIG. 12 illustrates standard concentrations.
FIG. 13 illustrates standard concentrations.
FIG. 14 illustrates origin of untreated control samples.
FIG. 15 illustrates apparent residues.
FIG. 16 illustrates a determination of detector linearity.
FIG. 17 illustrates a matrix effect evaluation for fosetyl-Al.
FIG. 18 illustrates a matrix effect evaluation for phosphorous acid.
FIG. 19 illustrates recovery rates.
FIG. 20 illustrates recovery rates.
FIG. 21 illustrates recovery data.
FIG. 22 illustrates stability periods.
FIG. 23 illustrates a flow diagram of residue method.
FIG. 24 illustrates an LOQ and principle of analytical determination.
FIG. 25 illustrates standard concentrations.
FIG. 26 illustrates the origin untreated control samples.
FIG. 27 illustrates characteristics of surface water.
FIG. 28 illustrates apparent residues.
FIG. 29 illustrates recovery rates.
FIG. 30 illustrates a summary of the determination of detector linearity.
FIG. 31 illustrates a matrix effect evaluation for fosetyl-Al.
FIG. 32 illustrates a matrix effect evaluation for phosphorous acid.
FIG. 33 illustrates recovery rates.
FIG. 34 illustrates recovery rates.
FIG. 35 illustrates recovery rates.
FIG. 36 illustrates an assessment of different LC conditions.
FIG. 37 illustrates results with substitute LC conditions.
FIG. 38 illustrates results with variant method.
FIG. 39 illustrates flow diagram of residue method.
FIG. 40 illustrates LC-MS/MS conditions.
FIG. 41 illustrates results with confirmatory transitions.
FIG. 42 illustrates results with substitute LC conditions.
FIG. 43 illustrates a flow chart of variant method.
FIG. 44 illustrates results with variant method.
FIG. 45 illustrates an LOQ and principle of analytical determination.
FIG. 46 illustrates item data.
FIG. 47 illustrates collision energies.
FIG. 49 illustrates collision energies.
FIG. 51 illustrates standard concentrations.
FIG. 52 illustrates soil types.
FIG. 53 illustrates apparent residues.
FIG. 54 illustrates a determination of detector linearity.
FIG. 55 illustrates a matrix effect evaluation for fosetyl-Al.
FIG. 56 illustrates a matrix effect evaluation for phosphorous acid.
FIG. 57 illustrates recovery rates.
FIG. 58 illustrates recovery rates.
FIG. 59 illustrates recovery data.
FIG. 60 illustrates the soil sample preparation procedure.
FIG. 61 illustrates the details on LC-MS/MS conditions.
FIG. 62 illustrates results of confirmatory transitions.
FIG. 63 illustrates soil characterization.

DETAILED DESCRIPTION OF THE INVENTION

Figure 7:
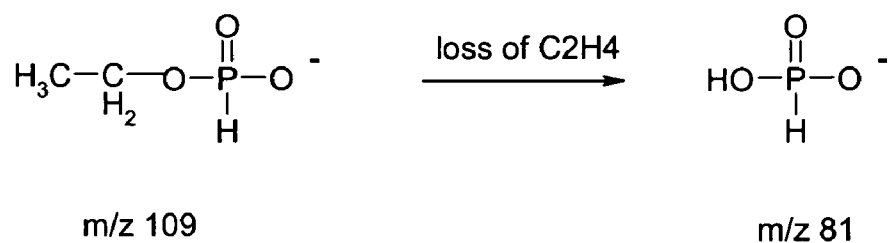
FIG. 7 illustrates a proposed fragmentation pathway for fosetyl-Al.

The method of analysis according to the invention may comprise a step consisting of dilution of the sample prepared.

The method of analysis according to the invention is suitable for the simultaneous analysis of several pesticidal compounds which may be fungicidal, herbicidal, insecticidal or growth-regulating compounds.

Preferably, the method according to the invention is used for the analysis of fungicidal compounds chosen from phosphorous acid or a derivative thereof; phosphonic acid or a derivative thereof; preferably for the analysis of fosetyl or of one or more salts thereof; more preferably for the analysis of fosetyl-Al or of phosphorous acid.

Particularly advantageously, the method of analysis according to the invention is used for the simultaneous analysis of phosphorous acid and of fosetyl-Al.

Preferably, the method of analysis according to the invention can be used for the analysis of samples chosen from plant tissues, preferably a plant matrix with a high water content, a plant matrix with an acidic pH, a dry plant matrix, a fatty plant matrix; water, preferably mineral water, underground water, mains water or surface water; soils; animal products or tissues, preferably milk, eggs, liver, kidneys, fats, muscle; air; agrofood products, preferably converted, and human body fluids such as blood and urine.

For the method of analysis according to the invention, the preparation step can be chosen from an extraction for plant tissues; soils; animal products or tissues and converted agrofood products; optional concentration for water and trapping for air.

Such a concentration step may also be used for other samples.

For the method of analysis according to the invention, the dilution step can be carried out in an aqueous solvent, which may be acidified, preferably chosen from formic acid, acetic acid or trifluoroacetic acid; or in an organic solvent, preferably acetonitrile or methanol, which may be acidified; or alternatively in a mixture of such solvents.

According to a first particular aspect of the invention, it relates to a method for analyzing one or more pesticidal compounds present in amounts of less than or equal to 0.005 mg/kg, preferably less than or equal to 0.00005 mg/kg, more preferably less than or equal to 0.0000005 mg/kg of a water sample, comprising the following steps:
- preparation of the water sample;
- optional dilution of the sample prepared;
- direct analysis of the optionally diluted sample by high performance liquid chromatography (HPLC)/tandem mass spectrometry (MS/MS).

The method for analyzing a water sample according to the invention may comprise a step consisting of dilution of the sample prepared.

The method for analyzing a water sample according to the invention is suitable for the simultaneous analysis of several pesticidal compounds which may be fungicidal, herbicidal, insecticidal or growth-regulating compounds.

Preferably, the method for analyzing a water sample according to the invention is used for the analysis of fungicidal compounds chosen from phosphorous acid or a derivative thereof; phosphonic acid or a derivative thereof; preferably for the analysis of fosetyl or one of more salts thereof; more preferably for the analysis of fosetyl-Al.

Particularly advantageously, the method for analyzing a water sample according to the invention is used for the simultaneous analysis of phosphorous acid and of fosetyl-Al.

Preferably, the method for analyzing a water sample according to the invention can be used for the analysis of samples chosen from mineral water, underground water, mains water or surface water.

For the method for analyzing a water sample according to the invention the preparation step may be a concentration.

For the method for analyzing a water sample according to the invention, the dilution step may be carried out in an aqueous solvent, which may be acidified, preferably chosen from formic acid, acetic acid or trifluoroacetic acid; or in an organic solvent, preferably acetonitrile or methanol, which may be acidified; or alternatively in a mixture of such solvents.

According to a second particular aspect of the invention, it relates to a method for analyzing one or more pesticidal compounds present in amounts of less than or equal to 1 mg/kg, preferably less than or equal to 0.01 mg/kg, more particularly less than or equal to 0.001 mg/kg of a plant tissue sample, comprising the following steps:
- preparation of the plant tissue sample;
- optional dilution of the sample prepared;
- direct analysis of the optionally diluted sample by high performance liquid chromatography (HPLC)/tandem mass spectrometry (MS/MS).

The method for analyzing a plant tissue sample according to the invention may comprise a step consisting of dilution of the sample prepared.

The method for analyzing a plant tissue sample according to the invention is suitable for the simultaneous analysis of several pesticidal compounds which may be fungicidal, herbicidal, insecticidal or growth-regulating compounds.

Preferably, the method for analyzing a plant tissue sample according to the invention is used for the analysis of fungicidal compounds chosen from phosphorous acid or a derivative thereof; phosphonic acid or a derivative thereof; preferably for the analysis of fosetyl or one or more salts thereof; more preferably for the analysis of fosetyl-Al.

Particularly advantageously, the method for analyzing a plant tissue sample according to the invention is used for the simultaneous analysis of phosphorous acid and of fosetyl-Al.

Preferably, the method for analyzing a plant tissue sample according to the invention can be used for the analysis of samples chosen from a plant matrix with a high water content, a plant matrix with an acidic pH, a dry plant matrix and a fatty plant matrix.

The method of analysis according to the invention can be used for the analysis of a sample of plants chosen from wheat, barley, potato, cotton, proteinaceous crops, oil-bearing crops, maize, flax, rice, vegetable crops, fruit trees, grapevine and beetroot.

For the method for analyzing a plant tissue sample according to the invention, the preparation step may be an extraction of the plant tissues. This preparation step may also comprise a concentration of the sample.

For the method for analyzing a plant tissue sample according to the invention, the dilution step can be carried out in an aqueous solvent, which may be acidified, preferably chosen from formic acid, acetic acid or trifluoroacetic acid; or in an organic solvent, preferably acetonitrile or methanol, which may be acidified; or alternatively in a mixture of such solvents.

According to a third particular aspect of the invention, it relates to a method for analyzing one or more pesticidal compounds present in amounts of less than or equal to 5 mg/kg, preferably less than or equal to 0.05 mg/kg, more particularly less than or equal to 0.005 mg/kg of a soil sample, comprising the following steps:
- preparation of the soil sample;
- optional dilution of the sample prepared;
- direct analysis of the optionally diluted sample by high performance liquid chromatography (HPLC)/tandem mass spectrometry (MS/MS).

The method for analyzing a soil sample according to the invention may comprise a step consisting of dilution of the sample prepared.

The method for analyzing a soil sample according to the invention is suitable for the simultaneous analysis of several pesticidal compounds which may be fungicidal, herbicidal, insecticidal or growth-regulating compounds.

Preferably, the method for analyzing a soil sample according to the invention is used for the analysis of fungicidal compounds chosen from phosphorous acid or a derivative thereof; phosphonic acid or a derivative thereof; preferably for the analysis of fosetyl or one or more salts thereof; more preferably for the analysis of fosetyl-Al.

Particularly advantageously, the method for analyzing a soil sample according to the invention is used for the simultaneous analysis of phosphorous acid and of fosetyl-Al.

The method for analyzing a soil sample according to the invention can be used for the analysis of any type of soil, for example clayey, sandy or chalky soil.

The method for analyzing soil according to the invention can be used for cultivated soils or for bare soils, in particular before a crop or after harvest.

For the method for analyzing a soil sample according to the invention, the preparation step may be an extraction of the soil sample. This preparation step may also comprise a concentration of the sample.

For the method for analyzing a soil sample according to the invention, the dilution step can be carried out in an aqueous solvent, which may be acidified, preferably chosen from formic acid, acetic acid or trifluoroacetic acid; or in an organic solvent, preferably acetonitrile or methanol, which may be acidified; or alternatively in a mixture of such solvents.

According to a fourth particular aspect of the invention, it relates to a method for analyzing one or more pesticidal compounds present in amounts of less than or equal to 0.1 mg/m$^3$, preferably less than or equal to 0.01 mg/m$^3$, more particularly less than or equal to 0.001 mg/m$^3$ of an air sample, comprising the following steps:
- preparation of the air sample;
- optional dilution of the sample prepared;
- direct analysis of the optionally diluted sample by high performance liquid chromatography (HPLC)/tandem mass spectrometry (MS/MS).

The method for analyzing an air sample according to the invention may comprise a step consisting of dilution of the sample prepared.

The method for analyzing an air sample according to the invention is suitable for the simultaneous analysis of several pesticidal compounds which may be fungicidal, herbicidal, insecticidal or growth-regulating compounds.

Preferably, the method for analyzing an air sample according to the invention is used for the analysis of fungicidal compounds chosen from phosphorous acid or a derivative thereof; phosphonic acid or a derivative thereof; preferably for the analysis of fosetyl or of one or more salts thereof; more preferably for the analysis of fosetyl-Al.

Particularly advantageously, the method for analyzing an air sample according to the invention is used for the simultaneous analysis of phosphorous acid and of fosetyl-Al.

For the method for analyzing an air sample according to the invention, the preparation step may be a trapping.

For the method for analyzing an air sample according to the invention, the dilution step can be carried out in an aqueous solvent, which may be acidified, preferably chosen from formic acid, acetic acid or trifluoroacetic acid; or in an organic solvent, preferably acetonitrile or methanol, which may be acidified; or alternatively in a mixture of such solvents.

According to a fifth particular aspect of the invention, it relates to a method for analyzing one or more pesticidal compounds present in amounts of less than or equal to 0.00005 mg/kg, preferably less than or equal to 0.000005 mg/kg, more preferably less than or equal to 0.0000005 mg/kg of a sample of a human body fluid, comprising the following steps:
- preparation of the human body fluid sample;
- optional dilution of the sample prepared;
- direct analysis of the optionally diluted sample by high performance liquid chromatography (HPLC)/tandem mass spectrometry (MS/MS).

The method for analyzing a sample of a human body fluid according to the invention may comprise a step consisting of dilution of the sample prepared.

The method for analyzing a sample of a human body fluid according to the invention is suitable for the simultaneous analysis of several pesticidal compounds which may be fungicidal, herbicidal, insecticidal or growth-regulating compounds.

Preferably, the method for analyzing a sample of a human body fluid according to the invention is used for the analysis of fungicidal compounds chosen from phosphorous acid or a derivative thereof; phosphonic acid or a derivative thereof; preferably for the analysis of fosetyl or of one or more salts thereof; more preferably for the analysis of fosetyl-Al.

Particularly advantageously, the method for analyzing a sample of a human body fluid according to the invention is used for the simultaneous analysis of phosphorous acid and of fosetyl-Al.

Preferably, the method for analyzing a sample of a human body fluid according to the invention can be used for the analysis of a sample chosen from human blood and human urine.

For the method for analyzing a sample of a human body fluid according to the invention, the dilution step can be carried out in an aqueous solvent, which may be acidified, preferably chosen from formic acid, acetic acid or trifluoroacetic acid; or in an organic solvent, preferably acetonitrile or methanol, which may be acidified; or alternatively in a mixture of such solvents.

According to a sixth particular aspect of the invention, it relates to a method for analyzing one or more pesticidal compounds present in amounts of less than or equal to 1 mg/kg, preferably less than or equal to 0.01 mg/kg, more preferably less than or equal to 0.001 mg/kg of a sample of animal products or tissues, comprising the following steps:
- preparation of the sample of animal products or tissues;
- optional dilution of the sample prepared;
- direct analysis of the optionally diluted sample by high performance liquid chromatography (HPLC)/tandem mass spectrometry (MS/MS).

The method for analyzing a sample of animal products or tissues according to the invention may comprise a step consisting of dilution of the sample prepared.

The method for analyzing a sample of animal products or tissues according to the invention is suitable for the simultaneous analysis of several pesticidal compounds which may be fungicidal, herbicidal, insecticidal or growth-regulating compounds.

Preferably, the method for analyzing a sample of animal products or tissues according to the invention is used for the analysis of fungicidal compounds chosen from phosphorous acid or a derivative thereof; phosphonic acid or a derivative thereof; preferably for the analysis of fosetyl or of one or more salts thereof; more preferably for the analysis of fosetyl-Al.

Particularly advantageously, the method for analyzing a sample of animal products or tissues according to the invention is used for the simultaneous analysis of phosphorous acid and of fosetyl-Al.

Preferably, the method for analyzing a sample of animal products or tissues according to the invention can be used for the analysis of a sample chosen from milk, eggs, liver, kidneys, fats and muscle.

For the method for analyzing a sample of animal products or tissues according to the invention, the dilution step can be carried out in an aqueous solvent, which may be acidified, preferably chosen from formic acid, acetic acid or trifluoroacetic acid; or in an organic solvent, preferably acetonitrile or methanol, which may be acidified; or alternatively in a mixture of such solvents.

For the method for analyzing a sample of animal products or tissues according to the invention, the preparation step may be an extraction of the animal products or tissues. This preparation step may also comprise a concentration of the sample.

According to a seventh particular aspect of the invention, it relates to a method for analyzing one or more pesticidal compounds present in a converted agrofood product sample. This method for analyzing a converted agrofood product sample according to the invention is similar to the method for analyzing a plant product sample according to the invention, in which the plant product sample is replaced with a converted agrofood product sample.

The various steps and preferences are also similar.

For the various aspects of the invention, in the analysis step, the external standards used are prepared in the presence of a matrix of the same nature as the sample to be analyzed.

The examples which follow are given by way of illustration of the various aspects of the invention. These examples do not limit the scope of the invention. In particular, those skilled in the art will be able to adapt or modify some of the steps of the method of analysis according to the invention according to the specific needs with which they will be confronted. Such modifications or adaptations are part of the scope of the present invention.

Example 1

This example concerns the analysis of fosetyl-Al and of phosphorous acid using plant tissue samples. The plant matrices are derived from crops: of cucumber, of orange, of lettuce, of grape and of avocado.

Procedure for using the method of analysis according to the invention:
1. Weigh 20.0 g of homogenized plant matrix sample into a 125 ml polypropylene flask.
2. Add 80 ml of the water/acetonitrile mixture (50/50, volume/volume).
3. Mill the sample for 5 minutes using an IKA T25-type mill.
4. Centrifuge for 5 minutes at 3600 rpm at 5° C.
5. Transfer the supernatant into a 200 ml volumetric flask.
6. Take up the pellet with 80 ml of the water/acetonitrile mixture (50/50, volume/volume).
7. Mill the sample again for 5 minutes.
8. Centrifuge for 5 minutes at 3600 rpm at 5° C.
9. Transfer the supernatant into the 200 ml volumetric flask.
10. Adjust to 200 ml using methanol.
11. Centrifuge an aliquot of approximately 10 ml for 10 minutes at 6000 rpm at ambient temperature.
12. Filter the supernatant through a PTFE filter (of the type Acrodisc CR 25 mm, 0.45 μm).
13. Dilute the filtrate 5 times using methanol acidified with 0.5% formic acid.
14. Analyze by high performance liquid chromatography (HPLC)/tandem mass spectrometry (MS/MS), or LC/MS/MS analysis.

To implement the analysis, the calibration is carried out by external standardization. The standards used must be prepared in a matrix of the same nature as the samples that are the subject of the specific analysis.

Analytical Conditions for Step 14:
High Performance Liquid Chromatography (HPLC) Conditions:

| Column: | Hypercarb, 100 × 3.0 mm, 5 μm |
|---|---|
| Precolumn: | Phenomenex C18 ODS, 4 × 2.0 mm |
| | Mobile phase: water acidified with 0.5% formic acid/methanol (65/35, volume/volume) isocratic mode |
| Flow rate: | 400 μl/min |
| Column temperature: | ambient |
| Injection volume: | 20 μl |

Before the analysis, the chromatographic system is left to stabilize for approximately 2 hours.

Tandem Mass Spectrometry (MS/MS) Conditions:

| Detector: | triple quadrupole, type API4000 Sciex Instrument |
|---|---|
| Interface: | TIS (Turbo Ion Spray) |
| Scan type: | MRM (Multiple Reaction Monitoring) mode |
| Polarity: | negative |
| Gas inlet pressure: | nitrogen: 4 bar |
| | air: 7.5 bar |
| | air (exhaust): 4 bar |
| Gas flow rate: | nebulizing gas (air, GS1): 40 |
| | turbo gas (air, GS2): 60 |

-continued

| | protective gas (nitrogen, CUR): 20 |
|---|---|
| | collision gas (nitrogen, CAD): 6 |
| High voltage TIS (IS): | −4500 V |
| Source temperature: | 600° C. |
| Entry potential (EP): | −10 V |

Collision energy is presented in FIG. 1: When the method of analysis according to the invention is used, steps 1 to 12 concern the preparation of the sample, and step 13 concerns the dilution. Thus, step 14 concerns the LC/MS/MS analysis of the plant matrix sample prepared beforehand and then diluted.

The results obtained from the analysis of various plant matrices are given in detail in the tables below, in which the CV values indicate the coefficient of variation. According to the present invention, the CV values can also correspond to RSD values.

These results were obtained from control samples which were enriched in fosetyl-Al and in phosphorous acid to limits of quantification (0.1 mg/kg for phosphorous acid and 0.01 mg/kg for fosetyl-Al) and to 10 times these limits and are presented in FIG. 2(a) through (j).

Example 2

This example also concerns the analysis of fosetyl-Al and of phosphorus acid using plant tissue samples. The plant matrices are derived from wheat crops.

This example repeats the conditions of Example 1 up to step 9, and then steps 10 to 14 of Example 1 are replaced with the following steps:
10. Add 1 ml of pure formic acid and adjust to 200 ml using methanol.
11. Centrifuge an aliquot of approximately 10 ml for 10 minutes at 6000 rpm at ambient temperature.
12. Dilute the supernatant twice using methanol acidified with 0.5% formic acid.
13. Filter through a PTFE filter (type Acrodisc CR 25 mm, 0.45 μm).
14. Analyze by high performance liquid chromatography (HPLC)/tandem mass spectrometry (MS/MS), or LC/MS/MS analysis.

For the rest, this example is identical to Example 1.
The results obtained from the analysis of a wheat sample are given in detail in the table below, in which CV indicates the coefficient of variation.

These results were obtained from control samples which were enriched in fosetyl-Al and in phosphorous acid to the limits of quantification (0.1 mg/kg for phosphorous acid and 0.01 mg/kg for fosetyl-Al) and to 10 times these limits and are presented in FIGS. 3(a) and (b).

For these two examples, the results obtained are in accordance with the regulatory provisions (96/46/EC of 16 Jul. 1996).

Furthermore, these results made it possible to attain limits of quantification that are below the limits available with the previously known methods.

These examples also demonstrate the simplicity and the greater safety of the method according to the invention.

Example 3

This detailed example concerns the analysis of fosetyl-Al and of phosphorous acid using plant tissue samples. This example is a modification M001 to the Analytical Method 00861 for the determination of residues of fosetyl-Al and its metabolite (phosphorous acid) in/on grape, orange, lettuce, cucumber, avocado and wheat by LCMSMS.

Description

Data Requirement:

EU Council Directive 91/414/EEC amended by Commission Directive 96/68/EC European Commission Guidance Document for Generating and Reporting Methods of Analysis in Support of Pre-Registration Data Requirements for Annex II (Part A, Section 4) and Annex III (Part A, Section 5) of Directive 91/414, SANCO/3029/99

European Commission Guidance Document for on Residue Analytical Methods, SANCO/825/00

Summary:

The presented residue analytical method modification 00861/M001 was validated for the determination of residues of fosetyl-Al and its metabolite (phosphorous acid) in grape (whole fruit), orange (whole fruit), lettuce (head), cucumber (whole fruit), avocado (whole fruit), and wheat (grain) by LC/MS/MS.

fosetyl-Al and its metabolite (phosphorous acid) were extracted from the sample material with a mixture of acetonitrile/water (50/50). After centrifugation and dilution of the sample material, the residues are quantified by HPLC using an Hypercarb column and detected by tandem mass spectrometry with electrospray ionisation. The quantification was done by an external standardisation in matrix matched standards The validation set included the determination of the detector linearity, the limit of quantification, the accuracy of the method and the storage stability of sample final extracts.

The linearity of the detector used was tested for fosetyl-Al and phosphorous acid using standards in solvent and matrix matched standards.

The linearity was tested by injecting standards of fosetyl-Al and phosphorous acid at respective concentrations between 0.1 and 5 µg/L and 1 and 50 µg/L, except for wheat samples between 0.31 and 8.3 µg/L and 3.1 and 83 µg/L.

The occurrence of matrix effects was monitored.

In all the sample materials, the measurement of phosphorus acid must be established using matrix matched standards. So the measurement of both compounds is established using matrix matched standards.

The apparent residues for all control samples were below 30% of the LOQ for each compound, i.e. <0.003 mg/kg of fosetyl-Al and 0.03 mg/kg of phosphorous acid.

The limit of quantification (LOQ) was defined as the lowest fortification level where a mean recovery within the range of 70 to 110% and an RSD of 20% could be obtained. The LOQ was set at 0.01 mg/kg for fosetyl-Al and at 0.1 mg/kg for phosphorous acid in grape (whole fruit), orange (whole fruit), lettuce (head), cucumber (whole fruit), avocado (whole fruit), and wheat (grain).

The accuracy of the method can be assessed on the basis of the determined recovery rates. The single recovery rates were in the range of 69 to 114% for fosetyl-Al and of 65 to 113% for phosphorous acid. The mean recovery rates per fortification level were in the range of 93 to 97% for fosetyl-Al with an overall recovery rate over all sample materials and fortification levels of 95% and of 86 to 97% for phosphorous acid with an overall recovery rate over all sample materials and fortification levels of 91%. The accuracy of the method fulfils the requirements for residue analytical methods which demand that the mean recoveries for each fortification level should be in the range of 70-110%.

The precision and repeatability of the method can be assessed on the basis of the determined relative standard deviations (RSD) for the mean values of the recovery rates. The relative standard deviations (RSD) for the single fortification levels ranged from 7.6 to 12.3% for fosetyl-Al and from 9.5 to 14.9% for phosphorous acid (n=30).

The relative standard deviations (RSD) for the single fortification levels ranged from 7.6 to 12.3% for fosetyl-Al and from 9.5 to 14.9% for phosphorous acid (n=30).

The overall RSD values per sample material were between 2.1 and 10.9% for fosetyl-Al and 6.0 and 17.8% for phosphorous acid (n=10). The RSD value across all samples was 10.2% for fosetyl-Al and 13.7% for phosphorous acid (n=60).

The overall RSD values per sample material were between 2.1 and 10.9% for fosetyl-Al and 6.0 and 17.8% for phosphorous acid (n=10). The RSD value across all samples was 10.2% for fosetyl-Al and 13.7% for phosphorous acid (n=60). All RSD values were well below 20%, so that the precision and repeatability of the method can be considered acceptable.

All results of the method validation are in accordance with the general requirements for residue analytical methods, so that this method modification has been validated successfully.

1 Introduction

Fosetyl-Al is a Fungicide

The method modification 00861/M001 presented in this report was validated in order to suppress the steps of clean up and derivatization, to change the analysis and detection modes and to decrease the Limit of Quantification (LOQ) of original method 00861 from 0.5 mg/kg to 0.01 mg/kg for fosetyl-Al and to 0.1 mg/kg for phosphorous acid and is presented in Table 1 of FIG. 4.

1.1 Citation of the Original Method

| | |
|---|---|
| Original Method: | 00861 |
| Compounds: | fosetyl-Al and its metabolite (phosphorous acid) |
| Reason for Modification: | Suppress the steps of clean up and derivatization |
| | Change analysis and detection modes from GC/FPD to LC/MS/MS |
| | Decrease the LOQ from 0.5 mg/kg to 0.010 mg/kg for fosetyl-Al and to 0.1 mg/kg for phosphorous acid |

1.2 Physical and Chemical Properties

| | |
|---|---|
| Name of the Substance | fosetyl-Al |
| Substance Code | AE F053616 |
| Chemical Name | Aluminium-tris-(ethylphosphonate) |
| Empirical Formula | $C_6H_{18}AlO_9P_3$ |
| Structural Formula | 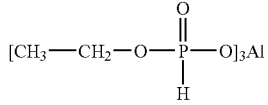 |
| Relative Molecular Mass | 354.1 g/mol |
| Monoisotopic Mass | 354.0 g/mol |
| Solubility | Water 120 g/L (20° C.) |
| | Acetonitrile 5 mg/L (20° C.) |
| Name of the Substance | Phosphorous acid |
| Substance Code | AE 0540099 |
| Chemical Name | Phosphonic acid |
| Empirical Formula | $H_3PO_3$ |
| Structural Formula | 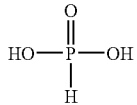 |

-continued

| | |
|---|---|
| Relative Molecular Mass | 82.0 g/mol |
| Monoisotopic Mass | 82.0 g/mol |

2 Experimental Section
2.1 Materials
2.1.1 Apparatus

| Standard laboratory glass equipment, rinsed with acetone. | |
|---|---|
| Balances : | |
| accuracy ± 0.1 mg (analytical standards) | (e.g. Mettler AT261 range) |
| accuracy ± 0.1 g (samples) | (e.g. Mettler PM6000) |
| Dilutor | (e.g. Hamilton MicroLab 500) |
| High-speed blender | (e.g. Ultra Turrax T25 with dispersion tool S 50 G-40G) |
| | (e.g. IKA) |
| Centrifuge | (e.g. Hermle Z513K) |
| | (ex Hettich EBA12) |
| HPLC | (e.g. Binary Pump Agilent 1100) |
| | (e.g. Quaternary pump Agilent 1100) |
| Auto sampler | (e.g. CTC Analytics HTC PAL) |
| Triple Quadrupole HPLC-MS/MS Mass Spectrometer | (e.g. Sciex Instruments, API 4000 System) |
| Column | (e.g. Hypercarb, 100 × 3.0 mm, 5 μm ) |

2.1.2 Reagents and Supplies

| | |
|---|---|
| Acetone, | (e.g. SupraSolv ® Merck) |
| Acetonitrile, | (e.g. SupraSolv ® Merck) |
| Methanol | (e.g. SupraSolv ® Merck) |
| Formic acid | (e.g. Normapur Prolabo) |
| PTFE filters (25 mm, 0.45 μm), | (e.g. Acrodisc CR Pall Gelman) |
| Polypro bottles (125 mL, wide opening) | (e.g. Nalgen) |
| Conical centrifuge tube 15 mL | (e.g. Merck 01 142.518) |
| Extraction solvent : | Acetonitrile/water (50/50, v/v) |
| Solvent for dilution | Methanol with 0.5% HCOOH |
| Mobile phase solvent: | Water with 0.5% HCOOH |

2.1.3 Reference Item

Only sufficiently characterised and certified item was used as reference item.

The reference item was made available by Bayer CropScience GmbH produkt Analytik, G864, Industriepark Hochst, D-65926 Frankfurt-am-Main, Germany, and is presented in Table 2 of FIG. 5.

2.1.4 Standard Solutions

Stock and standard solutions were stored protected from light in a refrigerator at around 5° C.

Stock Solutions (1000 mg/L)

Into a 100 mL amber screw-cap flask, weigh accurately between 20 and 50 mg of reference item. Using a burette, add a volume of water to obtain a stock solution of exactly 1000 mg/L. Mix thoroughly until complete dissolution using a magnetic stirrer. Two separate stock solutions must be prepared for each compound. After comparison of these two stock solutions, they are mixed.

Mixture Solution

First dilute 10 times fosetyl-Al stock solution with water. Then pipette 5 mL of it and 5 mL of phosphorous acid stock solution using a class "A*" pipette. Pour into a class "A*" 50 mL volumetric flask. Adjust volume with water, cap and mix by shaking: Mixture solution (10 mg/L fosetyl-Al—100 mg/L phosphorous acid).

Fortifying Standard Solutions

The mixture solution is also used as fortifying standard solution for recoveries at 10LOQ level. Dilute it 10 times with water to obtain the fortifying standard solution used for recoveries at LOQ level.

Standard Solutions in Solvent

By appropriate dilution of the fortifying solution used for recoveries at LOQ level (1 mg/L fosetyl-Al—10 mg/L phosphorous acid), prepare the intermediate standard solution at 0.05 mg/L of fosetyl-Al and 0.5 mg/L of phosphorous acid using methanol with 0.5% formic acid.

Standard Solutions in Solvent

To obtain the standard solutions used for calibration, dilute extemporaneously using a dilutor and methanol with 0.5% formic acid, the intermediate standard solution to obtain the following concentrations: 0.1 μg/L fosetyl-Al—1 μg/L phosphorous acid, 0.2 μg/L fosetyl-Al—2 μg/L phosphorous acid, 0.5 μg/L fosetyl-Al—5 μg/L phosphorous acid, 1 μg/L fosetyl-Al—10 μg/L phosphorous acid, 2 μg/L fosetyl-Al—20 μg/L phosphorous acid and 5 μg/L fosetyl-Al—50 μg/L phosphorous acid.

For wheat samples only, dilute extemporaneously using a dilutor and methanol with 0.5% formic acid, the intermediate standard solution to obtain the following concentrations: 0.31 μg/L fosetyl-Al—3.1 μg/L phosphorous acid, 0.5 μg/L fosetyl-Al—5 μg/L phosphorous acid, 0.83 μg/L fosetyl-Al—8.3 μg/L phosphorous acid, 1 μg/L fosetyl-Al—10 μg/L phosphorous acid, 2.5 μg/L fosetyl-Al—25 μg/L phosphorous acid, 5 μg/L fosetyl-Al—50 μg/L phosphorous acid and 8.3 μg/L fosetyl-Al—83 μg/L phosphorous acid.

Matrix Matched Standard Solutions Used for Calibration

The occurrence of matrix effects was monitored. and the measurement of both compounds is established using matrix matched standards in all the sample materials.

From the intermediate standard solution, the dilutions are the same as preparation of standard solutions in solvent, except the dilution mixture which is the final extract of a control sample.

Remark: 20 to 25 mL of final extract are necessary to make all dilutions. If the step of filtration is difficult, several filters can be used.

2.1.5 Stability of the Standard Solutions

The stock solutions, stored protected from light in a refrigerator at around 5° C., were found to be stable for 4 months and a half.

The fortifying standard solutions, stored protected from light in a refrigerator at around 5° C., were found to be stable for 2 months and a half.

2.2 Residue Analytical Methodology

Some modifications compared to the original analytical method were introduced:

The method modification 00861/M001 presented in this report was validated in order to suppress the steps of clean up and derivatization, to change the analysis and detection modes and to decrease the Limit of Quantification (LOQ) of original method 00861 from 0.5 mg/kg to 0.01 mg/kg for fosetyl-Al and to 0.1 mg/kg for phosphorous acid.

The Limit of Quantification was decreased from 0.5 mg/kg to 0.01 mg/kg for fosetyl-Al and to 0.1 mg/kg for phosphorous acid.

The C18 SPE cartridge clean-up step was suppressed.

The derivatization step was suppressed.

The quantification was carried out by LC/MS/MS instead of GC/FPD.

All modifications were included in the description below.

A flow chart of the method is given in Appendix 1.

For recovery experiments, samples are fortified by adding the appropriate standard solution to the sample material after weighing and before extraction.

Extraction

1. Weigh 20.0 g of homogeneous sample material into a 125 mL polypropylene bottle. Note: weight of the sample is used for residue calculation, addressed as variable G
2. Add 80 mL of acetonitrile/water (50/50, v/v).
3. Blend the sample using a high-speed blender (IKA or equivalent) for approx. 5 minutes.
4. Centrifuge the extract (3600 rpm-5° C.) for approx. 5 minutes.
5. Pour the supernatant into a 200 mL volumetric flask.
6. Add 80 mL of acetonitrile/water (50/50, v/v) on the bottom.
7. Blend the sample using a high-speed blender (IKA or equivalent) for approx. 5 minutes.
8. Centrifuge the extract (3600 rpm-5° C.) for approx. 5 minutes.
9. Pour the supernatant into the volumetric flask.
10. Make-up to 200 mL with methanol. This is the Extract A. Note: volume of extract A is used for residue calculation, addressed as variable V
11. Centrifuge an aliquot of about 10 mL of Extract A (6000 rpm-ambient) for approx. 10 minutes.
12. Filter the supernatant through an Acrodisc CR 25 mm PTFE filter (0.45 μm).
13. Dilute five times the extract using acidified methanol with formic acid 0.5%. This is the Final Extract.
14. Proceed to LC/MS/MS measurement, Chapter 2.3.

Remark: for wheat samples, from stage 10, follow the preparation as described below:

10. Add 1 mL of concentrated formic acid and make-up to 200 mL with methanol. This is the Extract A. Note: volume of extract A is used for residue calculation, addressed as variable V
11. Centrifuge an aliquot of about 10 mL of Extract A (6000 rpm-ambient) for approx. 10 minutes.
12. With dilutor, dilute twice the supernatant using methanol with formic acid 0.5%.
13. Filter the extract through an Acrodisc CR 25 mm PTFE filter (0.45 μm). This is the Final Extract.
14. Proceed to LC/MS/MS measurement, Chapter 2.3.

2.3 Analysis and Instrument Conditions

The final extracts are injected into a high performance liquid chromatograph and detected by tandem mass spectrometry with electrospray ionisation.

The quantification is carried out by external standardisation using matrix matched standards.

Exemplary LC/MS/MS conditions that were used in the course of this method validation are listed in chapters 2.3.1 and 2.3.2. These conditions are given as a guidance and may have to be adapted for other HPLC-MS/MS systems.

2.3.1 HPLC Conditions

Instrument: Binary pump Agilent 1100
  Quaternary pump Agilent 1100 (make-up solvent)
Auto sampler: CTC Analytics HTC PAL
Column: Hypercarb, 100×3.0 mm, 5 μm
Precolumn: Phenomenex C18 ODS, 4×2.0 mm
Injection Volume: 20 μL
Column temperature: ambient (about 25° C.)
Mobile Phase Isocratic mode: 35/65 (v/v) Methanol/water+ 0.5% formic acid
Flow (Column): 400 μL/min
Retention Times: from 4 to 6 min for phosphorous acid and from 7 to 10 min for fosetyl-Al.
Divert valve: Valve situated between the analytical column and the MS/MS system.

This valve was used to protect the ion source from contamination and to reduce the risk of ion suppression occurring, the eluent from the first minutes of the run was diverted to waste and a make-up flow was used to obviate the need for the ion source to stabilize after diverting the LC eluent flow back to the mass spectrometer.

Make up solvent: 50/50 (v/v) Methanol/water
Divert flow: 200 μL/min
Remarks:
  It is necessary to wait about 2 hours the stabilisation of the HPLC system before injecting. During a samples set, a light drift of retention time of both compounds can be observed.
  Hypercarb precolumn must not be used.

2.3.2 MS/MS Conditions

The experiments were performed on a triple-quadrupole mass spectrometer system, fitted with an electrospray interface operated in the negative ion mode under MRM (multiple reaction monitoring) conditions.

For Instance:
Detector: Triple Quadrupole HPLC-MS/MS Mass Spectrometer,
  e.g. Sciex Instruments, API 4000 System
Source: TIS (Turbo Ion Spray)
Temperature: 600° C.
Scan Type: MRM-Mode (Multiple Reaction Monitoring Mode)
Polarity: Negative ion mode
Gas Flows: Nebulization Gas Air (GS1):40
  Turbo Gas Air (GS2): 60
  Curtain Gas $N_2$ (CUR): 20

Details on MS/MS and LC conditions are given in Appendix 2.

Figure 8:
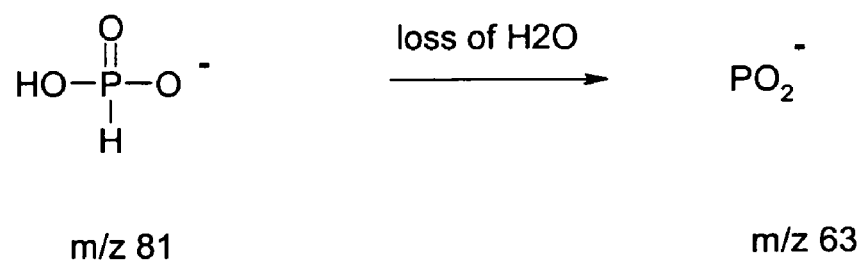
FIG. 8 illustrates a proposed fragmentation pathway for phosphorous acid.

The fragmentation pathways for the quantifier ions for fosetyl-Al and phosphorous acid are shown in FIG. 7 and in FIG. 8.

2.3.3 Confirmatory Transitions

To confirm or exclude some interference or pollution in samples, the transitions of FIG. 9 can be used in the same conditions described above.

Figure 10:
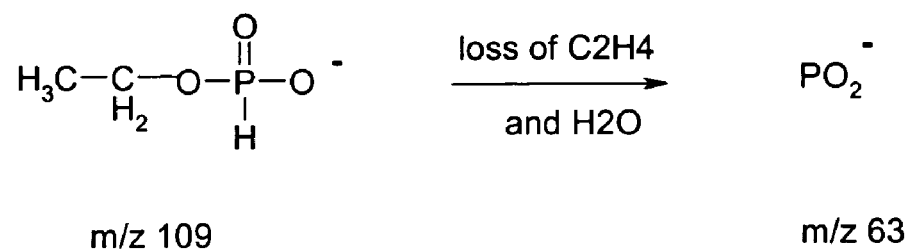
FIG. 10 illustrates a proposed fragmentation pathway for fosetyl-Al.
Figure 11:
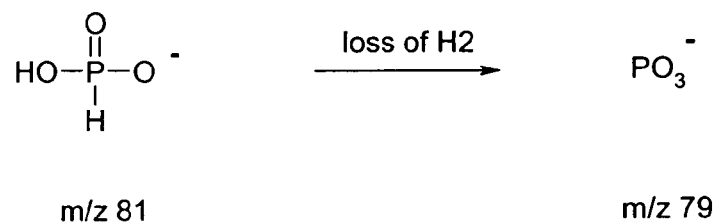
FIG. 11 illustrates a proposed fragmentation pathway for phosphorous acid.

The fragmentation pathways for the confirmatory transitions for fosetyl-Al and phosphorous acid are shown in FIG. 10 and in FIG. 11.

2.4 Linearity of the Detector

The linearity of the detector used was tested for fosetyl-Al and phosphorous acid using standards in solvent and matrix matched standards.

The linearity was tested by injecting standards of fosetyl-Al and phosphorous acid at respective concentrations between 0.1 and 5 μg/L and 1 and 50 μg/L, except for wheat samples between 0.31 and 8.3 μg/L and 3.1 and 83 μg/L. This linearity is shown in Tables 4 and 5 of FIGS. 12 and 13, 2.5 Storage Stability of Extracts The stability of sample extracts containing fosetyl-Al and phosphorous acid was determined for each sample material.

For this purpose, the final extract of recovery samples were stored in the auto sampler rack thermo stated at about 10° C. after initial analysis and re-analysed after a storage period of several days.

2.6 Calculation 2.6.1 Calculation of Residues

Evaluation in this case is performed according to the external standardisation using matrix matched standards.

During the analysis of each set of samples, the 6 (or 7 for wheat samples) standard solutions mentioned in Table 4 are injected once. Standards should be interspersed with samples to compensate for any minor change in instrument response.

For each compound, the peak area is plotted versus the concentration in order to establish a calibration curve obtained by linear regression weighting 1/x with least squares method.

The corresponding model to determine the concentration in final extracts is calculated using the Analyst Software (Version 1.4).

Each final extract is injected once using the same conditions as previously described for the standard solutions.

Using the predicting mathematical model previously established, the final concentration in μg/L of each compound is determined for each injection.

For each compound, the amount of residue R, expressed in mg/kg is calculated, using the following formula:

$$R = \frac{C \times V \times D}{1000 \times G}$$

where:
R: Determined amount of residue of fosetyl-Al or phosphorous acid in mg/kg
C: Concentration of fosetyl-Al or phosphorous acid found in the analysed extract in μg/L
V: Volume of the extract A in mL, here 200 mL
D: Dilution factor to obtain the Final Extract, here 5 (or 2 for wheat samples)
G: Sample weight of analytical sample in g, here 20 g 2.6.2 Calculation of Recovery Rates The concentration of each compound in μg/L is determined for the recovery sample according to 2.6.1.

The percent recovery rate is then calculated as follows:

$$Rec = \frac{C \times 100}{A}$$

where:
Rec: Recovered amount found in fortified sample in %
C: Concentration of fosetyl-Al or phosphorous acid found in the analysed extract in μg/L
A: Fortified amount of fosetyl-Al or phosphorous acid in μg/L 2.6.3 Calculation of Relative Standard Deviation (RSD)

The RSD is calculated as follows:

$$RSD(\%) = S.D./\text{Mean Recovery} \times 100\%$$

$$S.D. = \left[\frac{\sum (R_i - R_m)^2}{n-1}\right]^{1/2}$$

$R_i$: recovery
$R_m$: mean recovery
$n$: number of recoveries

3 Results and Discussion 3.1 Specificity and Selectivity

The method allows the determination of fosetyl-Al and its metabolite (phosphorous acid) in/on grape, orange, lettuce, cucumber, avocado and wheat samples.

The specificity of the method resulted from the HPLC separation in combination with the very selective MS/MS detection.

3.2 Apparent residues in Control Samples

Two control samples were analysed for each sample material. The origin of the control materials used is listed in Table 6 of FIG. 14.

A residue level estimation in control samples was performed. The results are listed in Table 7 of FIG. 15.

The apparent residues for all control samples were below 30% of the LOQ for each compound, i.e. <0.003 mg/kg of fosetyl-Al and <0.03 mg/kg of phosphorous acid.

3.3 Linearity of the Detectors and Matrix Effects

The linearity of the detector used was tested for fosetyl-Al and phosphorous acid using standards in solvent and matrix matched standards.

The linearity was tested by injecting standards of fosetyl-Al and phosphorous acid at respective concentrations between 0.1 and 5 μg/L and 1 and 50 μg/L, except for wheat samples between 0.31 and 8.3 μg/L and 3.1 and 83 μg/L.

Experimental details can be found in Chapter 2.4.

In each chromatogram, the measured peak area of fosetyl-Al or phosphorous acid is plotted versus the corresponding concentration of respectively fosetyl-Al or phosphorous acid contained in each standard solution, in order to obtain calibration curve of the form:

$$y = ax + b (1/x \text{ weighting})$$

where:
y=peak area,
x=concentration in injected standard solution

The results of the determination of detector response for LC/MS/MS are summarised in Table 8 of FIG. 16.

An excellent linear correlation between the injected amount of the analytes and the detector responses of LC/MS/MS was observed for standards in the range of 0.1 to 5 μg/L (or 0.31 to 8.3 μg/L for wheat) for fosetyl-Al and in the range of 1 to 50 μg/L (or 3.1 to 83 μg/L for wheat) for phosphorus acid, using either standards prepared in solvent or matrix matched standards.

The occurrence of matrix effects was monitored. The results are shown in Table 9 and Table 10 of FIGS. 17 and 18.

In all the sample materials, the measurement of phosphorus acid must be established using matrix matched standards. So the measurement of both compounds is established using matrix matched standards.

3.4 Limit of Quantification and Recovery Experiments

The limit of quantification (LOQ) was defined as the lowest fortification level where a mean recovery within the range of 70 to 110% and an RSD of 20% could be obtained. The LOQ was set at 0.01 mg/kg for fosetyl-Al and at 0.1 mg/kg for phosphorous acid in grape (whole fruit), orange (whole fruit), lettuce (head), cucumber (whole fruit), avocado (whole fruit), and wheat (grain).

To validate the method for these matrices, samples were fortified with a defined amount of fosetyl-Al and phosphorous acid prior to analysis.

3.5 Recovery Rates

The detailed recovery results obtained are listed in Table 11 and Table 12 of FIGS. 19 and 20.

The obtained recovery rates are summarised below in Table 13 of FIG. 20.

In total 60 recovery rates were determined for each compound. The single recovery rates were in the range of 69 to 114% for fosetyl-Al and of 65 to 113% for phosphorous acid. The mean recovery rates per fortification level were in the range of 93 to 97% for fosetyl-Al with an overall recovery rate over all sample materials and fortification levels of 95% and of 86 to 97% for phosphorous acid with an overall recovery rate over all sample materials and fortification levels of 91%.

The relative standard deviations (RSD) for the single fortification levels ranged from 7.6 to 12.3% for fosetyl-Al and from 9.5 to 14.9% for phosphorous acid (n=30). The overall RSD values per sample material were between 2.1 and 10.9% for fosetyl-Al and 6.0 and 17.8% for phosphorous acid (n=10). The RSD value across all samples was 10.2% for fosetyl-Al and 13.7% for phosphorous acid (n=60). The recovery data are summarized in Table 13 of FIG. 21.

3.6 Storage Stability of Extracts

The stability of final extracts containing fosetyl-Al and its metabolite phosphorous acid was determined. For this purpose, the final extracts of recovery samples were let in the auto sampler rack thermo stated at about 10° C. after initial analysis and re-analysed after a storage period of several days.

The results of the storage stabilities are detailed in Table 14 of FIG. 22.

4 Evaluation and Discussion

The presented residue analytical method modification 00861/M001 was validated for the determination of residues of fosetyl-Al and its metabolite (phosphorous acid) in grape (whole fruit), orange (whole fruit), lettuce (head), cucumber (whole fruit), avocado (whole fruit), and wheat (grain) by LC/MS/MS.

fosetyl-Al and its metabolite (phosphorous acid) were extracted from the sample material with a mixture of acetonitrile/water (50/50). After centrifugation and dilution of the sample material, the residues are quantified by HPLC using an Hypercarb column and detected by tandem mass spectrometry with electrospray ionisation. The quantification was done by an external standardisation in matrix matched standards The validation set included the determination of the detector linearity, the limit of quantification, the accuracy of the method and the storage stability of sample final extracts.

The linearity of the detector used was tested for fosetyl-Al and phosphorous acid using standards in solvent and matrix matched standards.

The linearity was tested by injecting standards of fosetyl-Al and phosphorous acid at respective concentrations between 0.1 and 5 µg/L and 1 and 50 µg/L, except for wheat samples between 0.31 and 8.3 µg/L and 3.1 and 83 µg/L. The detector response was linear in these ranges.

The occurrence of matrix effects was monitored.

In all the sample materials, the measurement of phosphorus acid must be established using matrix matched standards. So the measurement of both compounds is established using matrix matched standards.

The apparent residues for all control samples were below 30% of the LOQ for each compound, i.e. <0.003 mg/kg of fosetyl-Al and <0.03 mg/kg of phosphorous acid.

The limit of quantification (LOQ) was defined as the lowest fortification level where a mean recovery within the range of 70 to 110% and an RSD of 20% could be obtained. The LOQ was set at 0.01 mg/kg for fosetyl-Al and at 0.1 mg/kg for phosphorous acid in grape (whole fruit), orange (whole fruit), lettuce (head), cucumber (whole fruit), avocado (whole fruit), and wheat (grain).

The accuracy of the method can be assessed on the basis of the determined recovery rates. The single recovery rates were in the range of 69 to 114% for fosetyl-Al and of 65 to 113% for phosphorous acid. The mean recovery rates per fortification level were in the range of 93 to 97% for fosetyl-Al with an overall recovery rate over all sample materials and fortification levels of 95% and of 86 to 97% for phosphorous acid with an overall recovery rate over all sample materials and fortification levels of 91%. The accuracy of the method fulfils the requirements for residue analytical methods which demand that the mean recoveries for each fortification level should be in the range of 70-110%.

The precision and repeatability of the method can be assessed on the basis of the determined relative standard deviations (RSD) for the mean values of the recovery rates. The relative standard deviations (RSD) for the single fortification levels ranged from 7.6 to 12.3% for fosetyl-Al and from 9.5 to 14.9 for phosphorous acid (n=30). The overall RSD values per sample material were between 2.1 and 10.9% for fosetyl-Al and 6.0 and 17.8% for phosphorous acid (n=10). The RSD value across all samples was 10.2% for fosetyl-Al and 13.7% for phosphorous acid (n=60).

The overall RSD values per sample material were between 2.1 and 10.9% for fosetyl-Al and 6.0 and 17.8% for phosphorous acid (n=10). The RSD value across all samples was 10.2% for fosetyl-Al and 13.7% for phosphorous acid (n=60). All RSD values were well below 20%, so that the precision and repeatability of the method can be considered acceptable.

All results of the method validation are in accordance with the general requirements for residue analytical methods, so that this method modification has been validated successfully. The method validation is understood with reference to FIG. 23(*a*) through (d).

Example 4

This detailed example concerns the analysis of fosetyl-Al and of phosphorous acid using water samples. This example is a modification M001 to the Analytical Method 00931 for the determination of residues of fosetyl-Al and its metabolite (phosphorous acid) in/on drinking water and surface water by LCMSMS.

The presented residue analytical method modification 00931/M001 was validated for the determination of residues of fosetyl-Al and its metabolite (phosphorous acid) in drinking water and surface water by LC/MS/MS.

The sample material is treated with a cationic resin and then concentrated. The residues of fosetyl-Al and its metabolite (phosphorous acid) are quantified by HPLC using an Hypercarb column and detected by tandem mass spectrometry with electrospray ionisation. The quantification was done by an external standardisation in matrix matched standards.

The validation set included the determination of the detector linearity, the limit of quantification and the accuracy of the method.

The linearity of the detector used was tested for fosetyl-Al and phosphorous acid using standards in solvent and matrix matched standards.

The linearity was tested by injecting standards of fosetyl-Al and phosphorous acid at concentrations between 0.2 and 20 µg/L.

The occurrence of matrix effects was monitored. In drinking water, the measurement of fosetyl-Al must be established using matrix matched standards. The results obtained with standards in pure solvent for phosphorous acid in both sample materials do not always comply with European requirements. So the measurement of both compounds in drinking water and surface water is established using matrix matched standards.

The apparent residues for all control samples were below 30% of the LOQ for each compound, i.e. <0.00003 mg/L.

The limit of quantification (LOQ) was defined as the lowest fortification level where a mean recovery within the range of 70 to 110% and an RSD of 20% could be obtained. The LOQ was set at 0.0001 mg/L for each compounds in drinking water and surface water.

The accuracy of the method can be assessed on the basis of the determined recovery rates. The single recovery rates were in the range of 75 to 118% for fosetyl-Al and of 72 to 117% for phosphorous acid. The mean recovery rates per fortification level were in the range of 89 to 96% for fosetyl-Al with an overall recovery rate over all sample materials and fortification levels of 93% and of 91 to 93% for phosphorous acid with an overall recovery rate over all sample materials and fortification levels of 92%. The accuracy of the method fulfils the requirements for residue analytical methods which demand that the mean recoveries for each fortification level should be in the range of 70-110%.

The precision and repeatability of the method can be assessed on the basis of the determined relative standard deviations (RSD) for the mean values of the recovery rates. The relative standard deviations (RSD) for the single fortification levels ranged from 9.6 to 14.3% for fosetyl-Al and from 8.8 to 19.8% for phosphorous acid (n=10).

The overall RSD values per sample material were between 7.5 and 9.7% for fosetyl-Al and 9.3 and 12.4% for phosphorous acid (n=10). The RSD value across all samples was 12.7% for fosetyl-Al and 15.0% for phosphorous acid (n=20). All RSD values were well below 20%, so that the precision and repeatability of the method can be considered acceptable.

All results of the method validation are in accordance with the general requirements for residue analytical methods, so this method modification has been validated successfully.

A variant method was also validated on drinking water and surface water. The sample preparation of the main method was strongly simplified by the suppression of the concentration step. The variant method was successfully validated, according to the European requirements (96/46/EC of 16 Jul. 1996), for non concentrated drinking water and surface water at 0.1 µg/L for fosetyl-Al and ten times this limit for fosetyl-Al and at 1 µg/L for phosphorous acid when matrix matched standards were used, independently of the LC conditions tested.

Regarding to the main method, the sample preparation was greatly simplified and allows to save a lot of time.

1. Introduction

Fosetyl-Al is a Fungicide

The method modification 00931/M001 presented in this report was validated in order to suppress the steps of derivatization and clean up, to change the analysis and detection modes and to decrease the Limit of Quantification (LOQ) of original method 00931 from 0.001 mg/L for fosetyl-Al and 0.004 mg/L for phosphorous acid in surface water and from 0.002 mg/L for phosphorous acid in drinking water to 0.0001 mg/L for each compound in both sample materials. The LOQ and principle of analytical determination are presented in FIG. 24.

1.1. Citation of the Original Method

| | |
|---|---|
| Original Method: | 00931 |
| Compounds: | Fosetyl-Al and its metabolite (phosphorous acid) |
| Author: | L. Baudet - R. Diot - M. Guillet - J. L. Kieken Aventis CropScience Centre de Recherche de la Dargoire 14/20 rue Pierre Baizet 69009 Lyon - France |
| Citation: | Agredoc Numbers: R011760 and R011761 dated May 22, 2000 |
| Reason for Modification: | Suppress the steps of derivatization and clean up. Change analysis and detection modes from GC/FPD to LC/MS/MS. Decrease the LOQ from 0.001 mg/L for fosetyl-Al and 0.004 mg/L for phosphorous acid in surface water and from 0.002 mg/L for phosphorous acid in drinking water to 0.0001 mg/L for each compound in both sample materials. |

1.2. Physical and Chemical Properties

See example 3.

2. Experimental Section 2.1. Materials 2.1.1. Apparatus

Standard laboratory glass consumable should be cleaned with only detergents containing no phosphate and rinsed with water and acetone.

To avoid any contamination, the use of disposable laboratory consumable is strongly advised.

| Balances: | |
|---|---|
| accuracy ± 0.1 mg (analytical standards) | (e.g. Mettler AT261 range) |
| accuracy ± 0.1 g (samples) | (e.g. Mettler PM6000) |
| Dilutor | (e.g. Hamilton MicroLab 1000) |
| Rotary shaker | (e.g. Heidolph REAX 2) |
| Sample Concentrator | (e.g. Techne dri-block) |
| Ultrasonic bath | |
| HPLC | (e.g. Binary Pump Agilent 1100) |
| Auto sampler | (e.g. CTC Analytics HTC PAL) |
| Triple Quadrupole HPLC-MS/MS | (e.g. Sciex Instruments, |
| Mass Spectrometer | API 4000 System) |
| Column | (e.g. Hypercarb, 100 × 2.0 mm, 5 µm) |

2.1.2 Reagents and Supplies

| | |
|---|---|
| Acetone | (e.g. SupraSolv ® Merck) |
| Methanol | (e.g. SupraSolv ® Merck) |
| Formic acid | (e.g. Normapur Prolabo) |
| Cationic resin (AG 50W-X8, 20-50 Meshs, hydrogen form) | (e.g. Bio Rad) |
| GF/A filters (125 mm) | (e.g. Whatman) |
| Polypro bottles (125 mL, wide opening) | (e.g. Nalgen) |
| Polypro bottles (1000 mL, wide opening) | (e.g. Nalgen) |
| Pyrex glass test tubes (20 × 150 mm) | (e.g. Corning) |
| Polypro funnels (67 mm) | (e.g. Marylands Plastics) |
| Glass disposable pipettes (5 mL) | |
| Solvent for dilution | Water with 0.5% HCOOH |
| Mobile phase solvent: | Water with 2% HCOOH Methanol with 2% HCOOH |

2.1.3. Reference Item

See example 3.

2.1.4. Standard Solutions

Stock and standard solutions were stored protected from light in a refrigerator at around 5° C.

Stock Solutions (1000 mg/L)

Into a 100 mL amber screw-cap flask, weigh accurately between 20 and 50 mg of reference item. Using a burette, add a volume of water to obtain a stock solution of exactly 1000 mg/L. Mix thoroughly until complete dissolution using a magnetic stirrer. Two separate stock solutions must be prepared for each compound. After comparison of these two stock solutions, they are mixed.

Mixture Solution

Pipette 5 mL of each stock solution using a class "A+" pipette. Pour into a class "A" 50 mL volumetric flask. Adjust volume with water, cap and mix by shaking (100 mg/L of each compound).

Fortifying Standard Solutions

By serial dilutions of the mixture solution in water, prepare the fortifying standard solution used for recoveries at 10LOQ level (0.1 mg/L of each compound) and the fortifying standard solution used for recoveries at LOQ level (0.01 mg/L of each compound).

Intermediate Standard Solution

By serial dilutions of the mixture solution, prepare the intermediate standard solution at 1.0 mg/L using water.

Standard Solutions in Solvent

To obtain the standard solutions used for calibration, dilute extemporaneously using a dilutor and water with 0.5% formic acid, the intermediate standard solution to obtain the following concentrations: 0.2, 0.4, 0.5, 0.75, 1, 2, 5, 10 and 20 µg/L.

Matrix Matched Standard Solutions Used for Calibration

The occurrence of matrix effects was monitored and the measurement of both compounds is established using matrix matched standards in both sample materials.

From the intermediate standard solution, the dilutions are the same as preparation of standard solutions in solvent, except the dilution mixture which is the final extract of a control sample.

20 to 25 mL of final extract are necessary to make all dilutions.

final extracts of control sample could be prepared a day before use and stocked in a refrigerator.

2.1.5. Stability of the Standard Solutions

The stock solutions, stored protected from light in a refrigerator at around 5° C., were found to be stable for 9 months and a half.

2.2. Residue Analytical Methodology

Some modifications compared to the original analytical method were introduced.

The method modification 00931/M001 presented in this report was validated in order to suppress the steps of derivatization and clean up, to change the analysis and detection modes and to decrease the Limit of Quantification (LOQ) of original method 00931 from 0.001 mg/L for fosetyl-Al and 0.004 mg/L for phosphorous acid in surface water and from 0.002 mg/L for phosphorous acid in drinking water to 0.0001 mg/L for each compound in both sample materials.

The Limit of Quantification was decreased from 0.001 mg/L for fosetyl-Al and 0.004 mg/L for phosphorous acid in surface water and from 0.002 mg/L for phosphorous acid in drinking water to 0.0001 mg/L for each compound in both sample materials.

The NaOH treatment was replaced by a resin treatment.

The derivatization step was suppressed.

The clean-up step with liquid-liquid partition was suppressed.

The quantification was carried out by LC/MS/MS instead of GC/FPD.

All modifications were included in the description below.

A flow chart of the method is given in Appendix 1 of FIG. 23(a).

During analysis, for each sample set, it is necessary to do a blank reagent where water sample is replaced by Milli Q water to be sure that no phosphorous acid contamination (<30% LOQ) coming from sample preparation is found.

Remark: standard laboratory glass consumable should be cleaned with only detergents containing no phosphate and rinsed with water and acetone.

To avoid any contamination, the use of disposable laboratory consumable is strongly advised.

For recovery experiments, samples are fortified by adding the appropriate standard solution to the sample material after weighing and before shaking.

Preparation of the Cationic Resin:

15. Weigh about 25 g of AG 50W-X8 resin into a 1000 mL polypropylene bottle.
16. Add about 500 mL of water.
17. Shake using a rotary shaker for about 10 minutes.
18. Discard the supernatant water.
19. Do steps 2 to 4 a second time.
20. Do steps 2 to 4 a third time.
21. Filtrate residual water and resin through two GF/A filters put in a polypropylene funnel and previously rinsed with water.

The resin is prepared either just before use or in advance, stored at ambient temperature and re-hydrated just before use.

Caution is required because the phosphorous acid interferences could be observed if the resin is not washed as described above.

Samples Preparation:

1. Weigh 0.6 g of AG 50W-X8 resin previously washed into a 125 mL polypropylene bottle.
2. Using disposable Pasteur pipette, weigh 20.0 g of homogeneous sample material into the bottle.

Note: weight of the sample is used for residue calculation, addressed as variable $W_{Water}$ 3. Shake the sample using a rotary shaker for 10 minutes. This is the Extract A.

Note: The weight of Extract A is used for residue calculation, addressed as variable $W_{Extract}$ In this case, there was no extraction: no solvent was added to water sample;

it was just a resin treatment, so $W_{Extract}=W_{Water}=20$ g

4. Using a disposable glass pipette, transfer an aliquot of 5 mL of supernatant into a test tube previously weighted.

Note: The volume of aliquot is used for residue calculation, addressed as variable $V_{Aliquot}$ (Instead of transferring 5 mL, this aliquot could also be done by weighing 5 g=$W_{Aliquot}$)

5. Evaporate under a nitrogen flow using a sample concentrator at a temperature of about 60° C. to approximately 0.5 g. Caution not to evaporate to dryness.
6. Using disposable pipette, make-up to 1.0 g with acidified water with formic acid 0.5%.

Note: the concentration of formic acid in acidified water used in step 6 is a critical parameter: it has an important action on the H3PO3 peak shape obtained in LC. The increase from 0.5% to 2% of formic acid in acidified water can give a very large H3PO3 peak, and accordingly a loss of sensitivity.

7. Sonicate for about 5 minutes. This is the Final Extract.

Note: weight of Final Extract is used for residue calculation, addressed as variable $W_{End}$ 8. Proceed to LC/MS/MS measurement, Chapter 2.3.

Note: if it is necessary to dilute the Final Extract due to a concentration outside the calibration curve: use final extract of control sample because matrix matched standards are used for calibration.

2.3. Analysis and Instrument Conditions

The final extracts are injected into a high performance liquid chromatograph and detected by tandem mass spectrometry with electrospray ionisation.

The quantification is carried out by external standardisation using matrix matched standards.

Exemplary LC/MS/MS conditions that were used in the course of this method validation are listed in chapters 2.3.1 and 2.3.2. These conditions are given as a guidance and may have to be adapted for other HPLC-MS/MS systems 2.3.1. HPLC Conditions
Instrument: Binary pump Agilent 1100
Auto sampler: CTC Analytics HTS PAL
Column: Hypercarb, 100×2.0 mm, 5 µm
Precolumn: none
Injection Volume: 50 µL
Column temperature: ambient (about 25° C.)
Mobile Phase:
Isocratic mode: 55/45 (v/v) Methanol+2% formic acid/water+2% formic acid
Flow (Column): 200 µL/min
Retention Times: from 3.1 to 4.1 min for phosphorous acid and from 3.9 to 5.3 min for fosetyl-Al.
Retention times in concentrated samples are lightly shorter than in solvent (about 0.2 min in surface water and 0.5 min in drinking water).
It is necessary to wait about 2 hours the stabilisation of the HPLC system before injecting.
During a samples set, a light drift of retention time of both compounds can be observed.
Hypercarb precolumn must not be used.
Depending of the phase batch of Hypercarb column, the percentage of formic acid in the mobile phase could be adapted to improve peaks shape (from 0.5% to 2%).
2.3.2. MS/MS Conditions
See example 3.
2.3.3. Confirmatory Transitions
See example 3.
All recovery samples were also analysed using confirmatory transitions.
The results are given in Appendix 6 of FIG. 40.
2.4. Linearity of the Detector
The linearity of the detector used was tested for fosetyl-Al and phosphorous acid using standards in solvent and matrix matched standards.
The linearity was tested by injecting standards of fosetyl-Al and phosphorous acid at concentrations between 0.2 and 20 µg/L and is presented in Table 16 of FIG. 25.
2.5. Storage Stability of Extracts
The stability of sample extracts containing fosetyl-Al and phosphorous acid was not determined in this study.
2.6. Calculation
2.6.1. Calculation of Residues
Evaluation in this case is performed according to the external standardisation using matrix matched standards.
During the analysis of each set of samples, the 9 standard solutions mentioned in Table 16 of FIG. 25 are injected once. Standards should be interspersed with samples to compensate for any minor change in instrument response.
For each compound, the peak area is plotted versus the concentration in order to establish a calibration curve obtained by linear regression weighting 1/x with least squares method.
The corresponding model to determine the concentration in final extracts is calculated using the Analyst Software (Version 1.4).
Each final extract is injected once using the same conditions as previously described for the standard solutions.
Using the predicting mathematical model previously established, the final concentration in µg/L of each compound is determined for each injection.
For each compound, the amount of residue R, expressed in mg/L is calculated, using the following formula:

$$R = \frac{C \times V_{End} \times V_{Extract}}{1000 \times V_{Water} \times V_{Aliquot}}$$

where:
R: Determined amount of residue of fosetyl-Al or phosphorous acid in mg/L
C: Concentration of fosetyl-Al or phosphorous acid found in the final extract in µg/L
$V_{End}$: Volume of the final extract in mL, considering that: $V_{End}=W_{End}\times$Density$^{-1}$ where $W_{End}$=weight of the final extract in g, here 1 g and Density$^{-1}$=1 mL/g (*)
$V_{Extract}$: Volume of the extract A in mL, considering that: $V_{Extract}=W_{Extract}\times$Density$^{-1}$ where $W_{Extract}$=weight of the extract A in g, here 20 g and Density$^{-1}$=1 mL/g (*). In this case, there was no extraction: no solvent was added to water sample; it was just a resin treatment, so $W_{Extract}=W_{Water}=20$ g
$V_{Water}$: Volume of the analytical sample in mL, considering that: $V_{Water}=W_{Water}\times$Density$^{-1}$ where $W_{Water}$=weight of the water in g, here 20 g and Density$^{-1}$=1 mL/g (*)
$V_{Aliquot}$: Aliquot (of extract A) used before evaporation in mL, here 5 mL
If the aliquot has been weighed, $V_{Aliquot}=W_{Aliquot}\times$Density$^{-1}$
where $W_{Aliquot}$=weight of the aliquot in g, here 5 g and Density$^{-1}$=1 mL/g (*)
The density of all liquid samples (water, extracts) is considered equal to 1 independently to room temperature. This allows to convert weight of liquid samples into volume.
In order to express phosphorous acid in fosetyl-Al equivalent, the ratio of the molecular weight must be used:

$$\text{Ratio} = \frac{354.1 \text{ g/mol}}{(82.0 \times 3) \text{ g/mol}} = 1.44$$

because 1 mole fosetyl-Al (354.1 g) gives 3 moles of phosphorous acid.
2.6.2. Calculation of Recovery Rates
The concentration of each compound in µg/L is determined for the recovery sample according to 2.6.1
The percent recovery rate is then calculated as follows:

$$Rec = \frac{C \times 100}{A}$$

where:
Rec: Recovered amount found in fortified sample in %
C: Concentration of fosetyl-Al or phosphorous acid found in the analysed extract in µg/L
A: Fortified amount of fosetyl-Al or phosphorous acid in µg/L
2.6.3. Calculation of Relative Standard Deviation (RSD)
The RSD is calculated as follows:

RSD(%)=S.D./Mean Recovery×100%

$$S.D. = \left[\frac{\sum (R_1 - R_m)^2}{n-1}\right]^{1/2}$$

$R_i$: recovery $R_m$: mean recovery $n$: number of recoveries

3. Results and Discussion 3.1. Specificity and Selectivity

The method allows the determination of fosetyl-Al and its metabolite (phosphorous acid) in drinking water and surface water samples.

The specificity of the method resulted from the HPLC separation in combination with the very selective MS/MS detection.

3.2. Apparent residues in Control Samples

Two control samples were analysed for each sample material. The origin of the control materials used is listed in Table 17 of FIG. 26.

Some characteristics of surface water are recorded in Table 18 of FIG. 27.

A residue level estimation in control samples was performed. The results are listed in Table 19 of FIG. 28.

The apparent residues for all control samples were below 30% of the LOQ for each compound, i.e. <0.00003 mg/L.

3.3. Limit of Detection

Control sample fortified at 0.00005 mg/L were analysed to test the limit of detection of fosetyl-Al and phosphorous acid. The results are given in Table 20 of FIG. 29.

3.4. Linearity of the Detectors and Matrix Effects

The linearity of the detector used was tested for fosetyl-Al and phosphorous acid using standards in solvent and matrix matched standards.

The linearity was tested by injecting standards of fosetyl-Al and phosphorous acid at concentrations between 0.2 and 20 µg/L.

Experimental details can be found in Chapter 2.4.

In each chromatogram, the measured peak area of fosetyl-Al or phosphorous acid is plotted versus the corresponding concentration of respectively fosetyl-Al or phosphorous acid contained in each standard solution, in order to obtain calibration curve of the form:

$y = ax + b$ (1/x weighting)

where:

y=peak area, x=concentration in injected standard solution

The results of the determination of detector response for LC/MS/MS are summarised in Table 21 of FIG. 30.

An excellent linear correlation between the injected amount of the analytes and the detector responses of LC/MS/MS was observed for standards in the range of 0.2 to 20 µg/L for both compounds, using either standards prepared in solvent or matrix matched standards.

The occurrence of matrix effects was monitored. The results are shown in Table 22 and table 23 of FIGS. 31 and 32.

In drinking water, the measurement of fosetyl-Al must be established using matrix matched standards. The results obtained with standards in pure solvent for phosphorous acid in both sample materials do not always comply with European requirements. So the measurement of both compounds in drinking water and surface water is established using matrix matched standards.

3.5. Limit of Quantification and Recovery Experiments

The limit of quantification (LOQ) was defined as the lowest fortification level where a mean recovery within the range of 70 to 110% and an RSD of ≦20% could be obtained. The LOQ was set at 0.0001 mg/L for each compounds in drinking water and surface water.

To validate the method for these matrices, samples were fortified with a defined amount of fosetyl-Al and phosphorous acid prior to analysis.

3.6. Recovery Rates

The detailed recovery results obtained are listed in Table 24 and Table 25 of FIGS. 33 and 34.

The obtained recovery rates are summarised in Table 26 of FIG. 35.

In total 20 recovery rates were determined for each compound.

The single recovery rates were in the range of 75 to 118% for fosetyl-Al and of 72 to 117% for phosphorous acid. The mean recovery rates per fortification level were in the range of 89 to 96% for fosetyl-Al with an overall recovery rate over all sample materials and fortification levels of 93% and of 91 to 93% for phosphorous acid with an overall recovery rate over all sample materials and fortification levels of 92%.

The relative standard deviations (RSD) for the single fortification levels ranged from 9.6 to 14.3% for fosetyl-Al and from 8.8 to 19.8% for phosphorous acid (n=10).

The overall RSD values per sample material were between 7.5 and 9.7% for fosetyl-Al and 9.3 and 12.4% for phosphorous acid (n=10). The RSD value across all samples was 12.7% for fosetyl-Al and 15.0% for phosphorous acid (n=20).

3.7. Storage Stability of Extracts

The stability of sample extracts containing fosetyl-Al and phosphorous acid was not determined in this study.

4. Evaluation and Discussion

The presented residue analytical method modification 00931/M001 was validated for the determination of residues of fosetyl-Al and its metabolite (phosphorous acid) in drinking water and surface water by LC/MS/MS.

The sample material is treated with a cationic resin and then concentrated. The residues of fosetyl-Al and its metabolite (phosphorous acid) are quantified by HPLC using an Hypercarb column and detected by tandem mass spectrometry with electrospray ionisation. The quantification was done by an external standardisation in matrix matched standards.

The validation set included the determination of the detector linearity, the limit of quantification and the accuracy of the method.

The linearity of the detector used was tested for fosetyl-Al and phosphorous acid using standards in solvent and matrix matched standards.

The linearity was tested by injecting standards of fosetyl-Al and phosphorous acid at respective concentrations between 0.1 and 5 µg/L and 1 and 50 µg/L, except for wheat samples between 0.31 and 8.3 µg/L and 3.1 and 83 µg/L. The detector response was linear in these ranges.

The occurrence of matrix effects was monitored.

In all the sample materials, the measurement of phosphorus acid must be established using matrix matched standards. So the measurement of both compounds is established using matrix matched standards.

The apparent residues for all control samples were below 30% of the LOQ for each compound, i.e. <0.003 mg/kg of fosetyl-Al and <0.03 mg/kg of phosphorous acid.

The limit of quantification (LOQ) was defined as the lowest fortification level where a mean recovery within the range of 70 to 110% and an RSD of <20% could be obtained. The LOQ was set at 0.01 mg/kg for fosetyl-Al and at 0.1 mg/kg for phosphorous acid in grape (whole fruit), orange (whole fruit), lettuce (head), cucumber (whole fruit), avocado (whole fruit), and wheat (grain).

The accuracy of the method can be assessed on the basis of the determined recovery rates. The single recovery rates were in the range of 69 to 114% for fosetyl-Al and of 65 to 113% for phosphorous acid. The mean recovery rates per fortification level were in the range of 93 to 97% for fosetyl-Al with an overall recovery rate over all sample materials and fortification levels of 95% and of 86 to 97% for phosphorous acid with an overall recovery rate over all sample materials and fortification levels of 91%. The accuracy of the method fulfils the requirements for residue analytical methods which demand that the mean recoveries for each fortification level should be in the range of 70-110%.

The precision and repeatability of the method can be assessed on the basis of the determined relative standard deviations (RSD) for the mean values of the recovery rates. the relative standard deviations (RSD) for the single fortification levels ranged from 7.6 to 12.3% for fosetyl-Al and from 9.5 to 14.9% for phosphorous acid (n=30).

The relative standard deviations (RSD) for the single fortification levels ranged from 7.6 to 12.3% for fosetyl-Al and from 9.5 to 14.9% for phosphorous acid (n=30). The overall RSD values per sample material were between 2.1 and 10.9% for fosetyl-Al and 6.0 and 17.8% for phosphorous acid (n=10). The RSD value across all samples was 10.2% for fosetyl-Al and 13.7% for phosphorous acid (n=60). All RSD values were well below 20%, so that the precision and repeatability of the method can be considered acceptable.

All results of the method validation are in accordance with the general requirements for residue analytical methods, so this method modification has been validated successfully.

During analysis, for each sample set, it is necessary to do a blank reagent where water sample is replaced by Milli Q water to be sure that no phosphorous acid contamination (<30% LOQ) coming from sample preparation is found.

standard laboratory glass consumable should be cleaned with only detergents containing no phosphate and rinsed with water and acetone.

To avoid any contamination, the use of disposable laboratory consumable is strongly advised.

Before start of validation/measurements equipment/chemicals should be tested for any residues of phosphorous acid.

If some contamination is observed, see if the use of special HPLC vials (e.g. polypropylene vials, Agilent, art. 5182-0567) can be helpful to reduce the background for phosphorous acid.

The assessment of different LC conditions is presented in FIGS. 36 and 37.

When matrix matched standards are used, the different experiments done showed that for surface water the validation failed only for fosetyl-Al at LOQ and 10LOQ if substitute LC conditions are used. For drinking water, no problem was observed.

For drinking water, the method was successfully validated, according to the European requirements (96/46/EC of 16 Jul. 1996) at 0.1 µg/L and ten times this limit for fosetyl-Al and phosphorous acid, only when matrix matched standards were used, independently of LC conditions tested.

For surface water, the method was successfully validated, according to the European requirements (96/46/EC of 16 Jul. 1996) at 0.1 µg/L and ten times this limit for fosetyl-Al and phosphorous acid, only when matrix matched standards were used, depending on LC conditions tested (notably for fosetyl-Al).

5. Variant Method

A variant method was also validated on drinking water and surface water. The sample preparation of the main method was strongly simplified by the suppression of the concentration step and all recovery samples were analysed in the HPLC and detection conditions given in 2.3.1 and 2.3.2. before the concentration step.

A flow chart of the variant method is given in Appendix 8 of FIG. 43.

A summary of the results is given in Table 28 of FIG. 38 and the detailed recovery results obtained are listed in Appendix 7 of FIG. 42.

To quantify non concentrated water samples, it is necessary to adapt standards solutions concentrations. As phosphorous acid is not sensitive enough, this method does not allow its determination at the limit of quantification of 0.1 µg/L.

The variant method was successfully validated, according to the European requirements (96/46/EC of 16 Jul. 1996), for non concentrated drinking water and surface water at 0.1 µg/L for fosetyl-Al and ten times this limit for fosetyl-Al and at 1 µg/L for phosphorous acid when matrix matched standards were used, independently of the LC conditions tested.

Regarding to the main method, the sample preparation was greatly simplified and allows to save a lot of time.

Appendices 4 through 9 of FIGS. 39 through 44 further describe the invention.

Example 5

This detailed example concerns the analysis of fosetyl-Al and of phosphorous acid using soil samples. This example is a modification M001 to the Analytical Method 00974 for the determination of residues of fosetyl-Al and its metabolite (Phosphorous acid) in soils.

Data Requirement is as follows.

EU Council Directive 91/414/EEC amended by Commission Directive 96/46/EC

European Commission Guidance Document for Generating and Reporting Methods of Analysis in Support of Pre-Registration Data Requirements for Annex II (Part A, Section 4) and Annex III (Part A, Section 5) of Directive 91/414, SANCO/3029/99

European Commission Guidance Document for Residue Analytical Methods, SANCO/825/00 rev.7

Summary

The presented residue analytical method modification 00974/M001 was validated for the determination of residues of fosetyl-Al and its metabolite (phosphorous acid) in soils by LC/MS/MS.

The residues of fosetyl-Al and its metabolite (phosphorous acid) are extracted from the soil samples by shaking with ammonia buffer solution. This extract is then treated with a cationic resin and a final dilution is done before the analysis by LCMSMS. The residues are quantified by HPLC using an Hypercarb column and detected by tandem mass spectrometry with electrospray ionisation. The quantification was done by an external standardisation using standards prepared in pure solvent.

The validation set included the determination of the detector linearity, the limit of quantification and the accuracy of the method.

The linearity of the detector used was tested for fosetyl-Al and phosphorous acid using standards in solvent and matrix matched standards.

The linearity was tested by injecting standards of fosetyl-Al and phosphorous acid at concentrations between 0.25 and 25 µg/L.

The occurrence of matrix effects was monitored.

The conclusion is that:
no significant difference is observed when the measurement of fosetyl-Al is established using either standards prepared in solvents, or matrix matched standards;
the measurement of phosphorous acid is better (higher mean recoveries and lower RSD found) when it is established using standards prepared in solvents, instead of using matrix matched standards.

For all these reasons, standards prepared in solvents should be used. The apparent residues for all control samples were below 20% of the LOQ for each compound, i.e. <0.01 mg/kg.

The limit of quantification (LOQ) was defined as the lowest fortification level where a mean recovery within the range of 70 to 110% and an RSD of 20% could be obtained. The LOQ was set at 0.050 mg/kg for each compounds in soils samples.

The accuracy of the method can be assessed on the basis of the determined recovery rates. The single recovery rates were in the range of 70 to 81% for fosetyl-Al and of 80 to 98% for phosphorous acid. All mean recoveries rates were in the range of 70 to 110%. The accuracy of the method fulfils the requirements for residue analytical methods which demand that the mean recoveries for each fortification level should be in the range of 70-110%.

The precision and repeatability of the method can be assessed on the basis of the determined relative standard deviations (RSD) for the mean values of the recovery rates. All RSD were well below 20%. Thus the precision and repeatability of the method can be considered acceptable.

All results of the method validation are in accordance with the general requirements for residue analytical methods, so this method modification has been validated successfully.

1 Introduction
Fosetyl-Al is a Fungicide.

The method modification 00974/M001 presented in this report was validated in order to suppress the steps of derivatization, to change the analysis and detection modes and to decrease the Limit of Quantification (LOQ) of original method 00974 from 0.100 mg/kg to 0.050 mg/kg for fosetyl-Al and phosphorous acid and presented in FIG. 45.

1.1 Citation of the Original Method
Original Method: 00974
Compounds: fosetyl-Al and its metabolite (phosphorous acid)
Reason for Modification:
Suppress the steps of derivatization.
Change analysis and detection modes from GC/FPD to LC/MS/MS.
Decrease the LOQ from 0.100 mg/kg to 0.050 mg/kg for fosetyl-Al and phosphorous acid 1.2 Physical and Chemical Properties
See example 3.

2 Experimental Section
2.1 Materials
2.1.1 Apparatus

Standard laboratory glass consumable should be cleaned with only detergents containing no phosphate and rinsed with water and acetone.

To avoid any contamination, the use of disposable laboratory consumable is strongly advised.

| | |
|---|---|
| Balances: | |
| accuracy ± 0.1 mg (analytical standards) | (e.g. Mettler AT261 range) |
| accuracy ± 0.1 g (samples) | (e.g. Mettler PM2000) |
| Dilutor | (e.g. Hamilton MicroLab 1000 plus) |
| Rotary shaker | (e.g. Heidolph REAX 2) |
| Centrifuge | (e.g. Hermle Z513K) |
| | (ex Hettich EBA12) |
| HPLC | (e.g. Binary Pump Agilent 1100) |
| Autosampler | (e.g. CTC Analytics HTC PAL) |
| Triple Quadrupole HPLC-MS/MS Mass Spectrometer | (e.g. Sciex Instruments, API 4000 System) |
| Column | (e.g. Hypercarb, 100 × 2.0 mm, 5 μm) |

3.1.2 Reagents and Supplies

| | |
|---|---|
| Acetone | (e.g. Pestipur ® SDS) |
| Methanol | (e.g. Pestipur ® SDS) |
| Formic acid | (e.g. Analytical reagent ® Merck) |
| Ammonium hydrogen carbonate | (e.g. Normapur ® Merck) |
| ammonia solution 32% | (e.g. Rectapur ® Merck) |
| Cationic resin (AG 50W-X8, 20-50 Meshs, hydrogen form) | (e.g. Bio Rad) |
| GF/A filters (125 mm), | (e.g. Whatman) |
| Polypro bottles (1000 mL, wide opening) | (e.g. Nalgen) |
| Polypro bottles (250 mL, wide opening) | (e.g. Nalgen) |
| Polypro bottles (125 mL, wide opening) | (e.g. Nalgen) |
| Polypro bottles (60 mL, wide opening) | (e.g. Nalgen) |
| Polypro funnels (67 mm) | (e.g. Marylands Plastics) |
| Conical centrifuge tube (15 mL) | (e.g. Merck) |
| Solvent for dilution: | Water with 0.5% HCOOH |
| Mobile phase solvent: | Water with 2% HCOOH Methanol with 2% HCOOH |
| ammonia buffer solution: pour 500 mL of water in a 1000 mL volumetric flask, add 20 g of ammonium hydrogen carbonate and mix with a magnetic stirrer until complete solubilisation. Add 15 mL of ammonia solution 32% and complete to 1000 mL with water. | |

2.1.3 Reference Item

Only sufficiently characterised and certified item was used as reference item. The reference item was made available by Bayer CropScience GmbH produkt Analytik, G864, Industriepark Höchst, D-65926 Frankfurt-am-Main, Germany, and is presented in FIG. 46.

2.1.4 Standard Solutions

Stock and standard solutions were stored protected from light in a refrigerator at around 5° C.

Stock Solutions (1000 mg/L)

Into a 100 mL amber screw-cap flask, weigh accurately between 20 and 50 mg of reference item. Using a burette, add a volume of water to obtain a stock solution of exactly 1000 mg/L. Mix thoroughly until complete dissolution using a magnetic stirrer. Two separate stock solutions must be prepared for each compound. After comparison of these two stock solutions, they are mixed.

Mixture Solutions

Pipette 5 mL of each stock solution using a class "A+" pipette. Pour into a class "A" 50 mL volumetric flask. Adjust volume with water, cap and mix by shaking (100 mg/L of each compound). Two different mixture solutions are prepared.

Fortifying Standard Solutions

By dilution in water of one of the mixture solution, which is also used as fortifying solution for recoveries at 10LOQ level (100 mg/L of each compound), prepare the fortifying standard solution used for recoveries at LOQ level (10 mg/L of each compound).

Intermediate Standard Solution

By serial dilutions of the other mixture solution, prepare the intermediate standard solution at 1.0 mg/L of each compound using water.

Before use, the intermediate solution and the fortifying standard solution used for recoveries at LOQ level are compared to validate their preparation.

Standard solutions in solvent used for calibration

To obtain the standard solutions used for calibration, dilute extemporaneously using a dilutor (or in a different way) and water with 0.5% formic acid, the intermediate standard solution to obtain the following concentrations: 0.25, 0.4, 0.5, 1, 2.5, 5, 10 and 25 µg/L.

Matrix Matched Standard Solutions

The occurrence of matrix effects was monitored and the measurement of both compounds is established using matrix matched standards in both sample materials. From the intermediate standard solution, the dilutions are the same as preparation of standard solutions in solvent, except the dilution mixture which is the final extract of a control sample.

20 to 25 mL of final extract are necessary to make all dilutions.

To avoid the use of standard laboratory glass consumable, which could bring some H3PO3 contamination, the dilution of the control sample extract B is done by weighing. Using disposable Pasteur pipette weigh 3.0 g of extract B into a 60 mL polypropylene bottle. Using another disposable Pasteur pipette, make-up to 30.0 g with acidified water with formic acid 0.5%: this is the control sample final extract used as dilution mixture to prepare matrix matched standard solutions.

2.1.5 Stability of the Standard Solutions

The stock solutions, stored protected from light in a refrigerator at around 5° C., were found to be stable for 9 months and a half.

2.2 Residue Analytical Methodology

Some modifications compared to the original analytical method were introduced. The method modification 00974/M001 presented in this report was validated in order to suppress the steps of derivatization, to change the analysis and detection modes and to decrease the Limit of Quantification (LOQ) of original method 00974 from 0.100 mg/kg to 0.050 mg/kg for each compound.

The Limit of Quantification was decreased from 0.100 mg/kg to 0.050 mg/kg for fosetyl-Al and phosphorous acid.

The derivatization step was suppressed.

The quantification was carried out by LC/MS/MS instead of GC/FPD.

All modifications were included in the description below.

A flow chart of the method is given in Appendix 10 of FIG. 60.

Note: during analysis, for each sample set, it is necessary to do a blank reagent without soil sample to be sure that no phosphorous acid contamination (<30% LOQ) coming from sample preparation is found.

Standard laboratory glass consumable should be cleaned with only detergents containing no phosphate and rinsed with water and acetone.

To avoid any contamination, the use of disposable laboratory consumable is strongly advised.

For recovery experiments, samples are fortified by adding the appropriate standard solution to the sample material after weighing and before shaking.

Preparation of the Cationic Resin:
1. Weigh about 25 g of AG 50W-X8 resin into a 1000 mL polypropylene bottle.
2. Add about 500 mL of water.
3. Shake using a rotary shaker for about 10 minutes.
4. Discard the supernatant water.
5. Do steps 2 to 4 a second time.
6. Do steps 2 to 4 a third time.
7. Filtrate residual water and resin through two GF/A filters put in a polypropylene funnel and previously rinsed with water.

Resin is prepared either just before use or in advance, stored at ambient temperature and rehydrated just before use. Caution: phosphorous acid interferences could be observed if the resin is not washed as described above.

Samples Preparation:
1. Weigh 20.0 g of homogeneous sample material into a 125 mL polypropylene bottle. Note: weight of the sample is used for residue calculation, as variable $Weight_{Sample}$.
2. Add 30 mL of ammonia buffer solution.
3. Shake the sample using a rotary shaker for 30 minutes at ambient temperature.
4. Centrifuge the extract (3600 rpm-5° C.) for approx. 5 minutes.
5. Pour about 100 g of acidified water with formic acid 0.5% into a 250 mL polypropylene bottle previously weighted.
6. Add the supernatant into the 250 mL polypropylene bottle.
7. Add 30 mL of ammonia buffer solution on the bottom.
8. Shake the sample using a rotary shaker for 30 minutes.
9. Centrifuge the extract (3600 rpm-5° C.) for approx. 5 minutes.
10. Pour the supernatant into the 250 mL polypropylene bottle.
11. Using disposable Pasteur pipette, make-up to 200 g with acidified water with formic acid 0.5%. This is the Extract A (for information, the pH is around 6.5).

Note: weight of extract A is used for residue calculation, as variable $Weight_{Extract\ A}$.

12. Weigh 3.0 g of AG 50W-X8 resin previously washed into a conical centrifuge tube.
13. Using a disposable glass pipette, transfer an aliquot of 5 mL of Extract A into the centrifuge tube.
14. Shake the sample using a rotary shaker for 10 minutes.
15. Centrifuge the sample (6000 rpm-ambient) for approx. 5 minutes: the supernatant obtained corresponds to Extract B (for information, the pH is around 2.5).

Note: this step of resin treatment is necessary to obtain a narrow H3PO3 peak shape.

16. Dilute using a dilutor (or in a different way) ten times the extract B using acidified water with formic acid 0.5%. This is the Final Extract (for information, the pH is around 2.5).
17. Proceed to LC/MS/MS measurement, Chapter 3.3.
18. If necessary to dilute the Final Extract due to a concentration outside the calibration curve: use acidified water with formic acid 0.5%.

2.3 Analysis and Instrument Conditions

The final extracts are injected into a high performance liquid chromatograph and detected by tandem mass spectrometry with electrospray ionisation.

The quantification is carried out by external standardisation using standards prepared in solvent. Exemplary LC/MS/MS conditions that were used in the course of this method validation are listed in chapters 3.3.1 and 3.3.2. These conditions are given as a guidance and may have to be adapted for other HPLC-MS/MS systems.

2.3.1 HPLC Conditions

Instrument: Binary pump Agilent 1100
Autosampler: CTC Analytics HTS PAL
Column: Hypercarb, 100×2.0 mm, 5 µm
Precolumn: none
Injection Volume: 50 µL
Column temperature: ambient (about 25° C.)
Mobile Phase Isocratic mode: 55/45 (v/v) Methanol+2% formic acid/water+2% formic acid
Flow (Column): 200 µL/min Retention Times are about 3.1 min for phosphorous acid and 4.2 min for fosetyl-Al.

It is necessary to wait about 2 hours the stabilisation of the HPLC system before injecting. During a samples set, a light drift of retention time of both compounds can be observed.

Hypercarb precolumn must not be used.

Depending of the phase batch of Hypercarb column, the percentage of formic acid in the mobile phase could be adapted to improve peaks shape (from 0.5% to 2%).

At the contrary, do not increase the HCOOH rate in the injection solvent. The use of water at 0.5% formic acid as injection solvent is necessary to keep a narrow H3PO3 peak shape.

2.3.2 MS/MS Conditions

The experiments were performed on a triple-quadrupole mass spectrometer system, fitted with an electrospray interface operated in the negative ion mode under MRM (multiple reaction monitoring) conditions.

For Instance:

Detector: Triple Quadrupole HPLC-MS/MS Mass Spectrometer,
  e.g. Sciex Instruments, API 4000 System
Source: TIS (Turbo Ion Spray)
  Temperature: 650° C.
Scan Type: MRM-Mode (Multiple Reaction Monitoring Mode)
Polarity: Negative ion mode
Gas Flows: Nebulization Gas Air (GS1): 40
  Turbo Gas Air (GS2): 60
  Curtain Gas $N_2$ (CUR): 15
  Collision Gas $N_2$ (CAD): 6

Table 31 of FIG. 47 illustrates the mass spectrometer scan parameters for the quantifier ions used. The detailed instrument settings used are given in chapters 3.3.1 and 3.3.2. Varying instrument systems or instrument parameters may result in different ion transitions and different relative intensities.

Note: Some mass spectrometer conditions are instrument specific. The spectrometer conditions should be optimised by a competent operator prior to analysis.

Details on MS/MS and LC conditions are given in Appendix 11 of FIG. 61.

Figure 48A:
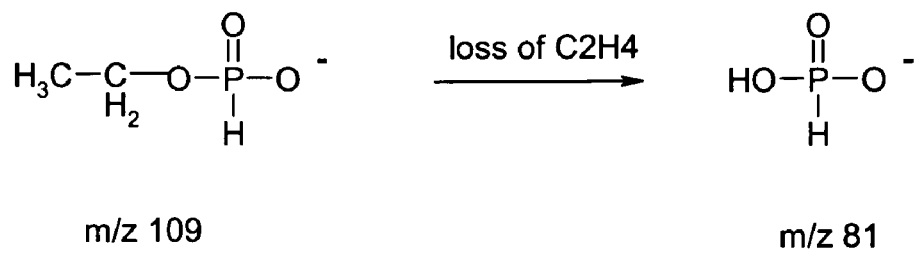
FIG. 48 illustrates fermentation pathways.
Figure 48B:
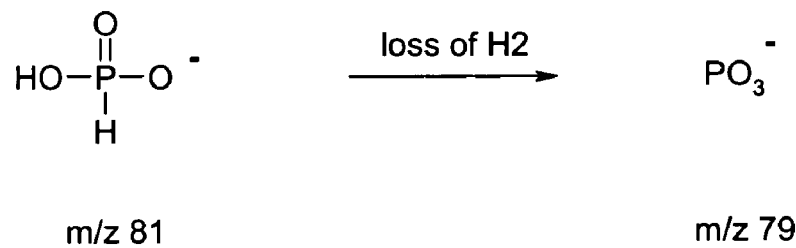

The fragmentation pathways for the quantifier ions for fosetyl-Al and phosphorous acid are shown in FIGS. 48(*a*) and (b).

2.3.3 Confirmatory Transitions

To confirm or exclude some interference or pollution in samples, the following transitions can be used in the same conditions described above and shown in FIG. 49.

Figure 50A:
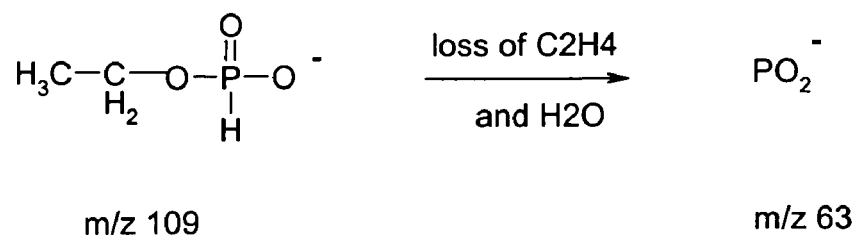
FIG. 50 illustrates fragmentation pathways.
Figure 50B:
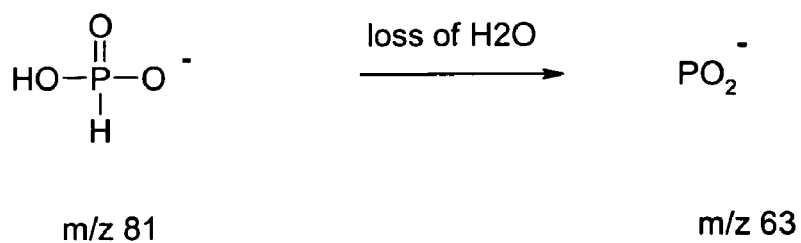

The fragmentation pathways for the confirmatory transitions for fosetyl-Al and phosphorous acid are shown in FIGS. 50(*a*) and (b).

2.4 Linearity of the Detector

The linearity of the detector used was tested for fosetyl-Al and phosphorous acid using standards in solvent and matrix matched standards.

The linearity was tested by injecting standards of fosetyl-Al and phosphorous acid at concentrations between 0.25 and 25 µg/L and is shown in Table 32 of FIG. 51.

2.5 Storage Stability of Extracts

The stability of sample extracts containing fosetyl-Al and phosphorous acid was not determined in this study.

2.6 Calculation 2.6.1 Calculation of Residues

Evaluation in this case is performed according to the external standardisation using standards prepared in solvent.

During the analysis of each set of samples, the 8 standard solutions mentioned in Table 4 are injected once. Standards should be interspersed with samples to compensate for any minor change in instrument response.

For each compound, the peak area is plotted versus the concentration in order to establish a calibration curve obtained by linear regression weighting 1/x with least squares method.

The corresponding model to determine the concentration in final extracts is calculated using the Analyst. Software (Version 1.4).

Each final extract is injected once using the same conditions as previously described for the standard solutions.

Using the predicting mathematical model previously established, the final concentration in µg/L of each compound is determined for each injection.

For each compound, the amount of residue R, expressed in mg/kg is calculated, using the following formula:

$$R = \frac{C \times \text{Weight}_{ExtractA} \times \text{Density}^{-1} \times D}{1000 \times \text{Weight}_{Sample}}$$

where:
  R Determined amount of residue of fosetyl-Al or phosphorous acid in soil sample in mg/kg
  C: Concentration of fosetyl-Al or phosphorous acid found in the analysed extract in µg/L
  $\text{Weight}_{Extract\ A}$: Weight of the extract A in g, here 200 g
  $\text{Density}^{-1}$: 1 mL/g
  D Dilution factor to obtain the Final Extract, here 10
  $\text{Weight}_{Sample}$: Sample weight of analytical sample in g, here 20 g
  The density of all solutions used during the sample preparation (ammonia buffer solution and H2O at 0.5% HCOOH) is considered equal to 1 independently to room temperature. This allows to convert the extract weight into extract volume.
  If it is necessary to express phosphorous acid in fosetyl-Al equivalent, the ratio of the molecular weight must be used:

$$\text{Ratio} = \frac{354.1 \text{ g/mol}}{(82.0 \times 3) \text{ g/mol}} = 1.44$$

because 1 mole fosetyl-Al (354.1 g) gives 3 moles of phosphorous acid.

2.6.2 Calculation of Recovery Rates

The concentration of each compound in µg/L is determined for the recovery sample according to 2.6.1.

The percent recovery rate is then calculated as follows:

$$Rec = \frac{C \times 100}{A}$$

where:
  Rec: Recovered amount found in fortified sample in %
  C: Concentration of fosetyl-Al or phosphorous acid found in the analysed extract in µg/L
  A: Fortified amount of fosetyl-Al or phosphorous acid in µg/L

2.6.3 Calculation of Relative Standard Deviation (RSD)
The RSD is calculated as follows:

$$RSD\ (\%) = S.D./\text{Mean Recovery} \times 100\%$$

$$S.D. = \left[ \frac{\sum (R_1 - R_m)^2}{n-1} \right]^{1/2}$$

$R_i$: recovery $R_m$: mean recovery $n$: number of recoveries

3 Results and Discussion
3.1 Specificity and Selectivity
The method allows the determination of fosetyl-Al and its metabolite (phosphorous acid) in soil samples.

The specificity of the method resulted from the HPLC separation in combination with the very selective MS/MS detection.

3.2 Apparent residues in Control Samples
The method was validated using the two German soils Höfchen and Laacher Hof.

Two different soils were used in order to assess a possible influence of different soil characteristics. The soil samples were classified according to DIN and/or USDA specifications. Soil characteristics of the used soils are summarised in Table 33 of FIG. 52.

Complete soil characterisation is reported in FIG. 52 and Appendix 13 of FIG. 63.

A residue level estimation in control samples was performed. The results are listed in Table 34.

The apparent residues for all control samples were below 20% of the LOQ for each compound, i.e. <0.01 mg/kg and is presented in FIG. 53.

3.3 Linearity of the Detectors and Matrix Effects
The linearity of the detector used was tested for fosetyl-Al and phosphorous acid using standards in solvent and matrix matched standards.

The linearity was tested by injecting standards of fosetyl-Al and phosphorous acid at concentrations between 0.25 and 25 µg/L.

Experimental details can be found in Chapter 2.4.

In each chromatogram, the measured peak area of fosetyl-Al or phosphorous acid is plotted versus the corresponding concentration of respectively fosetyl-Al or phosphorous acid contained in each standard solution, in order to obtain calibration curve of the form:

$$y = ax + b\ (1/x\ \text{weighting})$$

where:
y=peak area,
x=concentration in injected standard solution

The results of the determination of detector response for LC/MS/MS are summarised in Table 35 of FIG. 54.

An excellent linear correlation between the injected amount of the analytes and the detector responses of LC/MS/MS was observed for standards in the range of 0.25 to 25 µg/L for both compounds, using either standards prepared in solvent or matrix matched standards.

The occurrence of matrix effects was monitored.

The results are shown in Table 36 and Table 37 of FIGS. 55 and 56.

The results presented in the two previous Tables 36 and 37 show that:

- no significant difference is observed when the measurement of fosetyl-Al is established using either standards prepared in solvents, or matrix matched standards.
- the measurement of phosphorous acid is better (higher mean recoveries and lower RSD found) when it is established using standards prepared in solvents, instead of using matrix matched standards.

For all these reasons, we advice to use standards prepared in solvents.

3.4 Limit of Quantification and Recovery Experiments
The limit of quantification (LOQ) was defined as the lowest fortification level where a mean recovery within the range of 70 to 110% and an RSD of ☐20% could be obtained. The LOQ was set at 0.050 mg/kg for each compounds in soils samples.

To validate the method for these matrices, control samples were fortified with a defined amount of fosetyl-Al and phosphorous acid prior to analysis.

3.5 Recovery Rates
The detailed recovery results obtained are listed in Tables 38 and 39 of FIGS. 57 and 58. All results given in Tables 38 and 39 of FIGS. 57 and 58 have been obtained by using standards prepared in solvents and the quantifier ion (see 3.3.2). The results obtained with the confirmatory transition are given in Appendix 12 of FIG. 62.

The obtained recovery rates are summarised in Table 40 of FIG. 59.

In total 20 recovery rates were determined for each compound.

The previous table shows that:

The single recovery rates were in the range of 70 to 81% for fosetyl-Al and of 80 to 98% for phosphorous acid. All mean recoveries rates were in the range of 70 to 110%.

All RSD were well below 20%.

4 Evaluation and Discussion
The presented residue analytical method modification 00974/M001 was validated for the determination of residues of fosetyl-Al and its metabolite (phosphorous acid) in soils by LC/MS/MS.

The residues of fosetyl-Al and its metabolite (phosphorous acid) are extracted from the soil samples by shaking with ammonia buffer solution. This extract is then treated with a cationic resin and a final dilution is done before the analysis by LCMSMS. The residues are quantified by HPLC using an Hypercarb column and detected by tandem mass spectrometry with electrospray ionisation. The quantification was done by an external standardisation using standards prepared in pure solvent.

The validation set included the determination of the detector linearity, the limit of quantification and the accuracy of the method.

The linearity of the detector used was tested for fosetyl-Al and phosphorous acid using standards in solvent and matrix matched standards.

The linearity was tested by injecting standards of fosetyl-Al and phosphorous acid at concentrations between 0.25 and 25 µg/L. The detector response was linear in these ranges.

The occurrence of matrix effects was monitored

- no significant difference is observed when the measurement of fosetyl-Al is established using either standards prepared in solvents, or matrix matched standards;
- the measurement of phosphorous acid is better (higher mean recoveries and lower RSD found) when it is established using standards prepared in solvents, instead of using matrix matched standards.

For all these reasons, we advice to use standards prepared in solvents.

The apparent residues for all control samples were below 20% of the LOQ for each compound, i.e. <0.01 mg/kg.

The limit of quantification (LOQ) was defined as the lowest fortification level where a mean recovery within the range of 70 to 110% and an RSD of ☐20% could be obtained. The LOQ was set at 0.050 mg/kg for each compounds in soils samples.

The accuracy of the method can be assessed on the basis of the determined recovery rates. The single recovery rates were in the range of 70 to 81% for fosetyl-Al and of 80 to 98% for phosphorous acid. All mean recoveries rates were in the range of 70 to 110%. The accuracy of the method fulfils the requirements for residue analytical methods which demand that the mean recoveries for each fortification level should be in the range of 70-110%.

The precision and repeatability of the method can be assessed on the basis of the determined relative standard deviations (RSD) for the mean values of the recovery rates. All RSD were well below 20%. Thus the precision and repeatability of the method can be considered acceptable.

All results of the method validation are in accordance with the general requirements for residue analytical methods, so this method modification has been validated successfully.

During analysis, for each sample set, it is necessary to do a blank reagent without soil sample to be sure that no phosphorous acid contamination (<30% LOQ) coming from sample preparation is found.

standard laboratory glass consumable should be cleaned with only detergents containing no phosphate and rinsed with water and acetone.

To avoid any contamination, the use of disposable laboratory consumable is strongly advised.

Before start of validation/measurements equipment/chemicals should be tested for any residues of phosphorous acid.

If some contamination is observed, see if the use of special HPLC vials (e.g. polypropylene vials, Agilent, art. 5182-0567) can be helpful to reduce the background for phosphorous acid.

The invention claimed is:

1. A method for directly and simultaneously analyzing a sample for phosphorous acid and fosetyl Al present in amounts up to and including 0.00005 mg/kg in said sample comprising:

preparing the sample by a process comprising at least one step selected from the group consisting of extracting from plant tissues; extracting from soils; extracting from animal products or tissues; extracting from converted agrofood products; concentrating from water; and trapping from air;

optionally diluting or concentrating, as appropriate, the sample thus prepared; and directly analyzing the optionally diluted or concentrated sample by high performance liquid chromatography (HPLC)/tandem mass spectrometry (MS/MS);

whereby lowered limits of quantification ensuing from directive 96/46/EC can be achieved.

2. The method of claim 1 comprising the step of diluting the sample prepared.

3. The method of claim 2, for which the dilution is carried out in an aqueous solvent, which may be acidified, or in an organic solvent, which may be acidified, or in a mixture of such solvents.

4. The method of claim 3 wherein the aqueous solvent comprises an acid selected from the group consisting of formic acid, acetic acid, and trifluoroacetic acid, and the organic solvent is selected from the group consisting of acetonitrile and methanol.

5. The method of claim 1 wherein the sample is an animal product or tissue.

6. The method of claim 5 wherein the animal product or tissue is a human body fluid.

7. The method of claim 6 wherein the human body fluid is blood or urine.

8. The method of claim 6 wherein the prepared sample is diluted.

9. The method of claim 8 for which the dilution is carried out in an aqueous solvent, which may be acidified, or in an organic solvent, which may be acidified, or in a mixture of such solvents.

10. The method of claim 9 wherein the aqueous solvent comprises an acid selected from the group consisting of formic acid, acetic acid, and trifluoroacetic acid, and the organic solvent is selected from the group consisting of acetonitrile and methanol.

* * * * *